(12) United States Patent
Campos et al.

(10) Patent No.: US 6,911,206 B1
(45) Date of Patent: Jun. 28, 2005

(54) FUSION PROTEINS COMPRISING CARRIERS THAT CAN INDUCE A DUAL IMMUNE RESPONSE

(75) Inventors: Manuel Campos, Stonington, CT (US); Terecita D. Yule, Norwich, CT (US); Serge Martinod, Groton, CT (US); Becky A. Durtschi, Ledyard, CT (US)

(73) Assignees: Pfizer Inc., New York, NY (US); Pfizer Products Inc., Groton, CT (US)

(*) Notice: Subject to any disclaimer, the term of this patent is extended or adjusted under 35 U.S.C. 154(b) by 0 days.

(21) Appl. No.: 09/506,078

(22) Filed: Feb. 16, 2000

Related U.S. Application Data

(60) Provisional application No. 60/120,454, filed on Feb. 17, 1999.

(51) Int. Cl.[7] .................... A61K 39/00; A61K 39/12; A61K 39/245; A61K 38/24; C07K 17/00; C07K 38/27

(52) U.S. Cl. .................. 424/192.1; 424/185.1; 424/186.1; 424/198.1; 424/204.1; 424/229.1; 424/546; 530/350; 530/398; 530/399

(58) Field of Search .................. 424/185.1, 195.11, 424/192.1, 198.1, 204.1, 229.1, 184.1, 546, 186.1; 435/360; 536/23.4, 23.51, 23.72, 23.1; 514/8; 530/313, 350, 387.3, 388.85, 395, 397, 398, 399; 436/87

(56) References Cited

U.S. PATENT DOCUMENTS

| | | |
|---|---|---|
| 3,137,631 A | 6/1964 | Soloway |
| 3,959,457 A | 5/1976 | Speaker et al. |
| 4,016,100 A | 4/1977 | Suzuki et al. |
| 4,205,060 A | 5/1980 | Monsimer et al. |
| 4,452,747 A | 6/1984 | Gersonde et al. |
| 4,606,940 A | 8/1986 | Frank et al. |
| 4,722,840 A | 2/1988 | Valenzuela et al. |
| 4,744,933 A | 5/1988 | Rha et al. |
| 4,921,706 A | 5/1990 | Roberts et al. |
| 4,927,637 A | 5/1990 | Morano et al. |
| 4,944,948 A | 7/1990 | Uster et al. |
| 4,975,420 A | 12/1990 | Silversides et al. |
| 5,008,050 A | 4/1991 | Cullis et al. |
| 5,009,956 A | 4/1991 | Baumann |
| 5,132,117 A | 7/1992 | Speaker et al. |
| 5,151,267 A | 9/1992 | Babiuk et al. |
| 5,403,586 A | 4/1995 | Russell-Jones et al. |
| 5,422,110 A | 6/1995 | Potter et al. |
| 5,441,736 A | 8/1995 | Gerlach et al. |
| 5,545,523 A | 8/1996 | Batt et al. |
| 5,585,264 A | 12/1996 | Babiuk et al. |
| 5,599,663 A | 2/1997 | Vaughan |
| 5,612,360 A | 3/1997 | Boyd et al. |
| 5,629,292 A | 5/1997 | Rodgers et al. |
| 5,635,359 A | 6/1997 | Brunner et al. |
| 5,665,568 A | 9/1997 | Mason et al. |
| 5,684,145 A | * 11/1997 | Van Der Zee et al. ... 536/23.51 |
| 5,786,179 A | 7/1998 | Kousoulas et al. |
| 5,795,967 A | 8/1998 | Aggarwal et al. |
| 6,086,902 A | 7/2000 | Zamb et al. |

FOREIGN PATENT DOCUMENTS

| | | |
|---|---|---|
| EP | 0131363 | 1/1985 |
| EP | 0175261 | 3/1986 |
| EP | 0888777 A2 | 1/1999 |
| GB | 2140810 A | 12/1984 |
| JP | 1989171489 A1 | 7/1989 |
| JP | 1994073095 A1 | 3/1994 |
| WO | WO 84/04756 | 12/1984 |
| WO | WO 86/06635 | 11/1986 |
| WO | WO 90/02187 * | 3/1990 |
| WO | WO 91/15571 A5 | 10/1991 |
| WO | WO 92/03558 | 3/1992 |
| WO | WO 93/14209 | 7/1993 |
| WO | WO 95/28227 | 10/1995 |
| WO | WO 96/24775 | 8/1996 |
| WO | WO 98/32866 | 7/1998 |
| WO | WO 99/02180 | 1/1999 |

OTHER PUBLICATIONS

Roeske et al. (sequence alignment of SEQ ID No.: 13 with Geneseq accession No.: AAP50222, first entry: Jan. 20, 1992 by Roeske et al. in EP13573–A).*
Russelljon et al. (sequence alignment of SEQ ID No.: 15 with Geneseq accession No.: AAR11187, first entry: May 22, 1991 in WO 91/02799–A).*
Babiuk et al. (sequence alignment of SEQ ID No.: 19 with Geneseq accession No.: AAR37895, first entry: Dec. 1, 1993 in WO 93/11792–A1).*
Zhu et al. Vaccine. 1996; 14 (1): 61–69.*
Zhu et al. Vaccine. Jan. 21, 1999; 17: 269–282.*
Van Druden Littel–Van den Hurk et al. Virology. 1985; 144: 216–227.*

(Continued)

*Primary Examiner*—Shanon Foley
(74) *Attorney, Agent, or Firm*—Edward F. Rehberg; Kenneth I. Kohn; Kohn & Associates PLLC

(57) ABSTRACT

The subject invention provides a fusion protein for producing a dual immune response in a vertebrate, which fusion protein comprises: (a) a first proteinaceous portion analogous to all or part of a peptide endogenously synthesized within the vertebrate, the activity of which peptide is to be inhibited within the vertebrate, and which proteinaceous portion by itself is incapable of eliciting an effective immunoinhibitory response in said vertebrate; connected to (b) a second proteinaceous portion analogous to all or part of an immunogen from a pathogen, which pathogen is capable of pathogenically infecting the vertebrate; the portion (b) causing the vertebrate's immune system to recognize the portion (a) and produce a response that: (i) inhibits the activity of the peptide endogenously synthesized within the vertebrate; and (ii) protects the vertebrate from infection by the pathogen, when the vertebrate is vaccinated with an effective amount of the fusion protein. The subject invention also provides fusion proteins which comprise a proteinaceous portion (b) that is a carrier that is analogous to all or part of a BHV-1 antigen, which fusion proteins induce in a vertebrate vaccinated with an effective amount of such fusion protein an immune response that inhibits the activity of a peptide as recited in (a), above.

2 Claims, 32 Drawing Sheets

OTHER PUBLICATIONS

Mittal et al. 1996. Induction of systemic and mucosal immune responses in cotton rats immunized with human adenovirus type 5 recombinants expressing the full and truncated forms of bovine herpesvirus type 1 glycoprotein gD. Virology. vol. 222,pp. 299–309.*

Bakker, D. et al., Identification of Minor Fimbrial Subunits Involved in Biosynthesis of K88 Fimbriae. Journal of Bacteriology vol. 174, No. 20, pp. 6350–6358, 1992.

Engstrom, A. The Arrangment of the Protein Molecules in Nuclear–Polyhedrosis Inclusions. Biochem. Exp. Biol. 11:7–13, 1974.

Gerlach, G.F. et al. Characterization of Two Genes Encoding Distinct Transferrin–Binding Proteins in Different Actinobacillus. Infection and Immunity vol. 60, No. 8, pp. 3253–3261, 1992.

Ferro, V.A. and Stimson, W.H. Investigation into Suitable Carrier Molecules for Use in an Anti–Gonadotrophin Releasing Hormone Vaccine. Vaccine, vol. 16, No. 11/12, pp. 1095–1102, 1998.

Hsiung, N. et al. Efficient Production of Hepatitis B. Surface Antigen Using a Bovine Papilloma Virus–Metallothionein Vector. Journal of Molecular and Applied Genetics vol. 2, pp. 497–506, 1984.

Simons, B.L. et al. The Periltimate Tyrosine residue of the K99 Fibrillar Subunit is Essential for Stability of the Protein and Its Interaction with the Periplasmic Carrier Protein, FEMS Microbiol. Letters vol. 67, pp. 107–112, 1990.

Ausubel et al., 1989, Current Protocols In Molecular Biology, Greene Publishing Associates & Wiley Interscience, NY.

Bernatowics, M. and Matsueda, G., Analytical Biochemistry 155:95–102, 1986.

Chasin, M. and Langer, R. (eds), 1990, "Biodegradable Polymers as Drug Delivery Systems" in Drugs and the Pharmaceutical Sciences, vol. 45, M. Dekker, NY.

A. Domb et al., Polymers for Advanced Technologies, 3:279–292, 1992.

Erlich (ed), PCR Technology, Oxford University Press, New York, 1992.

Harlow, E., Lane, D., Antibodies, A Laboratory Manual, Cold Springs Harbor Laboratory, 1988.

Hopp and Woods, Proc. Natl. Acad. Sci. U.S.A. 78:3824, 1981.

Köhler, G., Milstein, C., Continuous cultures of fused cells secreting antibody of predefined specificity, Nature, vol. 256:495–497, Aug. 7, 1975.

Ladd, A: et al., Biol. Reprod. 51:1076–1083, 1994.

Ladd, A. et al., Biol. Reprod. 15:85–101, 1989.

Marshak, DR., Kadonaga, JT., Burgess, RR., Knuth, MW., Brennan, WA. Jr., Lin, S., "Strategies for Protein Purification and Characterization. A laboratory course manual", CSHL Press, 1996.

Sambrook et al., Molecular Cloning: A Laboratory Manual, $2^{nd}$ ed., Cold Springs Harbor Laboratory Press, Cold Springs Harbor, NY, 1989.

van Drunen Little–van der Hurk, S. et al., Vaccine 11:25–35, 1993.

Babiuk, L.A., et al., Virology 159:57–66, 1987.

Batista, F.D. et al., Nucleic Acids Res. 23(23):4805–4811, 1995.

Britton, P. et al., Virus Res. 21(3):181–198, 1991.

Cole et al., Monoclonal Antibodies and Cancer Therapy, Alan R. Liss, Inc., pp. 77–96, 1985.

Cote et al., Proc. Natl. Acad. Sci. U.S.A. 80:2026–2030, 1983.

Dimaline, R. et al., FEBS Lett. 205(2):318–322, 1986.

Dunn and Pennignton, Methods in Molecular Biology, vol. 26, Chap. 10, Humana Press Inc., 1994.

Edge. Nature, 292:756, 1981.

Eng, J. et al., Regul, Pept., 30(1):15–19, 1990.

Fairweather, N.F. et al., J. Bacteriol. 165(1):21–27, 1986.

Fitzpatrick, D.R. et al., Virology 173:456–457, 1989.

Fletterick and Zoller (eds), Current Communications in Molecular Biology, Cold Spring Harbor Laboratory, Cold Spring Harbor, NY, 1986.

Frey, J. et al., Infect. Immun. 59(9), 3026–3032, 1991.

Fritzemier, J. et al., Arch. Virol. 142(7):1335–1350, 1997.

Furze, J.M. et al., Virology 231(1):48–58, 1997.

Goding, J.W., Monoclonal Antibodies: Principles and Practice, Academic Press, London, 1986.

Gompels, U.A. et al., DNA Seq. 3(1):25–39, 1992.

Gubler, U. et al. Proc. Natl. Acad. Sci. U.S.A. 80(14):4311–4314, 1983.

Hovanec, D.L. and Air, G.M., Virology 139(2):384–392, 1984.

Innis et al. (eds.), PCR Strategies, Academic Press, Inc., San Diego, 1995.

Inoue, T. et al., FEMS Microbiol. Lett. 108(2):157–161, 1993.

Jay et al., J. Biol. Chem. 259:6311, 1984.

Jerse, A.E. et al., Proc. Natl. Acad. Sci. U.S.A. 87(20):7839–7843, 1990.

Kambadur, R. et al., Genome Res. 7(9):910–916, 1997.

Kariya, Y. et al., Gene 40(1–3):345–52, 1986.

Kim, S.J. et al., DNA Seq. 1(3):181–187, 1991.

Kokubu, T. et al., Journal of the Japan Veterinary Medical Association 51:252–55, 1998.

Kosbor et al., Immunology Today 4:72, 1983.

Leong, J. et al., Infect. Immun, 48(1):73–7, 1985.

Lindstrom, S.E. et al., Virol. 72(10):8021–31, 1998.

Maniatis et al., Molecular Cloning, A Laboratory Manual, Cold Springs Harbor Laboratory Press, Cold Springs Harbor, NY, 1989.

Misra, V. et al., Virology 173:46–57, 1988.

Nambair et al., Science 223:1299, 1984.

Nicosia, A., et al., Proc. Natl. Acad. Sci. U.S.A. 83(13):4631–4635, 1986.

Niemann, H., EMBO J. 5(10):2495–2502, 1986.

Nisson, A., FEBS Lett. 60(2):322–326, 1975.

Remington's Pharmaceutical Science, $18^{th}$ ed., Mack Publishing, 1990.

Schrijver, R.S. et al., Archives of Virology 142(11):2195–2210, 1997.

Seeburg, P.H. et al., DNA 2(1):37–45, 1983.

Shen, L.P. et al., Proc. Natl. Acad. Sci. U.S.A. 79(15):4575–4579, 1982.

Spindel, E.R. et al., Proc. Natl. Acad. Sci. U.S.A. 83(1):19–23, 1986.

Su, C.J. et al., Mol. Endocrinol. 2(3):209–216, 1988.

Thompson, S.A. et al., Mol. Microbiol. 9(1):85–96, 1993.

Whitbeck, J.C. et al., J. Virol. 62:3319–3327, 1988.

Xie, A. and Chapman, M.S., J. Mol. Biol. 264:497, 1996.

A. Ladd, Progress in the Development of Anti–LHRH Vaccine, AJRI, (1993) 29, pp. 189–194.

Tikoo, S. K., et al, Molecular Cloning, Sequencing, and Expression of Functional Bovine Herpesvirus 1 Glycoprotein gIV in Transfected Bovine Cells, Journal of Virology, Oct. (1990) pp. 5132–5142.

* cited by examiner

FIG. 4A

```
          10            20            30            40
  1  ATG G A G GGCCGACATTGGCCGTGCTGGGCGCGCTGCTCG
  1  ATGCAAGGGCCGACATTGGCCGTGCTGGGCGCGCTGCTCG 50            60            70            80
 41  CCGTTGCGGT A AGCTTGCCTACACCCGCGCCGCGGGTGAC
 41  CCGTTGCGGTGAGCTTGCCTACACCCGCGCCGCGGGTGAC 90           100           110           120
 81  GGTATACGTCGACCCGCCGGCGTACCCGATGCCGCGATAC
 81  GGTATACGTCGACCCGCCGGCGTACCCGATGCCGCGATAC 130           140           150           160
121  AACTACACTGAACGCTGGCACACTACCGGGCCCATACCGT
121  AACTACACTGAACGCTGGCACACTACCGGGCCCATACCGT 170           180           190           200
161  CGCCCTTCGCAGACGGCCGCGAGCAGCCCGTCGAGGTGCG
161  CGCCCTTCGCAGACGGCCGCGAGCAGCCCGTCGAGGTGCG 210           220           230           240
201  CTACGCGACGAGCGCGGCGGCGTGCGACATGCTGGCGCTG
201  CTACGCGACGAGCGCGGCGGCGTGCGACATGCTGGCGCTG 250           260           270           280
241  ATCGCAGACCCGCAGGTGGGGCGCACGCTGTGGGAAGCGG
241  ATCGCAGACCCGCAGGTGGGGCGCACGCTGTGGGAAGCGG 290           300           310           320
281  TACGCCGGCACGCGCGCGCGTACAACGCCACGGTCATATG
281  TACGCCGGCACGCGCGCGCGTACAACGCCACGGTCATATG 330           340           350           360
321  GTACAAGATCGAGAGCGGGTGCGCCCGGCCGCTGTACTAC
321  GTACAAGATCGAGAGCGGGTGCGCCCGGCCGCTGTACTAC 370           380           390           400
361  ATGGAGTACACCGAGTGCGAGCCCAGGAAGCACTTTGGGT
361  ATGGAGTACACCGAGTGCGAGCCCAGGAAGCACTTTGGGT 410           420           430           440
401  ACTGCCGCTACCGCACACCCCGTTTTGGGACAGCTTCCT
401  ACTGCCGCTACCGCACACCCCGTTTTGGGACAGCTTCCT
```

FIG. 4B

```
            450         460         470         480
441  GGCGGGCTTCGCCTACCCCACGGACGACGAGCTGGGACTG
441  GGCGGGCTTCGCCTACCCCACGGACGACGAGCTGGGACTG 490         500         510         520
481  ATTATGGCGGCGCCCGCGCGGCTCGTCGAGGGCCAGTACC
481  ATTATGGCGGCGCCCGCGCGGCTCGTCGAGGGCCAGTACC 530         540         550         560
521  GACGCGCTGTACATCGACGGCACGGTCGCCTATACAGA
521  GACGCGCTGTACATCGACGGCACGGTCGCCTATACAGA 570         580         590         600
561  TTTCATGGTTTCGCTGCCGGCCGGGGACTGCTGGTTCTCG
561  TTTCATGGTTTCGCTGCCGGCCGGGGACTGCTGGTTCTCG 610         620         630         640
601  AAACTCGGCGCGGCTCGCGGGTACACCTTTGGCGCGTGCT
601  AAACTCGGCGCGGCTCGCGGGTACACCTTTGGCGCGTGCT 650         660         670         680
641  TCCCGGCCCGGGATTACGAGCAAAAGAAGGTTCTGCGCCT
641  TCCCGGCCCGGGATTACGAGCAAAAGAAGGTTCTGCGCCT 690         700         710         720
681  GACGTATCTCACGCAGTACTACCCGCAGGAGGCACACAAG
681  GACGTATCTCACGCAGTACTACCCGCAGGAGGCACACAAG 730         740         750         760
721  GCCATAGTCGACTACTGGTTCATGCGCCACGGGGCGTCG
721  GCCATAGTCGACTACTGGTTCATGCGCCACGGGGCGTCG 770         780         790         800
761  TTCCGCCGTATTTTGAGGAGTCGAAGGGCTACGAGCCGCC
761  TTCCGCCGTATTTTGAGGAGTCGAAGGGCTACGAGCCGCC 810         820         830         840
801  GCCTGCCGCCGATGGGGGTTCCCCGCGCCACCCGGCGAC
801  GCCTGCCGCCGATGGGGGTTCCCCGCGCCACCCGGCGAC 850         860         870         880
841  GACGAGGCCCGCGAGGATGAAGGGGAGACCGAGGACGGGG
841  GACGAGGCCCGCGAGGATGAAGGGGAGACCGAGGACGGGG
```

FIG. 4C

```
                890           900          910          920
881  CAGCCGGGCGGGAGGGCAACGGCGGCCCCCAGGACCCGA
881  CAGCCGGGCGGGAGGGCAACGGCGGCCCCCAGGACCCGA 930          940          950          960
921  AGGCGACGGCGAGACTCAGACCCCGAAGCCAACGGAGGC
921  AGGCGACGGCGAGAGTCAGACCCCGAAGCCAACGGAGGC 970          980          990         1000
961  GCCGAGGGCGAGCCGAAACCCGGCCCCAGCCCCGACGCCG
961  GCCGAGGGCGAGCCGAAACCCGGCCCCAGCCCCGACGCCG 1010         1020         1030         1040
1001 ACCGCCCCGAAGGCTGGCCGAGCCTCGAAGCCATCACGCA
1001 ACCGCCCCGAAGGCTGGCCGAGCCTCGAAGCCATCACGCA 1050         1060         1070         1080
1041 CCCCCCGCCCGCCCCCGCTACGCCCGCTCGAGCTCCGGAC
1041 CCCCCCGCCCGCCCCCGCTACGCCCGC---GGCCCCGAC

→TM                              —TM—
               1090         1100         1110         1120
1081 GCTGTTTCGGTTTCTGTTGGTATCGGTATCGCTGCTGCTG
1078 GCCGTGCCGGTCAGCGTCGGGATCGGCATTGCGGCTGCGG 1130         1140         1150         1160
1121 CTATCGCTTGCGTTGCTGCTGCTGCTGCTGGTGCTTACTT
1158 CGATCGCGTGCGTGGCCGCCGCCGCCGGCGCGTACTT 1170         1180         1190         1200
1161 CGTTTATATTCGTCGTCGTGGTGCTGGTCCGCTGCCGCGT
1158 CGTCTATACGCCGGCGCGGTGCGGGTCCGCTGCCCAGA 1210         1220         1230         1240
1201 AAACCGAAAAAACTGCCGGCTTTCGGTAACGTTAACTACA
1198 AAGCCAAAAAAGCTGCCGGCCTTTGGCAACGTCAACTACA 1250
1241 GTGCTCTGCCGGGTTGA
1238 GCGCGCTGCCCGGGTGA
```

FIG. 5

```
         10         20         30         40
  1  MCGPTLAVLGALLAVAVSLPTPAPRVTVYVDPPAYPMRY
  1  M[E]GPTLAVLGALLAVAVSLPTPAPRVTVYVDPPAYPMRY 50         60         70         80
 41  NYTERWHTTGPIPSPFADGREQPVEVRYATSAAACDMLAL
 41  NYTERWHTTGPIPSPFADGREQPVEVRYATSAAACDMLAL 90        100        110        120
 81  IADPQVGRTLWEAVRRHARAYNATVIWYKIESGCARPLYY
 81  IADPQVGRTLWEAVRRHARAYNATVIWYKIESGCARPLYY 130        140        150        160
121  MEYTECEPRKHFGYCRYRTPPFWDSFLAGFAYPTDDELGL
121  MEYTECEPRKHFGYCRYRTPPFWDSFLAGFAYPTDDELGL 170        180        190        200
161  IXAAPARLVEGQYRRALYIDGTVAYTDFMVSLPAGDCWFS
161  IXAAPARLVEGQYRRALYIDGTVAYTDFMVSLPAFDCWFS 210        220        230        240
201  KLGAARGYTFGACFPARDYEQKKVLRLTYLTQYYPQEAHK
201  KLGAARGYTFGACFPARDYEQKKVLRLTYLTQYYPQEAHK 250        260        270        280
241  AIVDYWFMRHGGVVPPYFEESKGYEPPPAADGGSPAPPGD
241  AIVDYWFMRHGGVVPPYFEESKGYEPPPAADGGSPAPPGD 290        300        310        320
281  DEAREDEGETEDGAAGREGNGGPPGPEGDGESQTPEANGG
281  DEAREDEGETEDGAAGREGNGGPPGPEGDGESQTPEANGG 330        340        350        360
321  AEGEPKPGPSPDADRPEGWPSLEAITHPPPAPATPA[-]APD
321  AEGEPKPGPSPDADRPEGWPSLEAITHPPPAPATPA[R]APD 370        380        390        400
360  AV[P]VSVGIGIAAAAIACVAAAAGAYFVYTRRRGAGPLPR
361  AV[S]VSVGIGIAAAAIACVAAAAGAYFVY[I]RRRGAGPLPR 410
400  KFKKLPAFGNVNYSALPG [*]
401  KFKKLPAFGNVNYSALPG [*]
```

FIG. 6A

```
CTCGAGAAATCATAAAAAATTTATTTGCTTTGTGAGCGGATAACAATTGTGAGCGGATAACAATT     80
GAGCTCTTTAGTATTTTTTAAATAAACGAAACACTCGCCTATTGTTAATATTCTAAGTTAACACTTCGCCTATTGTTAA
TCACACAGAATTCATTAAAGAGGAGAAATTAACTATGAGAGGATCTCACCATCACCATCACCATCACGGATCCGCATGCCA    160
                                  ─────────── 6x his:MgD coding seq ──────────
AGTGTGTCTTAAGTAATTCTCCTCTTTAATTGATACTCCTAGAGTGGTAGTGGTATGCCTAGGCGTACGGT
                                                    ↑
                                          ─────── 6x His leader ────────
             Met Arg Gly Ser His His His His His His Asp Pro His Ala
                                  ────────── 6x his:MgD coding seq ──────────

TGAGCTTGCCTACACCCGCCGCCGGGGTGACGTCGACCCCGCCGGGGTATACGTCGACCCCGCCGGGGTGACGCCGATACAACTACACT     240
ACTCGAACGGATGTGGGCCGCCGCGGGCCGCCACTGCCATATGCAGCTGGGCGCCGCCATGGCGCTACGGCGCTATGTGATGTGA
Met Ser Leu Pro Thr Pro Ala Pro Arg Val Thr Val Tyr Val Asp Pro Pro Ala Tyr Pro Met Pro Arg Tyr Asn Tyr Thr
                                  ─────────── 6x his:MgD coding seq ──────────
GAACGCTGGCACACTACCGGCCCATACCGGCCCCTTCGCCAGACGCCCGAGCAGCCCGTCGAGGTGCCGCTACGCGAC    320
                        ──────────────── gD coding sequence ────────────────
CTTGCGACCGTGTGATGGCCCGGGTATGCCCGGGTATGGCCAGCGGGAAGCGTCTGCCGGGTCGGGCTCGTGCCAGCTCCACGCGATGCGCTG
                        ──────────────── gD coding sequence ────────────────
Glu Arg Trp His Thr Thr Gly Pro Ile Pro Ser Pro Phe Ala Asp Gly Arg Glu Gln Pro Val Glu Val Arg Tyr Ala Thr
                                  ─────────── 6x his:MgD coding seq ──────────
```

FIG. 6B

```
GAGCGCGGCGGCGTGCGACATGCTGGCGCTGATCGCCAGACCCGCAGGTGGGCGCACGCTGTGGGAAGCGGTACGCCGGC
                                                                             400
CTCGCGCCGCCGCACGCTGTACGACCGCGACTAGCGGTTCTCGGGCGTCCACCCCGCGTGCGACACCCTTCGCCATGCGGCCG
         gD coding sequence
Ser Ala Ala Ala Cys Asp Met Leu Ala Leu Ile Ala Asp Pro Gln Val Gly Arg Thr Leu Trp Glu Ala Val Arg Arg
                                                       6x his:MgD coding seq ACGCGCGGCGTACAACGCCACGGTCATATGGTACAAGATCGAGAGCGGGTGCGCCCGGCTGTACTACATGGAGTAC
                                                                           480
TGCGCGCCGCATGTTGCGGTGCCAGTATACCATGTTCTAGCTCTCGCCCACGCGGGCGACATGATGTACTTCATG
         gD coding sequence
His Ala Arg Ala Tyr Asn Ala Tyr Val Ile Trp Tyr Lys Ile Glu Ser Gly Cys Ala Arg Pro Leu Tyr Tyr Met Glu Tyr
                                                       6x his:MgD coding seq ACCGAGTGCGAGCCCAGGAAGCACTTTGGGTACTGCCGCTACCGCACACCCCGTTTTGGGACAGCTTCCTGGCGGGCTT
                                                                             560
TGGCTCACGCTCGGGTCCTTCGTGAAACCCATGACGGCGATGGCGTGTGGGGCAAAACCCTGTCGAAGGACCGCCCGAA
         gD coding sequence
Thr Glu Cys Glu Pro Arg Lys His Phe Gly Tyr Cys Arg Tyr Arg Thr Pro Pro Phe Trp Asp Ser Phe Leu Ala Gly Phe
                                                       6x his:MgD coding seq
```

```
CGCGAGGATGAAGGGGAGACCGAGGAGGGCAACGGGCCCCCAGGACCCGAAGGCGACGG
                                                            1040
GCGCTCCTACTTCCCCTCTGGCTCCGTTGCCGGGGGTCCTGGGCTTCCGCTGCC
Arg Glu Asp Glu Gly Glu Thr Glu Glu Gly Asn Gly Pro Pro Gly Pro Glu Gly Asp Gly
                          gD coding sequence
                             6x his:MgD coding seq CGAGAGTCAGACCCCCGAGGGCGAGCCAAGCCGAAAACCCGGCTTTGGGCCTGGGGGC
                                                            1120
GCTCTCAGTCTGGGGGCTCGGTTCGGCTTCGGTTGCCTCCGCGGTCCCCGCGGTTTTGGGCCGAAACCCGGACTCCCG
Arg Glu Asp Glu Gly Thr Glu Glu Gly Arg Glu Gly Asn Gly Pro Pro Gly Pro Glu Gly Asp Gly
                           gD coding sequence
                             6x his:MgD coding seq AAGGCTGGCCGAGCCTGAAGCCATCACGCGCCCCCGCTACGCCCGCTCGAGCTCGGTACCCCGGTCG
                                                            1200
TTCCGACCGGCTCGGACTTCGGAGCTTCGGTAGTGCGCGGGGGCGATGCGGAGCTCGAGCCATGGGGCCCAGC
Glu Ser Gln Thr Pro Glu Ala Asn Gly Gly Ala Glu Gly Glu Pro Lys Pro Gly Pro Ser Pro Asp Ala Asp Arg Pro
                                gD coding sequence
                             6x his:MgD coding seq
                                                   vector coding seq ACCTGCAGCCAAGCTTAATTAGCTTGGACTTCCTGTTGATAGATCCAGTAATGACCTCAGAACTCCATCTGGATTT
                                                            1280
TGGACGTCGGTTCGAATTAATCGAACTGAGGACAACTATCTAGGTCATTACTGGAGTCTTGAGGTAGACCTAAA
Glu Gly Trp Pro Ser Leu Glu Ala Ile Thr His Pro Pro Pro Ala Thr Pro Ala Arg Ala Arg Tyr Pro Gly Ser
                                gD coding sequence
                             6x his:MgD coding seq
                                                   vector coding seq Thr Cys Ser Gln Ala *
6x his:MgD coding seq
```

FIG. 7B

```
     CGTCGCCCTTCGCAGACGGGCCGCGAGCAGCCCGTCGAGGTGCGCTACGCGACGAGCGCGGCGGCCGTGCGACATGCTGGCG
                                                                                    480
     ────────────────────────────── gD coding sequence ──────────────────────────────
                                    ────── His-LHRH-gD fusion ──────
     Pro Ser Pro Phe Ala Asp Gly Arg Glu Gln Pro Val Arg Tyr Ala Thr Ser Ala Ala Cys Asp Met Leu Ala CTGATCGCAGACCCGCAGGTGGGGCGCACGCTGTGGGAAGCGGGTACGCGCCGGCACGCGCGCGGTACAACGCCACGGTCAT
                                                                                    560
     ────────────────────────────── gD coding sequence ──────────────────────────────
                                    ────── His-LHRH-gD fusion ──────
     Leu Ile Ala Asp Pro Gln Val Gly Arg Thr Leu Trp Glu Ala Val Arg Arg His Ala Arg Ala Tyr Asn Ala Thr Val Ile ATGGTACAAGATCGAGAGCGGGTGCGCCCGGCTGTACTACATGGAGTACACCGAGTGCGAGCCCAGGAAGCACTTTG
                                                                                    640
     ────────────────────────────── gD coding sequence ──────────────────────────────
                                    ────── His-LHRH-gD fusion ──────
     Trp Tyr Lys Ile Glu Ser Gly Cys Ala Arg Pro Leu Tyr Tyr Met Glu Tyr Thr Glu Cys Glu Pro Arg Lys His Phe GGTACTGCCGCTACCGCACACCCCGTTTTGGGACAGCTTCCTGGCGGGCTTCGCCTACCCCACGGACGACGAGCTGGGA
                                                                                    720
     ────────────────────────────── gD coding sequence ──────────────────────────────
                                    ────── His-LHRH-gD fusion ──────
     Gly Tyr Cys Arg Tyr Arg Thr Pro Pro Phe Trp Asp Ser Phe Leu Ala Gly Phe Ala Tyr Pro Thr Asp Asp Glu Leu Gly CTGATTATGGCGGCGCCCGCGGCTCGTCGAGGGCCAGTACGACCGCGCTGTACATGACGGCACGGTGCGCCTATAC
                                                                                    800
     ────────────────────────────── gD coding sequence ──────────────────────────────
                                    ────── His-LHRH-gD fusion ──────
     Leu Ile Met Ala Ala Pro Ala Arg Leu Val Glu Gly Gln Tyr Arg Arg Ala Leu Tyr Ile Asp Gly Thr Val Ala Tyr Thr
```

FIG. 7C

```
AGATTTCATGGTTTCGCTGCCGGGGACTGCTGTTCTCGGTTCTCGAAACTCGGCGGCCTCGCGGGTACACCTTTGGCGCGT
                                                                              880
         gD coding sequence
Asp Phe His Gly Phe Ala Ala Gly Asp Cys Trp Phe Ser Lys Leu Gly Ala Ala Arg Gly Tyr Thr Phe Gly Ala
                                      His-LHRH-gD fusion GCTTCCCGGCCCGGGATTACGAGCAAAAGAAGGTTCTGCGCCTGACGTATCTCACGCGACTACCCGCAGGAGGCACAC
                                                                              960
                  gD coding sequence
Cys Phe Pro Ala Arg Asp Tyr Gly Gln Lys Lys Val Leu Arg Leu Thr Tyr Leu Thr Gln Tyr Tyr Pro Gln Glu Ala His
                                      His-LHRH-gD fusion AAGGCCATAGTCGACTGGTTCATGCGCCACGGGGGCGTGTTCCGCCGTATTTGAGGAGTCGAAGGGCTACGAGCC
                                                                             1040
         gD coding sequence
Lys Ala Ile Val Asp Tyr Trp Phe Met Arg His Gly Gly Val Val Pro Tyr Phe Glu Glu Ser Lys Gly Tyr Glu Pro
                                      His-LHRH-gD fusion GCCGCCTGCCGCCGGCGATGGGGGGTTCCCCCGCGAGGACGACGAGGCCCGCGAGGATGAAGGGGAGACCGAGGACG
                                                                             1120
                  gD coding sequence
Pro Pro Ala Ala Asp Gly Gly Ser Pro Ala Pro Gly Asp Glu Asp Glu Gly Ala Arg Glu Asp Gly Glu Thr Glu Asp
                                      His-LHRH-gD fusion GGGCAGCCGGGCGGGGAGGGCAACGGCGGCCCCCCAGGACCCGAAGGCGAGACCCAGAGTCAGACCCCGAAGCCAACGGA
                                                                             1200
         gD coding sequence
Gly Ala Ala Gly Arg Glu Gly Asn Gly Gly Pro Pro Gly Pro Pro Gly Asp Gly Glu Ser Gln Thr Pro Glu Ala Asn Gly
                                      His-LHRH-gD fusion
```

FIG. 8A

```
CTCGAGAAATCATAAAAATTTATTTGCTTTGTGAGCGGATAAACAATTCAATTGTGAGCGGATAACAATT     80

TCACACAGAATTCATTAAAGAGGAGAAATTAACTATGAGAGGATCTCACCATCACCATCACCATGCCA    160
                                   Met Arg Gly Ser His His His His His His Thr Asp Pro His Ala
                                   ├─────── 6X His Leader ───────┤
                                                                    ├─ His-gD-LHRH fusion ─

TGAGCTTGCCTACACCCGCGCGGGTGACGTCGACCCGCCGGTATACGTCGACCCGATGCCGCGATACAACTACACT    240
 ─────────────────── mature gD coding seq ───────────────────
Met Ser Leu Pro Thr Pro Ala Pro Arg Val Tyr Val Asp Pro Pro Ala Tyr Pro Met Pro Arg Tyr Asn Tyr Thr
 ──────────────────── His-gD-LHRH fusion ────────────────────

GAACGCTGGCACACTACCGGGCCCATACGGTGCGCCTTGCGCAGACGGCCGGAGCAGCCCGTGAGGTGCGCTACGCGGAC    320
 ──────────────────── mature gD coding seq ────────────────────
Glu Arg Trp His Thr Thr Gly Pro Ile Pro Ser Pro Phe Ala Asp Gly Arg Glu Gln Pro Val Arg Tyr Ala Thr
 ───────────────────── His-gD-LHRH fusion ─────────────────────
```

FIG. 8B

```
                                                                        400
GAGGCGGCGGGGCGGTGCGACATGCTGGCGCTGATCGCAGACCCGCAGGTGGGGCGCACGCTGTGGGAAGCGGTACGCCGGC
         ————————————————————— mature gD coding seq —————————————————————
Ser Ala Ala Ala Cys Asp Met Leu Ala Leu Ile Ala Asp Pro Gln Val Gly Arg Thr Leu Trp Glu Ala Val Arg Arg
         ————————————————————— His-gD-LHRH fusion —————————————————————

480
ACGCGCGCGTACAACGCCACGGTCATATGGTACAAGATCGAGAGCGGGTGCGCCCGGCCCCTGTACTACATGGAGTAC
         ————————————————————— mature gD coding seq —————————————————————
His Ala Arg Ala Tyr Asn Ala Thr Val Ile Trp Tyr lys Ile Glu Ser Gly Cys Ala Arg Pro Leu Tyr Tyr Met Glu Tyr
         ————————————————————— His-gD-LHRH fusion —————————————————————

560
ACCGAGTGCGAGCCCAGGAAGCACTTTGGGTACTGCCGCTACCGCACACCCCGTTTTGGGACAGCTTCCTGGCGGGCTTT
         ————————————————————— mature gD coding seq —————————————————————
Thr Glu Cys Glu Pro Arg Lys His Phe Gly Tyr Cys Arg Tyr Arg Thr Pro Pro Phe Trp Asp Ser Phe Leu Ala Gly Phe
         ————————————————————— His-gD-LHRH fusion —————————————————————

640
CGCCTACCCCACGGACGACGAGCTGGGACTGATTATGGCGGCCCGCCTCGTCGAGGCCCAGTACCGACGCGCGC
         ————————————————————— mature gD coding seq —————————————————————
Ala Tyr Pro Thr Asp Asp Glu Leu Gly Leu Ile Met Ala Ala Arg Leu Val Glu Gly Gln Tyr Arg Arg Ala
         ————————————————————— His-gD-LHRH fusion —————————————————————

720
TGTACATCGACGGCACGGTCGCCTATACAGATTCATGGTTTCGCTGCTGCGGGGACTGCTGGTTCTCGAAACTCGGC
         ————————————————————— mature gD coding seq —————————————————————
Leu Tyr Ile Asp Gly Thr Val Ala Tyr Thr Asp Phe Met Val Ser Leu Pro Ala Gly Asp Cys Trp Phe Ser Lys Leu Gly
         ————————————————————— His-gD-LHRH fusion —————————————————————
```

FIG. 8C

```
                                                                              800
GCGGCTCGCGGGGTACACCTTTGGCGCGTGCTGCTTCCCGGCCCCGGGATTACGAGCAAAAGAAGGTTCTGCGCCTGACGTATCT
─────────────────────────────────────────────────────────────────────────────────────
 Ala Ala Arg Gly Tyr Thr Phe Gly Ala Cys Phe Pro Ala Arg Asp Tyr Glu Gln Lys Lys Val Leu Arg Leu Thr Tyr Leu
                           mature gD coding seq
                           His-gD-LHRH fusion 880
CACGCACTACTACCCGCAGGAGGCACACAAGGCCATAGTCGACTACTGTTCATGCGCCACGGGGCGTCGTTCCGCCGT
──────────────────────────────────────────────────────────────────────────────
 Thr Gln Tyr Tyr Pro Gln Glu Ala His Lys Ala Ile Val Asp Tyr Trp Phe Met Arg His Gly Gly Val Val Pro Pro
                           mature gD coding seq
                           His-gD-LHRH fusion 960
ATTTTGAGGAGTCGAAGGGCTACGAGCCTGCCGCCGATGGGGTTCCCCGCCACCGGCGACGACGAGGCC
─────────────────────────────────────────────────────────────────────
 Tyr Phe Glu Glu Ser Lys Gly Tyr Glu Pro Pro Ala Ala Asp Gly Val Pro Ala Pro Gly Ser Pro Ala Pro Gly Asp Asp Glu Ala
                           mature gD coding seq
                           His-gD-LHRH fusion 1040
CGCGAGGATGAAGGGGGAGAAGGCGCGGGGCGGAGGCGCAACGGCCCCCGAGGACCCCGAAGGCGACGG
────────────────────────────────────────────────────────────────────
 Arg Glu Asp Glu Gly Glu Thr Glu Asp Gly Ala Ala Gly Arg Gly Gly Asn Gly Pro Gly Pro Gly Asp Gly
                           mature gD coding seq
                           His-gD-LHRH fusion 1120
CGAGAGTCAGACCCCGAAGCCAACGGAGGGCGAGCCCGAAACCCGGCCCCAGCCCGACGCCGACCGCCCCG
───────────────────────────────────────────────────────────────────────
 Glu Ser Gln Thr Pro Glu Ala Asn Gly Gly Ala Glu Gly Glu Gly Pro Lys Pro Gly Pro Ser Pro Asp Ala Asp Arg Pro
                           mature gD coding seq
                           His-gD-LHRH fusion
```

FIG. 9B

ATGGTACAAGATCGAGAGCGGGTGCGCCCGGCCGCTGTACTACATGGAGTACACCGAGTGCGAGCCCAGGAAGCACTTTG 640 gD coding sequence

Trp Tyr Lys Ile Glu Ser Gly Cys Ala Arg Pro Leu Tyr Tyr Met Glu Tyr Thr Glu Cys Glu Pro Arg Lys Hrs Phe

His-LHRH-gD-LHRH fusion

GGTACTGCCGCTACCGCACACCCCCGTTTTGGGACAGCTTCCTGGCGGGCTTCGCCTACCCCACGGACGACGAGCTGGGA 720 gD coding sequence

Gly Tyr Cys Arg Tyr Arg Thr Pro Pro Phe Trp Asp Ser Phe Leu Ala Gly Phe Ala Tyr Pro Thr Asp Asp Glu Leu Gly

His-LHRH-gD-LHRH fusion

CTGATTATGGCGGCGCCCGCGCGGCTCGTCGAGGGCCAGTACCGACGCGCGCTGTACATCGACGGCACGGTCGCCTATAC 800 gD coding sequence

Leu Ile Met Ala Ala Pro Ala Arg Leu Val Glu Gly Gln Tyr Arg Arg Ala Leu Tyr Ile Asp Gly Thr Val Ala Tyr Thr

His-LHRH-gD-LHRH fusion

AGATTTCATGGTTTCGCTGCCGGCCGGGGACTGCTGGTTCTCGAAACTCGGCGCGGCTCGCGGGTACACCTTTGGCGCGT 880 gD coding sequence

Asa Phe Met Val Ser Leu Pro Ala Glv Asa Cys Tro Phe Ser Lys Leu Gly Ala Ala Arg Gly Tyr Thr Phe Gly Ala

His-LHRH-gD-LHRH fusion

FIG. 9C

GCTTCCCGGCCCGGGATTACGAGCAAAAGAAGGTTCTGCGCCTGACGTATCTCACGCAGTACTACCCGCAGGAGGCACAC 960 gD coding sequence

Cys Phe Pro Ala Arg Asa Tyr Glu Gln Lys Lys Val Leu Arg Leu Thr Tyr Leu Thr Gln Tyr Tyr Pro Gln Glu Ala His

His-LHRH-gD-LHRH fusion

AAGGCCATAGTCGACTACTGGTTCATGCGCCACGGGGGCGTCGTTCCGCCGTATTTTGAGGAGTCGAAGGGCTACGAGCC 1040

CGCAGCAAGGCGGCATAAAACTCCTCAGCTTCCCGATGCTCGG gD coding sequence

Lys Ala Ile Val Asa Tyr Trp Phe Met Arg His Gly Gly Val Val Pro Pro Tyr Phe Glu Glu Ser Lys Gly Tyr GTlu Pro

His-LHRH-gD-LHRH fusion

GCCGCCTGCCGCCGATGGGGGTTCCCCCGCGCCACCCGGCGACGACGAGGCCCGCGAGGATGAAGGGGAGACCGAGGACG 1120 gD coding sequence

Pro Pro Ala Ala Asp Gly Gly Ser Pro Ala Pro Pro Gly Asp Asp Glu Ala Arg Glu Asp Glu Gly Glu Thr Glu Asp

His-LHRH-gD-LHRH fusion

FIG. 11B

```
TTGGGTACTGCCGCTACCGCACACCCCCGTTTGGACAGCTTCCTCGGCGGGCTTCGCCTACCCCACGGACGACGAGCTGGACTGATTATGGCGGCGCC     +500
                                      ━━━━━━━━━━━━━━━━━━━━━━━━━━━━━━━━━━━━━━━━━━━━━━━━━━━━━━━━━
                                                              Mature gD
Phe Gly Tyr Cys Arg Tyr Arg Thr Pro Pro Phe Trp Asp Ser Phe Leu Ala Gly Phe Ala Tyr Pro Thr Asp Glu Leu Gly Leu Ile Met Ala Ala Pro
                                                    gD coding sequence CGCGCGGCTCGTCGAGGGCCAGTACCGACATCGACGCGCGCCTGTACACAGATTTCATGGTTTCGCTCGCCGGCCGGGGACTGCTGG                +600
                                                                            ━━━━━━━━━━━━━━━━
                                                                              Mature gD
Ala Arg Leu Val Glu Gly Gln Tyr Arg Arg Ala Leu Tyr Ile Asp Gly Thr Val Ala Tyr Thr Asp Phe Met Val Ser Leu Pro Ala Gly Asp Cys Trp
                                                    gD coding sequence
                                                                        CGACGGCCGGCCCCTGACGACC TTCTCGAAACTCGGCGCGGCTCGCGGGTACACCTTTTGGGCGCGGTGCTTCCCCGGCCCCGGATTACGAGCAAAAGAAGTTCTGCGCCTGACGTATCTCACGC  +700
                                ━━━━━━━━━━━━━━━━━━━━━━━━━━━━━━━━━━━━━━━━━━━━━━━━━━━━━━━━━━━━━━
                                                           Mature gD
Phe Ser Lys Leu Gly Ala Ala Arg Gly Tyr Thr Phe Gly Ala Cys Phe Pro Ala Arg Asp Tyr Glu Gln Lys Lys Val Leu Arg Thr Tyr Leu Thr
                                                    gD coding sequence AGTACTACCCGCAGGAGGCACACAAGGCCATAGTGCGACTACTGGTTCATGCGCCACCACGGGGGCGTCGTTCCGCCGTATTTTGAGGAGTCGAAGGGCTACGA  +800
                                                                            ━━━━━━━━━━━━━━━━━━
                                                                               Mature gD
Gln Tyr Tyr Pro Gln Glu Ala His Lys Ala Ile Val Asp Tyr Trp Phe Met Arg His Gly Gly Val Val Pro Pro Tyr Phe Glu Glu Ser Lys Gly Tyr Glu
                                                     gD coding sequence
```

FIG. 12B

SEQUENCE LISTING

```
<160> NUMBER OF SEQ ID NOS: 46

<210> SEQ ID NO 1
<211> LENGTH: 33
<212> TYPE: DNA
<213> ORGANISM: Artificial Sequence
<220> FEATURE:
<223> OTHER INFORMATION: Description of Artificial Sequence: SYNTHETIC
      OLIGONUCLEOTIDE COMPRISING GNRH CODING SEQUENCE
      AND  CLONING ENDS

<400> SEQUENCE: 1
catggaacac tggtcttatg gtctgcgtcc ggg                                33

<210> SEQ ID NO 2
<211> LENGTH: 33
<212> TYPE: DNA
<213> ORGANISM: Artificial Sequence
<220> FEATURE:
<223> OTHER INFORMATION: Description of Artificial Sequence: SYNTHETIC
      OLIGONUCLEOTIDE COMPRISING GNRH CODING SEQUENCE
      AND  CLONING ENDS

<400> SEQUENCE: 2
catggaacac tggtcttatg gtctgcgtcc ggg                                33

<210> SEQ ID NO 3
<211> LENGTH: 36
<212> TYPE: DNA
<213> ORGANISM: Artificial Sequence
<220> FEATURE:
<223> OTHER INFORMATION: Description of Artificial Sequence: SYNTHETIC
      OLIGONUCLEOTIDE COMPRISING GNRH CODING SEQUENCE
      AND  CLONING ENDS

<400> SEQUENCE: 3
gatctggaac actggtctta tggtctgcgt ccgggc                             36
```

```
<210> SEQ ID NO 4
<211> LENGTH: 36
<212> TYPE: DNA
<213> ORGANISM: Artificial Sequence
<220> FEATURE:
<223> OTHER INFORMATION: Description of Artificial Sequence: SYNTHETIC
      OLIGONUCLEOTIDE COMPRISING GNRH CODING SEQUENCE
      AND  CLONING ENDS

<400> SEQUENCE: 4
gatcgcccgg acgcagacca taagaccagt gttcca                                 36

<210> SEQ ID NO 5
<211> LENGTH: 76
<212> TYPE: DNA
<213> ORGANISM: Artificial Sequence
<220> FEATURE:
<223> OTHER INFORMATION: Description of Artificial Sequence: SYNTHETIC
      OLIGONUCLEOTIDE COMPRISING GNRH CODING SEQUENCE
      AND  CLONING ENDS

<400> SEQUENCE: 5
gatccatgga gcactggtca tatggtctgc gtccgggtga acattggagc tacggtctac       60
gccccgggtc catggc                                                       76

<210> SEQ ID NO 6
<211> LENGTH: 76
<212> TYPE: DNA
<213> ORGANISM: Artificial Sequence
<220> FEATURE:
<223> OTHER INFORMATION: Description of Artificial Sequence: SYNTHETIC
      OLIGONUCLEOTIDE COMPRISING GNRH CODING SEQUENCE
      AND  CLONING ENDS

<400> SEQUENCE: 6
tcgagccatg gacccggggc gtagaccgta gctccaatgt cacccggac gcagaccata        60 tgaccagtgc tccatg                                                       76

<210> SEQ ID NO 7
<211> LENGTH: 71
<212> TYPE: DNA
<213> ORGANISM: Artificial Sequence
<220> FEATURE:
<223> OTHER INFORMATION: Description of Artificial Sequence: SYNTHETIC
      OLIGONUCLEOTIDE COMPRISING GNRH CODING SEQUENCE
      AND  CLONING ENDS

<400> SEQUENCE: 7
ggggaacact ggtcttatgg cttacggccg ggagagcatt ggagttacgg cctccgtcca       60
ggttccatgg c                                                            71

<210> SEQ ID NO 8
<211> LENGTH: 75
<212> TYPE: DNA
<213> ORGANISM: Artificial Sequence
<220> FEATURE:
<223> OTHER INFORMATION: Description of Artificial Sequence: SYNTHETIC
      OLIGONUCLEOTIDE COMPRISING GNRH CODING SEQUENCE
      AND  CLONING ENDS

<400> SEQUENCE: 8
tcgagccatg gaacctggac ggaggccgta actccaatgc tctcccggcc gtaagccata       60
agaccagtgt tcccc                                                        75
```

-continued

```
<210> SEQ ID NO 9
<211> LENGTH: 71
<212> TYPE: DNA
<213> ORGANISM: Artificial Sequence
<220> FEATURE:
<223> OTHER INFORMATION: Description of Artificial Sequence: SYNTHETIC
      OLIGONUCLEOTIDE COMPRISING GNRH CODING SEQUENCE
      AND  CLONING ENDS

<400> SEQUENCE: 9
gatccagagc actggtcata tggtctgcgt ccgggtgaac attggagcta cggtctacgc    60
cccggggatc c                                                        71

<210> SEQ ID NO 10
<211> LENGTH: 71
<212> TYPE: DNA
<213> ORGANISM: Artificial Sequence
<220> FEATURE:
<223> OTHER INFORMATION: Description of Artificial Sequence: SYNTHETIC
      OLIGONUCLEOTIDE COMPRISING GNRH CODING SEQUENCE
      AND  CLONING ENDS

<400> SEQUENCE: 10
tcgaggatcc ccggggcgta gaccgtagct ccaatgttca cccggacgca gaccatatga    60
ccagtgctct g                                                        71

<210> SEQ ID NO 11
<211> LENGTH: 68
<212> TYPE: DNA
<213> ORGANISM: Artificial Sequence
<220> FEATURE:
<223> OTHER INFORMATION: Description of Artificial Sequence: SYNTHETIC
      OLIGONUCLEOTIDE COMPRISING GNRH CODING SEQUENCE
      AND  CLONING ENDS

<400> SEQUENCE: 11
ggggaacact ggtcttatgg cttacggccg ggagagcatt ggagttacgg cctccgtcca    60
ggggatcc                                                            68

<210> SEQ ID NO 12
<211> LENGTH: 72
<212> TYPE: DNA
<213> ORGANISM: Artificial Sequence
<220> FEATURE:
<223> OTHER INFORMATION: Description of Artificial Sequence: SYNTHETIC
      OLIGONUCLEOTIDE COMPRISING GNRH CODING SEQUENCE
      AND  CLONING ENDS

<400> SEQUENCE: 12
tcgaggatcc cctggacgga ggccgtaact ccaatgctct cccggccgta agccataaga    60
ccagtgttcc cc                                                       72

<210> SEQ ID NO 13
<211> LENGTH: 10
<212> TYPE: PRT
<213> ORGANISM: GNRH AMINO ACID SEQUENCE

<400> SEQUENCE: 13

Glu His Trp Ser Tyr Gly Leu Arg Pro Gly
 1               5                  10

<210> SEQ ID NO 14
<211> LENGTH: 328
<212> TYPE: DNA
<213> ORGANISM: Artificial Sequence
```

-continued

<220> FEATURE:
<223> OTHER INFORMATION: Description of Artificial Sequence: part of
plasmid p9897-R

<400> SEQUENCE: 14
acgccagggt tttcccagtc acgacgttgt aaaacgacgg ccagtgagcg cgcgtaatac 60
gactcactat agggcgaatt ggagctccac cgcggtggcg gccgctctag aactagtgga 120
tccagagcac tggtcatatg gtctgcgtcc gggtgaacat tggagctacg gtctacgccc 180
cggggaacac tggtcttatg gcttacggcc gggagagcat tggagttacg gcctccgtcc 240
aggttccatg ggctcgaggg ggggcccggt acccagcttt tgttcccttt agtgagggtt 300
aattgcgcgc ttggcgtaat atggtcat 328

<210> SEQ ID NO 15
<211> LENGTH: 40
<212> TYPE: PRT
<213> ORGANISM: Artificial Sequence
<220> FEATURE:
<223> OTHER INFORMATION: Description of Artificial Sequence: GnRH
tetramer

<400> SEQUENCE: 15

Glu His Trp Ser Tyr Gly Leu Arg Pro Gly Glu His Trp Ser Tyr Gly
1 5 10 15

Leu Arg Pro Gly Glu His Trp Ser Tyr Gly Leu Arg Pro Gly Glu His
20 25 30

Trp Ser Tyr Gly Leu Arg Pro Gly
35 40

<210> SEQ ID NO 16
<211> LENGTH: 1259
<212> TYPE: DNA
<213> ORGANISM: Bovine herpesvirus 1
<220> FEATURE:
<221> NAME/KEY: gene
<222> LOCATION: (1)..(1259)
<223> OTHER INFORMATION: sequence encoding BHV-1 gD from clone
FlgD/Pots207(#79)

<400> SEQUENCE: 16
ccatggaggg gccgacattg gccgtgctgg gcgcgctgct cgccgttgcg gtaagcttgc 60
ctacacccgc gccgcgggtg acggtatacg tcgacccgcc ggcgtacccg atgccgcgat 120
acaactacac tgaacgctgg cacactaccg ggcccatacc gtcgcccttc gcagacggcc 180
gcgagcagcc cgtcgaggtg cgctacgcga cgagcgcggc ggcgtgcgac atgctggcgc 240
tgatcgcaga cccgcaggtg gggcgcacgc tgtgggaagc ggtacgccgg cacgcgcgcg 300
cgtacaacgc cacggtcata tggtacaaga tcgagagcgg gtgcgcccgg ccgctgtact 360
acatggagta caccgagtgc gagcccagga agcactttgg gtactgccgc taccgcacac 420
ccccgttttg ggacagcttc ctggcgggct tcgcctaccc cacggacgac gagctgggac 480
tgattatggc ggcgcccgcg cggctcgtcg agggccagta ccgacgcgcg ctgtacatcg 540
acggcacggt cgcctataca gatttcatgg tttcgctgcc ggccggggac tgctggttct 600
cgaaactcgg cgcggctcgc gggtacacct ttggcgcgtg cttcccggcc cgggattacg 660
agcaaaagaa ggttctgcgc ctgacgtatc tcacgcagta ctacccgcag gaggcacaca 720
aggccatagt cgactactgg ttcatgcgcc acgggggcgt cgttccgccg tattttgagg 780
agtcgaaggg ctacgagccg ccgcctgccg ccgatggggg ttcccccgcg ccacccggcg 840

-continued

```
acgacgaggc cgcgaggat gaaggggaga ccgaggacgg ggcagccggg cgggagggca    900
acggcggccc cccaggaccc gaaggcgacg gcgagagtca gaccccccgaa gccaacggag    960 gcgccgaggg cgagccgaaa cccggcccca gccccgacgc cgaccgcccc gaaggctggc    1020
cgagcctcga agccatcacg cacccccccgc cgcccccgc tacgcccgct cgagctccgg    1080
acgctgtttc ggtttctgtt ggtatcggta tcgctgctgc tgctatcgct tgcgttgctg    1140
ctgctgctgc tggtgcttac ttcgtttata ttcgtcgtcg tggtgctggt ccgctgccgc    1200
gtaaaccgaa aaaactgccg gctttcggta acgttaacta cagtgctctg ccgggttga    1259
```

<210> SEQ ID NO 17
<211> LENGTH: 418
<212> TYPE: PRT
<213> ORGANISM: Bovine herpesvirus 1
<220> FEATURE:
<221> NAME/KEY: PEPTIDE
<222> LOCATION: (1)..(418)
<223> OTHER INFORMATION: BHV-1gD enc -continued

```
Glu Thr Glu Asp Gly Ala Ala Gly Arg Glu Gly Asn Gly Gly Pro Pro
    290                 295                 300

Gly Pro Glu Gly Asp Gly Glu Ser Gln Thr Pro Glu Ala Asn Gly Gly
305                 310                 315                 320

Ala Glu Gly Glu Pro Lys Pro Gly Pro Ser Pro Asp Ala Asp Arg Pro
                325                 330                 335

Glu Gly Trp Pro Ser Leu Glu Ala Ile Thr His Pro Pro Pro Ala Pro
            340                 345                 350

Ala Thr Pro Ala Arg Ala Pro Asp Ala Val Ser Val Ser Val Gly Ile
        355                 360                 365

Gly Ile Ala Ala Ala Ala Ile Ala Cys Val Ala Ala Ala Ala Ala Gly
    370                 375                 380

Ala Tyr Phe Val Tyr Ile Arg Arg Arg Gly Ala Gly Pro Leu Pro Arg
385                 390                 395                 400

Lys Pro Lys Lys Leu Pro Ala Phe Gly Asn Val Asn Tyr Ser Ala Leu
                405                 410                 415

Pro Gly
```

<210> SEQ ID NO 18
<211> LENGTH: 1405
<212> TYPE: DNA
<213> ORGANISM: Bovine herpesvirus 1
<220> FEATURE:
<221> NAME/KEY: gene
<222> LOCATION: (1)..(1405)
<223> OTHER INFORMATION: BHV-1 gD from GenBank Accession No. M59846.

<400> SEQUENCE: 18

```
gggccgcagc cccggctggg tatatatccc cgacgggcga ctagagatac actcgccccg     60
cgcggctgct gcgagcgggc gaacatgcaa gggccgacat tggccgtgct gggcgcgctg    120
ctcgccgttg cggtgagctt gcctacaccc gcgccgcggg tgacggtata cgtcgacccg    180
ccggcgtacc cgatgccgcg atacaactac actgaacgct ggcacactac cgggcccata    240
ccgtcgccct tcgcagacgg ccgcgagcag cccgtcgagg tgcgctacgc gacgagcgcg    300
gcggcgtgcg acatgctggc gctgatcgca gacccgcagg tggggcgcac gctgtgggaa    360
gcggtacgcc ggcacgcgcg cgcgtacaac gccacggtca tatggtacaa gatcgagagc    420
gggtgcgccc ggccgctgta ctacatggag tacaccgagt gcgagcccag gaagcacttt    480
gggtactgcc gctaccgcac acccccgttt tgggacagct tcctggcggg cttcgcctac    540
cccacggacg acgagctggg actgattatg gcggcgcccg cgcggctcgt cgagggccag    600
taccgacgcg cgctgtacat cgacggcacg gtcgcctata cagatttcat ggtttcgctg    660
ccggccgggg actgctggtt ctcgaaactc ggcgcggctc gcgggtacac ctttggcgcg    720
tgcttcccgg cccgggatta cgagcaaaag aaggttctgc gcctgacgta tctcacgcag    780
tactacccgc aggaggcaca caaggccata gtcgactact ggttcatgcg ccacgggggc    840
gtcgttccgc cgtattttga ggagtcgaag ggctacgagc cgccgcctgc cgccgatggg    900 ggttccccccg cgccacccgg cgacgacgag gcccgcgagg atgaagggga gaccgaggac    960
ggggcagccg ggcgggaggg caacggcggc cccccaggac ccgaaggcga cggcgagagt   1020
cagacccccg aagccaacgg aggcgccgag ggcgagccga aacccggccc cagccccgac   1080
gccgaccgcc ccgaaggctg gccgagcctc gaagccatca cgcacccccc gcccgccccc   1140
gctacgcccg cggcccccga cgccgtgccg gtcagcgtcg ggatcggcat tgcggctgcg   1200
```

-continued

```
gcgatcgcgt gcgtggccgc cgccgccgcc ggcgcgtact tcgtctatac gcgccggcgc    1260
ggtgcgggtc cgctgcccag aaagccaaaa aagctgccgg cctttggcaa cgtcaactac    1320
agcgcgctgc ccgggtgagc ggcctaggcc ctcccccgac cgcccccttt gctcctagcc    1380
ccggctcctg ccgagccgcg cgggg                                          1405
```

<210> SEQ ID NO 19
<211> LENGTH: 417
<212> TYPE: PRT
<213> ORGANISM: Bovine herpesvirus 1
<220> FEATURE:
<221> NAME/KEY: PEPTIDE
<222> LOCATION: (1)..(417)
<223> OTHER INFORMATION: BHV-1 gD encoded by GenBank Accession No. M59846.

<400> SEQUENCE: 19

```
Met Gln Gly Pro Thr Leu Ala Val Leu Gly Ala Leu Leu Ala Val Ala
 1               5                  10                  15

Val Ser Leu Pro Thr Pro Ala Pro Arg Val Thr Val Tyr Val Asp Pro
                20                  25                  30

Pro Ala Tyr Pro Met Pro Arg Tyr Asn Tyr Thr Glu Arg Trp His Thr
            35                  40                  45

Thr Gly Pro Ile Pro Ser Pro Phe Ala Asp Gly Arg Glu Gln Pro Val
        50                  55                  60

Glu Val Arg Tyr Ala Thr Ser Ala Ala Ala Cys Asp Met Leu Ala Leu
 65                  70                  75                  80

Ile Ala Asp Pro Gln Val Gly Arg Thr Leu Trp Glu Ala Val Arg Arg
                85                  90                  95

His Ala Arg Ala Tyr Asn Ala Thr Val Ile Trp Tyr Lys Ile Glu Ser
            100                 105                 110

Gly Cys Ala Arg Pro Leu Tyr Tyr Met Glu Tyr Thr Glu Cys Glu Pro
        115                 120                 125

Arg Lys His Phe Gly Tyr Cys Arg Tyr Arg Thr Pro Pro Phe Trp Asp
    130                 135                 140

Ser Phe Leu Ala Gly Phe Ala Tyr Pro Thr Asp Asp Glu Leu Gly Leu
145                 150                 155                 160

Ile Met Ala Ala Pro Ala Arg Leu Val Glu Gly Gln Tyr Arg Arg Ala
                165                 170                 175

Leu Tyr Ile Asp Gly Thr Val Ala Tyr Thr Asp Phe Met Val Ser Leu
            180                 185                 190

Pro Ala Gly Asp Cys Trp Phe Ser Lys Leu Gly Ala Ala Arg Gly Tyr
        195                 200                 205

Thr Phe Gly Ala Cys Phe Pro Ala Arg Asp Tyr Glu Gln Lys Lys Val
    210                 215                 220

Leu Arg Leu Thr Tyr Leu Thr Gln Tyr Tyr Pro Gln Glu Ala His Lys
225                 230                 235                 240

Ala Ile Val Asp Tyr Trp Phe Met Arg His Gly Gly Val Val Pro Pro
                245                 250                 255

Tyr Phe Glu Glu Ser Lys Gly Tyr Glu Pro Pro Ala Ala Asp Gly
            260                 265                 270

Gly Ser Pro Ala Pro Gly Asp Asp Glu Ala Arg Glu Asp Glu Gly
        275                 280                 285

Glu Thr Glu Asp Gly Ala Ala Gly Arg Glu Gly Asn Gly Gly Pro Pro
    290                 295                 300

Gly Pro Glu Gly Asp Gly Glu Ser Gln Thr Pro Glu Ala Asn Gly Gly
```

```
                    305                 310                 315                 320
Ala Glu Gly Glu Pro Lys Pro Gly Pro Ser Pro Asp Ala Asp Arg Pro
                325                 330                 335

Glu Gly Trp Pro Ser Leu Glu Ala Ile Thr His Pro Pro Ala Pro
            340                 345                 350

Ala Thr Pro Ala Ala Pro Asp Ala Val Pro Val Ser Val Gly Ile Gly
                355                 360                 365

Ile Ala Ala Ala Ala Ile Ala Cys Val Ala Ala Ala Ala Gly Ala
            370                 375                 380

Tyr Phe Val Tyr Thr Arg Arg Gly Ala Gly Pro Leu Pro Arg Lys
385                 390                 395                 400

Pro Lys Lys Leu Pro Ala Phe Gly Asn Val Asn Tyr Ser Ala Leu Pro
                405                 410                 415

Gly

<210> SEQ ID NO 20
<211> LENGTH: 1218
<212> TYPE: DNA
<213> ORGANISM: Artificial Sequence
<220> FEATURE:
<223> OTHER INFORMATION: Description of Artificial Sequence: Sequence
      from pQE-tmgD encoding a tmgD.

<400> SEQUENCE: 20
ctcgagaaat cataaaaaat ttatttgctt tgtgagcgga taacaattat aatagattca      60
attgtgagcg gataacaatt tcacacagaa ttcattaaag aggagaaatt aactatgaga     120
ggatctcacc atcaccatca ccatacggat ccgcatgcca tgagcttgcc tacacccgcg     180
ccgcgggtga cggtatacgt cgacccgccg gcgtacccga tgccgcgata caactacact     240
gaacgctggc acactaccgg gcccataccg tcgcccttcg cagacggccg cgagcagccc     300
gtcgaggtgc gctacgcgac gagcgcggcg gcgtgcgaca tgctggcgct gatcgcagac     360
ccgcaggtgg ggcgcacgct gtgggaagcg tacgccggc acgcgcgcgc gtacaacgcc     420
acggtcatat ggtacaagat cgagagcggg tgcgcccggc cgctgtacta catggagtac     480
accgagtgcg agcccaggaa gcactttggg tactgccgct accgcacacc cccgttttgg     540
gacagcttcc tggcgggctt cgcctacccc acggacgacg agctgggact gattatggcg     600
gcgcccgcgc ggctcgtcga gggccagtac cgacgcgcgc tgtacatcga cggcacggtc     660
gcctatacag atttcatggt ttcgctgccg gccggggact gctggttctc gaaactcggc     720
gcggctcgcg ggtacacctt tggcgcgtgc ttcccggccc gggattacga gcaaaagaag     780
gttctgcgcc tgacgtatct cacgcagtac tacccgcagg aggcacacaa ggccatagtc     840
gactactggt tcatgcgcca cggggcgtc gttccgccgt attttgagga gtcgaagggc     900
tacgagccgc cgcctgccgc cgatgggggt tccccgcgc acccggcga cgacgaggcc     960 cgcgaggatg aagggagac cgaggacggg gcagccgggc gggagggcaa cggcggcccc    1020
ccaggacccg aaggcgacgg cgagagtcag accccgaag ccaacggagg cgccgagggc    1080
gagccgaaac ccggccccag ccccgacgcc gaccgccccg aaggctggcc gagcctcgaa    1140
gccatcacgc accccccgcc cgccccgctc acgcccgctc gagctcggta ccccgggtcg    1200
acctgcagcc aagcttaa                                                 1218

<210> SEQ ID NO 21
<211> LENGTH: 367
```

-continued

```
<212> TYPE: PRT
<213> ORGANISM: Artificial Sequence
<220> FEATURE:
<223> OTHER INFORMATION: Description of Artificial Sequence: tmgD
      encoded by pQE-tmgD.

<400> SEQUENCE: 21

Met Arg Gly Ser His His His His His His Thr Asp Pro His Ala Met
 1               5                  10                  15

Ser Leu Pro Thr Pro Ala Pro Arg Val Thr Val Tyr Val Asp Pro Pro
            20                  25                  30

Ala Tyr Pro Met Pro Arg Tyr Asn Tyr Thr Glu Arg Trp His Thr Thr
        35                  40                  45

Gly Pro Ile Pro Ser Pro Phe Ala Asp Gly Arg Glu Gln Pro Val Glu
    50                  55                  60

Val Arg Tyr Ala Thr Ser Ala Ala Cys Asp Met Leu Ala Leu Ile
65                  70                  75                  80

Ala Asp Pro Gln Val Gly Arg Thr Leu Trp Glu Ala Val Arg Arg His
                85                  90                  95

Ala Arg Ala Tyr Asn Ala Thr Val Ile Trp Tyr Lys Ile Glu Ser Gly
            100                 105                 110

Cys Ala Arg Pro Leu Tyr Tyr Met Glu Tyr Thr Glu Cys Glu Pro Arg
        115                 120                 125

Lys His Phe Gly Tyr Cys Arg Tyr Arg Thr Pro Pro Phe Trp Asp Ser
    130                 135                 140

Phe Leu Ala Gly Phe Ala Tyr Pro Thr Asp Asp Glu Leu Gly Leu Ile
145                 150                 155                 160

Met Ala Ala Pro Ala Arg Leu Val Glu Gly Gln Tyr Arg Arg Ala Leu
                165                 170                 175

Tyr Ile Asp Gly Thr Val Ala Tyr Thr Asp Phe Met Val Ser Leu Pro
            180                 185                 190

Ala Gly Asp Cys Trp Phe Ser Lys Leu Gly Ala Ala Arg Gly Tyr Thr
        195                 200                 205

Phe Gly Ala Cys Phe Pro Ala Arg Asp Tyr Glu Gln Lys Lys Val Leu
    210                 215                 220

Arg Leu Thr Tyr Leu Thr Gln Tyr Tyr Pro Gln Glu Ala His Lys Ala
225                 230                 235                 240

Ile Val Asp Tyr Trp Phe Met Arg His Gly Val Val Pro Pro Tyr
                245                 250                 255

Phe Glu Glu Ser Lys Gly Tyr Glu Pro Pro Ala Ala Asp Gly Gly
            260                 265                 270

Ser Pro Ala Pro Pro Gly Asp Asp Glu Ala Arg Glu Asp Glu Gly Glu
    275                 280                 285

Thr Glu Asp Gly Ala Ala Gly Arg Glu Gly Asn Gly Gly Pro Pro Gly
    290                 295                 300

Pro Glu Gly Asp Gly Glu Ser Gln Thr Pro Glu Ala Asn Gly Gly Ala
305                 310                 315                 320

Glu Gly Glu Pro Lys Pro Gly Pro Ser Pro Asp Ala Asp Arg Pro Glu
                325                 330                 335

Gly Trp Pro Ser Leu Glu Ala Ile Thr His Pro Pro Ala Pro Ala
            340                 345                 350

Thr Pro Ala Arg Ala Arg Tyr Pro Gly Ser Thr Cys Ser Gln Ala
        355                 360                 365

<210> SEQ ID NO 22
```

-continued

```
<211> LENGTH: 1360
<212> TYPE: DNA
<213> ORGANISM: Artificial Sequence
<220> FEATURE:
<223> OTHER INFORMATION: Description of Artificial Sequence: portion of
      pQE-GnRH:gD, including sequence encoding
      4GnRH-tmgD.

<400> SEQUENCE: 22
ctcgagaaat cataaaaaat ttatttgctt tgtgagcgga taacaattat aatagattca    60
attgtgagcg gataacaatt tcacacagaa ttcattaaag aggagaaatt aactatgaga   120
ggatctcacc atcaccatca ccatacggat ccgcatgcca tggatccaga gcactggtca   180
tatggtctgc gtccgggtga acattggagc tacggtctac gccccgggga acactggtct   240
tatggcttac ggccgggaga gcattggagt tacggcctcc gtccaggttc catgagcttg   300
cctacacccg cgccgcgggt gacggtatac gtcgacccgc cggcgtaccc gatgccgcga   360
tacaactaca ctgaacgctg gcacactacc gggcccatac cgtcgccctt cgcagacggc   420
cgcgagcagc ccgtcgaggt gcgctacgcg acgagcgcgg cggcgtgcga catgctggcg   480
ctgatcgcag acccgcaggt ggggcgcacg ctgtgggaag cggtacgccg gcacgcgcgc   540
gcgtacaacg ccacggtcat atggtacaag atcgagagcg ggtgcgcccg ccgctgtac    600 tacatggagt acaccgagtg cgagcccagg aagcactttg ggtactgccg ctaccgcaca   660
ccccgttttt gggacagctt cctggcgggc ttcgcctacc ccacggacga cgagctggga   720
ctgattatgg cggcgcccgc gcggctcgtc gagggccagt accgacgcgc gctgtacatc   780
gacggcacgg tcgcctatac agatttcatg gtttcgctgc cggccgggga ctgctggttc   840
tcgaaactcg gcgcggctcg cgggtacacc tttggcgcgt gcttcccggc ccgggattac   900
gagcaaaaga aggttctgcg cctgacgtat ctcacgcagt actaccgcca ggaggcacac   960
aaggccatag tcgactactg gttcatgcgc cacggggggcg tcgttccgcc gtattttgag  1020
gagtcgaagg gctacgagcc gccgcctgcc gccgatgggg gttccccggc gccacccggc  1080
gacgacgagg cccgcgagga tgaaggggag accgaggacg gggcagccgg gcgggagggc  1140
aacggcggcc ccccaggacc cgaaggcgac ggcgagagtc agaccccccga agccaacgga  1200 ggcgccgagg gcgagccgaa acccggcccc agccccgacg ccgaccgccc cgaaggctgg  1260
ccgagcctcg aagccatcac gcaccccccg cccgcccccg ctacgcccgc tcgagctcgg  1320
taccccgggt cgacctgcag ccaagcttaa ttagctgagc                        1360

<210> SEQ ID NO 23
<211> LENGTH: 411
<212> TYPE: PRT
<213> ORGANISM: Artificial Sequence
<220> FEATURE:
<223> OTHER INFORMATION: Description of Artificial Sequence: 4GnRH-tmgD
      encoded by pQE-GnRH:gD.

<400> SEQUENCE: 23

Met Arg Gly Ser His His His His His His Thr Asp Pro His Ala Met
 1               5                  10                  15

Asp Pro Glu His Trp Ser Tyr Gly Leu Arg Pro Gly Glu His Trp Ser
            20                  25                  30

Tyr Gly Leu Arg Pro Gly Glu His Trp Ser Tyr Gly Leu Arg Pro Gly
        35                  40                  45

Glu His Trp Ser Tyr Gly Leu Arg Pro Gly Ser Met Ser Leu Pro Thr
    50                  55                  60
```

```
Pro Ala Pro Arg Val Thr Val Tyr Val Asp Pro Pro Ala Tyr Pro Met
 65                  70                  75                  80

Pro Arg Tyr Asn Tyr Thr Glu Arg Trp His Thr Thr Gly Pro Ile Pro
             85                  90                  95

Ser Pro Phe Ala Asp Gly Arg Glu Gln Pro Val Glu Val Arg Tyr Ala
            100                 105                 110

Thr Ser Ala Ala Ala Cys Asp Met Leu Ala Leu Ile Ala Asp Pro Gln
            115                 120                 125

Val Gly Arg Thr Leu Trp Glu Ala Val Arg Arg His Ala Arg Ala Tyr
        130                 135                 140

Asn Ala Thr Val Ile Trp Tyr Lys Ile Glu Ser Gly Cys Ala Arg Pro
145                 150                 155                 160

Leu Tyr Tyr Met Glu Tyr Thr Glu Cys Glu Pro Arg Lys His Phe Gly
                165                 170                 175

Tyr Cys Arg Tyr Arg Thr Pro Pro Phe Trp Asp Ser Phe Leu Ala Gly
            180                 185                 190

Phe Ala Tyr Pro Thr Asp Asp Glu Leu Gly Leu Ile Met Ala Ala Pro
        195                 200                 205

Ala Arg Leu Val Glu Gly Gln Tyr Arg Arg Ala Leu Tyr Ile Asp Gly
    210                 215                 220

Thr Val Ala Tyr Thr Asp Phe Met Val Ser Leu Pro Ala Gly Asp Cys
225                 230                 235                 240

Trp Phe Ser Lys Leu Gly Ala Ala Arg Gly Tyr Thr Phe Gly Ala Cys
                245                 250                 255

Phe Pro Ala Arg Asp Tyr Glu Gln Lys Lys Val Leu Arg Leu Thr Tyr
            260                 265                 270

Leu Thr Gln Tyr Tyr Pro Gln Glu Ala His Lys Ala Ile Val Asp Tyr
        275                 280                 285

Trp Phe Met Arg His Gly Gly Val Val Pro Pro Tyr Phe Glu Glu Ser
    290                 295                 300

Lys Gly Tyr Glu Pro Pro Ala Ala Asp Gly Gly Ser Pro Ala Pro
305                 310                 315                 320

Pro Gly Asp Asp Glu Ala Arg Glu Asp Glu Gly Glu Thr Glu Asp Gly
                325                 330                 335

Ala Ala Gly Arg Glu Gly Asn Gly Gly Pro Gly Pro Glu Gly Asp
            340                 345                 350

Gly Glu Ser Gln Thr Pro Glu Ala Asn Gly Gly Ala Glu Gly Glu Pro
        355                 360                 365

Lys Pro Gly Pro Ser Pro Asp Ala Asp Arg Pro Glu Gly Trp Pro Ser
    370                 375                 380

Leu Glu Ala Ile Thr His Pro Pro Ala Pro Ala Thr Pro Ala Arg
385                 390                 395                 400

Ala Arg Tyr Pro Gly Ser Thr Cys Ser Gln Ala
                405                 410

<210> SEQ ID NO 24
<211> LENGTH: 1360
<212> TYPE: DNA
<213> ORGANISM: Artificial Sequence
<220> FEATURE:
<223> OTHER INFORMATION: Description of Artificial Sequence: portion of
      pQE-gD:GnRH, including sequence coding tmgD-4GnRH.

<400> SEQUENCE: 24
ctcgagaaat cataaaaaat ttatttgctt tgtgagcgga taacaattat aatagattca   60
```

-continued

```
attgtgagcg gataacaatt tcacacagaa ttcattaaag aggagaaatt aactatgaga    120
ggatctcacc atcaccatca ccatacggat ccgcatgcca tgagcttgcc tacacccgcg    180
ccgcgggtga cggtatacgt cgacccgccg gcgtacccga tgccgcgata caactacact    240
gaacgctgga cactaccggg cccataccg tcgcccttcg cagacggccg cgagcagccc    300
gtcgaggtgc gctacgcgac gagcgcggcg gcgtgcgaca tgctggcgct gatcgcagac    360
ccgcaggtgg ggcgcacgct gtgggaagcg gtacgccggc acgcgcgcgc gtacaacgcc    420
acggtcatat ggtacaagat cgagagcggg tgcgcccggc cgctgtacta catggagtac    480
accgagtgcg agcccaggaa gcactttggg tactgccgct accgcacacc cccgttttgg    540
gacagcttcc tggcgggctt cgcctacccc acggacgacg agctgggact gattatggcg    600
gcgcccgcgc ggctcgtcga gggccagtac cgacgcgcgc tgtacatcga cggcacggtc    660
gcctatacag atttcatggt ttcgctgccg gccggggact gctggttctc gaaactcggc    720
gcggctcgcg ggtacacctt tggcgcgtgc ttcccggccc gggattacga gcaaaagaag    780
gttctgcgcc tgacgtatct cacgcagtac tacccgcagg aggcacacaa ggccatagtc    840
gactactggt tcatgcgcca cggggggcgtc gttccgccgt attttgagga gtcgaagggc    900
tacgagccgc cgcctgccgc cgatgggggt tcccccgcgc cacccggcga cgacgaggcc    960
cgcgaggatg aaggggagac cgaggacggg gcagccgggc ggggagggcaa cggcggcccc   1020
ccaggacccg aaggcgacgg cgagagtcag accccccgaag ccaacggagg cgccgagggc   1080
gagccgaaac ccggccccag ccccgacgcc gaccgccccg aaggctggcc gagcctcgaa   1140
gccatcacgc acccccccgcc cgcccccgct acgcccgctc gagctccaga gcactggtca   1200
tatggtctgc gtccgggtga acattggagc tacggtctac gccccgggga acactggtct   1260
tatggcttac ggccgggaga gcattggagt tacggcctcc gtccaggttg aagcttaatt   1320
agctgagctt ggactcctgt tgatagatcc agtaatgacc                         1360
```

<210> SEQ ID NO 25
<211> LENGTH: 398
<212> TYPE: PRT
<213> ORGANISM: Artificial Sequence
<220> FEATURE:
<223> OTHER INFORMATION: Description of Artificial Sequence: tmgD-4GmRH
      encoded by pQE-gD:GnRH.

<400> SEQUENCE: 25

```
Met Arg Gly Ser His His His His His His Thr Asp Pro His Ala Met
 1               5                  10                  15

Ser Leu Pro Thr Pro Ala Pro Arg Val Thr Val Tyr Val Asp Pro Pro
            20                  25                  30

Ala Tyr Pro Met Pro Arg Tyr Asn Tyr Thr Glu Arg Trp His Thr Thr
        35                  40                  45

Gly Pro Ile Pro Ser Pro Phe Ala Asp Gly Arg Glu Gln Pro Val Glu
    50                  55                  60

Val Arg Tyr Ala Thr Ser Ala Ala Ala Cys Asp Met Leu Ala Leu Ile
65                  70                  75                  80

Ala Asp Pro Gln Val Gly Arg Thr Leu Trp Glu Ala Val Arg Arg His
                85                  90                  95

Ala Arg Ala Tyr Asn Ala Thr Val Ile Trp Tyr Lys Ile Glu Ser Gly
            100                 105                 110

Cys Ala Arg Pro Leu Tyr Tyr Met Glu Tyr Thr Glu Cys Glu Pro Arg
        115                 120                 125
```

```
Lys His Phe Gly Tyr Cys Arg Tyr Arg Thr Pro Pro Phe Trp Asp Ser
        130                 135                 140

Phe Leu Ala Gly Phe Ala Tyr Pro Thr Asp Asp Glu Leu Gly Leu Ile
145                 150                 155                 160

Met Ala Ala Pro Ala Arg Leu Val Glu Gly Gln Tyr Arg Arg Ala Leu
                165                 170                 175

Tyr Ile Asp Gly Thr Val Ala Tyr Thr Asp Phe Met Val Ser Leu Pro
            180                 185                 190

Ala Gly Asp Cys Trp Phe Ser Lys Leu Gly Ala Ala Arg Gly Tyr Thr
        195                 200                 205

Phe Gly Ala Cys Phe Pro Ala Arg Asp Tyr Glu Gln Lys Lys Val Leu
210                 215                 220

Arg Leu Thr Tyr Leu Thr Gln Tyr Tyr Pro Gln Glu Ala His Lys Ala
225                 230                 235                 240

Ile Val Asp Tyr Trp Phe Met Arg His Gly Val Val Pro Pro Tyr
            245                 250                 255

Phe Glu Glu Ser Lys Gly Tyr Glu Pro Pro Ala Ala Asp Gly Gly
                260                 265                 270

Ser Pro Ala Pro Pro Gly Asp Asp Glu Ala Arg Glu Asp Gly Glu
        275                 280                 285

Thr Glu Asp Gly Ala Ala Gly Arg Glu Gly Asn Gly Gly Pro Pro Gly
290                 295                 300

Pro Glu Gly Asp Gly Glu Ser Gln Thr Pro Glu Ala Asn Gly Gly Ala
305                 310                 315                 320

Glu Gly Glu Pro Lys Pro Gly Pro Ser Pro Asp Ala Asp Arg Pro Glu
                325                 330                 335

Gly Trp Pro Ser Leu Glu Ala Ile Thr His Pro Pro Ala Pro Ala
            340                 345                 350

Thr Pro Ala Arg Ala Pro Glu His Trp Ser Tyr Gly Leu Arg Pro Gly
                355                 360                 365

Glu His Trp Ser Tyr Gly Leu Arg Pro Gly Glu His Trp Ser Tyr Gly
    370                 375                 380

Leu Arg Pro Gly Glu His Trp Ser Tyr Gly Leu Arg Pro Gly
385                 390                 395

<210> SEQ ID NO 26
<211> LENGTH: 1441
<212> TYPE: DNA
<213> ORGANISM: Artificial Sequence
<220> FEATURE:
<223> OTHER INFORMATION: Description of Artificial Sequence: portion of
      pQE-GnRH:gD:GnRH, including encoding
      4GnRH-tmgD-4GnRH

<400> SEQUENCE: 26
ctcgagaaat cataaaaaat ttatttgctt tgtgagcgga taacaattat aatagattca      60
attgtgagcg gataacaatt tcacacagaa ttcattaaag aggagaaatt aactatgaga     120
ggatctcacc atcaccatca ccatacggat ccgcatgcca tggatccaga gcactggtca     180
tatggtctgc gtccgggtga acattggagc tacggtctac gccccgggga acactggtct     240
tatggcttac ggccgggaga gcattggagt tacggcctcc gtccaggttc catgagcttg     300
cctacacccg cgccgcgggt gacggtatac gtcgacccgc cggcgtaccc gatgccgcga     360
tacaactaca ctgaacgctg gcacactacc gggcccatac cgtcgccctt cgcagacggc     420
cgcgagcagc ccgtcgaggt gcgctacgcg acgagcgcgg cggcgtgcga catgctggcg     480
```

```
ctgatcgcag acccgcaggt ggggcgcacg ctgtgggaag cggtacgccg gcacgcgcgc    540
gcgtacaacg ccacggtcat atggtacaag atcgagagcg ggtgcgcccg gccgctgtac    600
tacatggagt acaccgagtg cgagcccagg aagcactttg gtactgccg ctaccgcaca     660 cccccgtttt gggacagctt cctggcgggc ttcgcctacc ccacggacga cgagctggga    720
ctgattatgg cggcgcccgc gcggctcgtc gagggccagt accgacgcgc gctgtacatc    780
gacggcacgg tcgcctatac agatttcatg gtttcgctgc cggccgggga ctgctggttc    840
tcgaaactcg gcgcggctcg cgggtacacc tttggcgcgt gcttcccggc ccgggattac    900
gagcaaaaga aggttctgcg cctgacgtat ctcacgcagt actacccgca ggaggcacac    960
aaggccatag tcgactactg gttcatgcgc cacggggcg tcgttccgcc gtattttgag     1020
gagtcgaagg gctacgagcc gccgcctgcc gccgatgggg gttcccccgc gccacccggc    1080
gacgacgagg cccgcgagga tgaaggggag accgaggacg gggcagccgg gcgggagggc    1140
aacggcggcc ccccaggacc cgaaggcgac ggcgagagtc agaccccga agccaacgga    1200 ggcgccgagg gcgagccgaa acccggcccc agccccgacg ccgaccgccc cgaaggctgg    1260
ccgagcctcg aagccatcac gcaccccccg cccgcccccg ctacgcccgc tcgagctcca    1320
gagcactggt catatggtct gcgtccgggt gaacattgga gctacggtct acgccccggg    1380
gaacactggt cttatggctt acggccggga gagcattgga gttacggcct ccgtccaggt    1440
t                                                                   1441
```

<210> SEQ ID NO 27
<211> LENGTH: 442
<212> TYPE: PRT
<213> ORGANISM: Artificial Sequence
<220> FEATURE:
<223> OTHER INFORMATION: Description of Artificial Sequence:
      4GnRH-tmgD-4GnRH encoded by pQE-GnRH:gD:GnRH

<400> SEQUENCE: 27

```
Met Arg Gly Ser His His His His His His Thr Asp Pro His Ala Met
 1               5                  10                  15

Asp Pro Glu His Trp Ser Tyr Gly Leu Arg Pro Gly Glu His Trp Ser
             20                  25                  30

Tyr Gly Leu Arg Pro Gly Glu His Trp Ser Tyr Gly Leu Arg Pro Gly
         35                  40                  45

Glu His Trp Ser Tyr Gly Leu Arg Pro Gly Ser Met Ser Leu Pro Thr
     50                  55                  60

Pro Ala Pro Arg Val Thr Val Tyr Val Asp Pro Ala Tyr Pro Met
65                  70                  75                  80

Pro Arg Tyr Asn Tyr Thr Glu Arg Trp His Thr Thr Gly Pro Ile Pro
                 85                  90                  95

Ser Pro Phe Ala Asp Gly Arg Glu Gln Pro Val Glu Val Arg Tyr Ala
            100                 105                 110

Thr Ser Ala Ala Ala Cys Asp Met Leu Ala Leu Ile Ala Asp Pro Gln
        115                 120                 125

Val Gly Arg Thr Leu Trp Glu Ala Val Arg Arg His Ala Arg Ala Tyr
    130                 135                 140

Asn Ala Thr Val Ile Trp Tyr Lys Ile Glu Ser Gly Cys Ala Arg Pro
145                 150                 155                 160

Leu Tyr Tyr Met Glu Tyr Thr Glu Cys Glu Pro Arg Lys His Phe Gly
                165                 170                 175

Tyr Cys Arg Tyr Arg Thr Pro Pro Phe Trp Asp Ser Phe Leu Ala Gly
```

-continued

```
                      180                 185                 190
            Phe Ala Tyr Pro Thr Asp Asp Glu Leu Gly Leu Ile Met Ala Ala Pro
                195                 200                 205

Ala Arg Leu Val Glu Gly Gln Tyr Arg Arg Ala Leu Tyr Ile Asp Gly
            210                 215                 220

Thr Val Ala Tyr Thr Asp Phe Met Val Ser Leu Pro Ala Gly Asp Cys
            225                 230                 235                 240

Trp Phe Ser Lys Leu Gly Ala Ala Arg Gly Tyr Thr Phe Gly Ala Cys
                            245                 250                 255

Phe Pro Ala Arg Asp Tyr Glu Gln Lys Lys Val Leu Arg Leu Thr Tyr
                        260                 265                 270

Leu Thr Gln Tyr Tyr Pro Gln Glu Ala His Lys Ala Ile Val Asp Tyr
                    275                 280                 285

Trp Phe Met Arg His Gly Gly Val Val Pro Pro Tyr Phe Glu Glu Ser
                290                 295                 300

Lys Gly Tyr Glu Pro Pro Ala Ala Asp Gly Gly Ser Pro Ala Pro
            305                 310                 315                 320

Pro Gly Asp Asp Glu Ala Arg Glu Asp Glu Gly Glu Thr Glu Asp Gly
                            325                 330                 335

Ala Ala Gly Arg Glu Gly Asn Gly Gly Pro Gly Pro Glu Gly Asp
                        340                 345                 350

Gly Glu Ser Gln Thr Pro Glu Ala Asn Gly Gly Ala Glu Gly Pro
                    355                 360                 365

Lys Pro Gly Pro Ser Pro Asp Ala Asp Arg Pro Glu Gly Trp Pro Ser
                370                 375                 380

Leu Glu Ala Ile Thr His Pro Pro Ala Pro Ala Thr Pro Ala Arg
            385                 390                 395                 400

Ala Pro Glu His Trp Ser Tyr Gly Leu Arg Pro Gly Glu His Trp Ser
                            405                 410                 415

Tyr Gly Leu Arg Pro Gly Glu His Trp Ser Tyr Gly Leu Arg Pro Gly
                        420                 425                 430

Glu His Trp Ser Tyr Gly Leu Arg Pro Gly
                    435                 440

<210> SEQ ID NO 28
<211> LENGTH: 1079
<212> TYPE: DNA
<213> ORGANISM: Artificial Sequence
<220> FEATURE:
<223> OTHER INFORMATION: Description of Artificial Sequence: portion of
      pCMV-tgD, including sequence encoding a truncated
      gD

<400> SEQUENCE: 28
gatatcatgc agggccgac attggccgtg ctgggcgcgc tgctcgccgt tgcggtaagc        60
ttgcctacac ccgcgccgcg ggtgacggta tacgtcgacc cgccggcgta cccgatgccg      120
cgatacaact acactgaacg ctggcacact accgggccca taccgtcgcc cttcgcagac      180
ggccgcgagc agcccgtcga ggtgcgctac gcgacgagcg cggcggcgtg cgacatgctg      240
gcgctgatcg cagacccgca ggtggggcgc acgctgtggg aagcggtacg ccggcacgcg      300
cgcgcgtaca cgccacggt catatggtac aagatcgaga gcgggtgcgc ccggccgctg      360
tactacatgg agtacaccga gtgcgagccc aggaagcact ttgggtactg ccgctaccgc      420 acaccccgt tttgggacag cttcctggcg ggcttcgcct accccacgga cgacgagctg      480
ggactgatta tggcggcgcc cgcgcggctc gtcgagggcc agtaccgacg cgcgctgtac      540
```

```
atcgacggca cggtcgccta tacagatttc atggtttcgc tgccggccgg ggactgctgg      600
ttctcgaaac tcggcgcggc tcgcgggtac acctttggcg cgtgcttccc ggcccgggat      660
tacgagcaaa agaaggttct gcgcctgacg tatctcacgc agtactaccc gcaggaggca      720
cacaaggcca tagtcgacta ctggttcatg cgccacgggg gcgtcgttcc gccgtatttt      780
gaggagtcga agggctacga gccgccgcct gccgccgatg ggggttcccc cgcgccaccc      840
ggcgacgacg aggcccgcga ggatgaaggg gagaccgagg acggggcagc cgggcgggag      900
ggcaacggcg gccccccagg acccgaaggc gacggcgaga gtcagacccc cgaagccaac      960
ggaggcgccg agggcgagcc gaaacccggc cccagccccg acgccgaccg ccccgaggct     1020
ggccgagcct cgaagccatc acgcaccccc cgcccgcccc cgctacgccc tgaggtacc     1079
```

<210> SEQ ID NO 29
<211> LENGTH: 353
<212> TYPE: PRT
<213> ORGANISM: Artificial Sequence
<220> FEATURE:
<223> OTHER INFORMATION: Description of Artificial Sequence: truncated
      gD encoded by pCMV-tgD

<400> SEQUENCE: 29

```
Met Gln Gly Pro Thr Leu Ala Val Leu Gly Ala Leu Leu Ala Val Ser
 1               5                  10                  15

Leu Pro Thr Pro Ala Pro Arg Val Thr Val Tyr Val Asp Pro Pro Ala
             20                  25                  30

Tyr Pro Met Pro Arg Tyr Asn Tyr Thr Glu Arg Trp His Thr Thr Gly
         35                  40                  45

Pro Ile Pro Ser Pro Phe Ala Asp Gly Arg Glu Gln Pro Val Glu Val
     50                  55                  60

Arg Tyr Ala Thr Ser Ala Ala Ala Cys Asp Met Leu Ala Leu Ile Ala
 65                  70                  75                  80

Asp Pro Gln Val Gly Arg Thr Leu Trp Glu Ala Val Arg Arg His Ala
                 85                  90                  95

Arg Ala Tyr Asn Ala Thr Val Ile Trp Tyr Lys Ile Glu Ser Gly Cys
            100                 105                 110

Ala Arg Pro Leu Tyr Tyr Met Glu Tyr Thr Glu Cys Glu Pro Arg Lys
        115                 120                 125

His Phe Gly Tyr Cys Arg Tyr Arg Thr Pro Pro Phe Trp Asp Ser Phe
    130                 135                 140

Leu Ala Gly Phe Ala Tyr Pro Thr Asp Asp Glu Leu Gly Leu Ile Met
145                 150                 155                 160

Ala Ala Pro Ala Arg Leu Val Glu Gly Gln Tyr Arg Arg Ala Leu Tyr
                165                 170                 175

Ile Asp Gly Thr Val Ala Tyr Thr Asp Phe Met Val Ser Leu Pro Ala
            180                 185                 190

Gly Asp Cys Trp Phe Ser Lys Leu Gly Ala Ala Arg Gly Tyr Thr Phe
        195                 200                 205

Gly Ala Cys Phe Pro Ala Arg Asp Tyr Glu Gln Lys Lys Val Leu Arg
    210                 215                 220

Leu Thr Tyr Leu Thr Gln Tyr Tyr Pro Gln Glu Ala His Lys Ala Ile
225                 230                 235                 240

Val Asp Tyr Trp Phe Met Arg His Gly Gly Val Val Pro Pro Tyr Phe
                245                 250                 255

Glu Glu Ser Lys Gly Tyr Glu Pro Pro Pro Ala Ala Asp Gly Gly Ser
```

```
                    260              265              270
Pro Ala Pro Pro Gly Asp Asp Glu Ala Arg Glu Asp Glu Gly Glu Thr
                275              280              285
Glu Asp Gly Ala Ala Gly Arg Glu Gly Asn Gly Gly Pro Pro Gly Pro
            290              295              300
Glu Gly Asp Gly Glu Ser Gln Thr Pro Glu Ala Asn Gly Gly Ala Glu
305              310              315              320
Gly Glu Pro Lys Pro Gly Pro Ser Pro Asp Ala Asp Arg Pro Glu Gly
                325              330              335
Trp Pro Ser Leu Glu Ala Ile Thr His Pro Pro Ala Pro Ala Thr
            340              345              350
Pro
```

```
<210> SEQ ID NO 30
<211> LENGTH: 1241
<212> TYPE: DNA
<213> ORGANISM: Artificial Sequence
<220> FEATURE:
<223> OTHER INFORMATION: Description of Artificial Sequence: portion of
      pCMV-gD:GnRH, including sequence encoding a
      tgD-4GnRH fusion protein

<400> SEQUENCE: 30
gcggccgcaa gatatcatgc aggggccgac attggccgtg ctgggcgcgc tgctcgccgt      60
tgcggtaagc ttgcctacac ccgcgccgcg ggtgacggta tacgtcgacc cgccggcgta     120
cccgatgccg cgatacaact acactgaacg ctggcacact accgggccca taccgtcgcc     180
cttcgcagac ggccgcgagc agcccgtcga ggtgcgctac gcgacgagcg cggcggcgtg     240
cgacatgctg cgcgctgatc gcagacccgc agtggggcgc acgctgtggg aagcggtacg     300
ccggcacgcg cgcgcgtaca acgccacggt catatggtac aagatcgaga gcgggtgcgc     360
ccggccgctg tactacatgg agtacaccga gtgcgagccc aggaagcact ttgggtactg     420
ccgctaccgc acaccccgt tttgggacag cttcctggcg gcttcgcct accccacgga      480 cgacgagctg ggactgatta tggcggcgcc cgcgcggctc gtcgagggcc agtaccgacg     540
cgcgctgtac atcgacggca cggtcgccta tacagatttc atggtttcgc tgccggccgg     600
ggactgctgt ttctcgaaac tcggcgcggc tcgcgggtac acctttggcg cgtgcttccc     660
ggcccgggat tacgagcaaa agaaggttct cgcctgacg tatctcacgc agtactaccc      720
gcaggaggca cacaaggcca tagtcgacta ctggttcatg cgccacgggg gcgtcgttcc     780
gccgtatttt gaggagtcga aggctacga gccgccgcct gccgccgatg ggggttcccc      840
cgcgccaccc ggcgacgacg aggcccgcga ggatgaaggg gagaccgagg acggggcagc     900
cgggcgggag ggcaacggcg gccccccagg acccgaaggc gacggcgaga gtcagacccc     960
cgaagccaac ggaggcgccg agggcgagcc gaaacccggc cccagccccg acgccgaccg    1020
ccccgaaggc tggccgagcc tcgaagccat cacgcacccc ccgccgccc cgctacgcc      1080 cgctcgagct ccagagcact ggtcatatgg tctgcgtccg ggtgaacatt ggagctacgg    1140
tctacgcccc ggggaacact ggtcttatgg cttacggccg ggagagcatt ggagttacgg    1200
cctccgtcca ggttgaagct gggatactag tgagcggccg c                        1241

<210> SEQ ID NO 31
<211> LENGTH: 397
<212> TYPE: PRT
<213> ORGANISM: Artificial Sequence
<220> FEATURE:
```

<223> OTHER INFORMATION: Description of Artificial Sequence: tgD-4GnRH
       fusion protein encoded by pCMV-gD:GnRH

<400> SEQUENCE: 31

```
Met Gln Gly Pro Thr Leu Ala Val Leu Gly Ala Leu Leu Ala Val Ser
 1               5                  10                  15

Leu Pro Thr Pro Ala Pro Arg Val Thr Val Tyr Val Asp Pro Pro Ala
             20                  25                  30

Tyr Pro Met Pro Arg Tyr Asn Tyr Thr Glu Arg Trp His Thr Thr Gly
         35                  40                  45

Pro Ile Pro Ser Pro Phe Ala Asp Gly Arg Glu Gln Pro Val Glu Val
     50                  55                  60

Arg Tyr Ala Thr Ser Ala Ala Cys Asp Met Leu Ala Leu Ile Ala
 65              70                  75                  80

Asp Pro Gln Val Gly Arg Thr Leu Trp Glu Ala Val Arg Arg His Ala
             85                  90                  95

Arg Ala Tyr Asn Ala Thr Val Ile Trp Tyr Lys Ile Glu Ser Gly Cys
        100                 105                 110

Ala Arg Pro Leu Tyr Tyr Met Glu Tyr Thr Glu Cys Glu Pro Arg Lys
    115                 120                 125

His Phe Gly Tyr Cys Arg Tyr Arg Thr Pro Pro Phe Trp Asp Ser Phe
130                 135                 140

Leu Ala Gly Phe Ala Tyr Pro Thr Asp Asp Glu Leu Gly Leu Ile Met
145                 150                 155                 160

Ala Ala Pro Ala Arg Leu Val Glu Gly Gln Tyr Arg Arg Ala Leu Tyr
                165                 170                 175

Ile Asp Gly Thr Val Ala Tyr Thr Asp Phe Met Val Ser Leu Pro Ala
            180                 185                 190

Gly Asp Cys Trp Phe Ser Lys Leu Gly Ala Ala Arg Gly Tyr Thr Phe
        195                 200                 205

Gly Ala Cys Phe Pro Ala Arg Asp Tyr Glu Gln Lys Val Leu Arg
    210                 215                 220

Leu Thr Tyr Leu Thr Gln Tyr Tyr Pro Gln Glu Ala His Lys Ala Ile
225                 230                 235                 240

Val Asp Tyr Trp Phe Met Arg His Gly Val Val Pro Pro Tyr Phe
                245                 250                 255

Glu Glu Ser Lys Gly Tyr Glu Pro Pro Ala Ala Asp Gly Gly Ser
                260                 265                 270

Pro Ala Pro Pro Gly Asp Asp Glu Ala Arg Glu Asp Glu Gly Glu Thr
            275                 280                 285

Glu Asp Gly Ala Ala Gly Arg Glu Gly Asn Gly Pro Pro Gly Pro
        290                 295                 300

Glu Gly Asp Gly Glu Ser Gln Thr Pro Glu Ala Asn Gly Gly Ala Glu
305                 310                 315                 320

Gly Glu Pro Lys Pro Gly Pro Ser Pro Asp Ala Asp Arg Pro Glu Gly
                325                 330                 335

Trp Pro Ser Leu Glu Ala Ile Thr His Pro Pro Ala Pro Ala Thr
            340                 345                 350

Pro Ala Arg Ala Pro Glu His Trp Ser Tyr Gly Leu Arg Pro Gly Glu
        355                 360                 365

His Trp Ser Tyr Gly Leu Arg Pro Gly Glu His Trp Ser Tyr Gly Leu
    370                 375                 380

Arg Pro Gly Glu His Trp Ser Tyr Gly Leu Arg Pro Gly
385                 390                 395
```

<210> SEQ ID NO 32
<211> LENGTH: 120
<212> TYPE: DNA
<213> ORGANISM: Artificial Sequence
<220> FEATURE:
<223> OTHER INFORMATION: Description of Artificial Sequence: sequence encoding a GnRH tetramer

<400> SEQUENCE: 32

| | | | | | |
|---|---|---|---|---|---|
| gagcactggt | catatggtct | gcgtccgggt | gaacattgga | gctacggtct | acgccccggg | 60 |
| gaacactggt | cttatggctt | acggccggga | gagcattgga | gttacggcct | ccgtccaggt | 120 |

<210> SEQ ID NO 33
<211> LENGTH: 30
<212> TYPE: DNA
<213> ORGANISM: Artificial Sequence
<220> FEATURE:
<223> OTHER INFORMATION: Description of Artificial Sequence: sequence encoding a GnRH monomer

<400> SEQUENCE: 33
gagcactggt catatggtct gcgtccgggt          30

<210> SEQ ID NO 34
<211> LENGTH: 1179
<212> TYPE: DNA
<213> ORGANISM: Artificial Sequence
<220> FEATURE:
<223> OTHER INFORMATION: Description of Artificial Sequence: sequence encoding a 4GnRH-tmgD fusion protein

<400> SEQUENCE: 34

| | | | | | |
|---|---|---|---|---|---|
| gagcactggt | catatggtct | gcgtccgggt | gaacattgga | gctacggtct | acgccccggg | 60 |
| gaacactggt | cttatggctt | acggccggga | gagcattgga | gttacggcct | ccgtccaggt | 120 |
| tccatgagct | tgcctacacc | cgcgccgcgg | gtgacggtat | acgtcgaccc | gccggcgtac | 180 |
| ccgatgccgc | gatacaacta | cactgaacgc | tggcacacta | ccgggcccat | accgtcgccc | 240 |
| ttcgcagacg | gccgcgagca | gcccgtcgag | gtgcgctacg | cgacgagcgc | ggcggcgtgc | 300 |
| gacatgctgg | cgctgatcgc | agacccgcag | gtggggcgca | cgctgtggga | agcggtacgc | 360 |
| cggcacgcgc | gcgcgtacaa | cgccacggtc | atatggtaca | agatcgagag | cgggtgcgcc | 420 |
| cggccgctgt | actacatgga | gtacaccgag | tgcgagccca | ggaagcactt | tgggtactgc | 480 |
| cgctaccgca | caccccgtt | ttgggacagc | ttcctggcgg | gcttcgccta | ccccacggac | 540 |
| gacgagctgg | gactgattat | ggcggcgccc | gcgcggctcg | tcgagggcca | gtaccgacgc | 600 |
| gcgctgtaca | tcgacggcac | ggtcgcctat | acagatttca | tggtttcgct | gccggccggg | 660 |
| gactgctggt | tctcgaaact | cggcgcggct | cgcgggtaca | cctttggcgc | gtgcttcccg | 720 |
| gcccgggatt | acgagcaaaa | gaaggttctg | cgcctgacgt | atctcacgca | gtactacccg | 780 |
| caggaggcac | acaaggccat | agtcgactac | tggttcatgc | gccacggggg | cgtcgttccg | 840 |
| ccgtattttg | aggagtcgaa | gggctacgag | ccgccgcctg | ccgccgatgg | gggttccccc | 900 |
| gcgccacccg | gcgacgacga | ggcccgcgag | gatgaagggg | agaccgagga | cggggcagcc | 960 |
| gggcgggagg | gcaacggcgg | ccccccagga | cccgaaggcg | acggcgagag | tcagaccccc | 1020 |
| gaagccaacg | gaggcgccga | gggcgagccg | aaacccggcc | ccagccccga | cgccgaccgc | 1080 |
| cccgaaggct | ggccgagcct | cgaagccatc | acgcacccccc | cgcccgcccc | cgctacgccc | 1140 |
| gctcgagctc | ggtaccccgg | gtcgacctgc | agccaagct | | | 1179 |

<210> SEQ ID NO 35
<211> LENGTH: 340
<212> TYPE: PRT
<213> ORGANISM: Artificial Sequence
<220> FEATURE:
<223> OTHER INFORMATION: Description of Artificial Sequence: a truncated mature BHV-1 gD

<400> SEQUENCE: 35

```
Leu Pro Thr Pro Ala Pro Arg Val Thr Val Tyr Val Asp Pro Pro Ala
  1               5                  10                  15

Tyr Pro Met Pro Arg Tyr Asn Tyr Thr Glu Arg Trp His Thr Thr Gly
                 20                  25                  30

Pro Ile Pro Ser Pro Phe Ala Asp Gly Arg Glu Gln Pro Val Glu Val
             35                  40                  45

Arg Tyr Ala Thr Ser Ala Ala Ala Cys Asp Met Leu Ala Leu Ile Ala
         50                  55                  60

Asp Pro Gln Val Gly Arg Thr Leu Trp Glu Ala Val Arg Arg His Ala
 65                  70                  75                  80

Arg Ala Tyr Asn Ala Thr Val Ile Trp Tyr Lys Ile Glu Ser Gly Cys
                 85                  90                  95

Ala Arg Pro Leu Tyr Tyr Met Glu Tyr Thr Glu Cys Glu Pro Arg Lys
                100                 105                 110

His Phe Gly Tyr Cys Arg Tyr Arg Thr Pro Pro Phe Trp Asp Ser Phe
            115                 120                 125

Leu Ala Gly Phe Ala Tyr Pro Thr Asp Asp Glu Leu Gly Leu Ile Met
        130                 135                 140

Ala Ala Pro Ala Arg Leu Val Glu Gly Gln Tyr Arg Arg Ala Leu Tyr
145                 150                 155                 160

Ile Asp Gly Thr Val Ala Tyr Thr Asp Phe Met Val Ser Leu Pro Ala
                165                 170                 175

Gly Asp Cys Trp Phe Ser Lys Leu Gly Ala Ala Arg Gly Tyr Thr Phe
                180                 185                 190

Gly Ala Cys Phe Pro Ala Arg Asp Tyr Glu Gln Lys Lys Val Leu Arg
            195                 200                 205

Leu Thr Tyr Leu Thr Gln Tyr Tyr Pro Gln Glu Ala His Lys Ala Ile
        210                 215                 220

Val Asp Tyr Trp Phe Met Arg His Gly Gly Val Val Pro Pro Tyr Phe
225                 230                 235                 240

Glu Glu Ser Lys Gly Tyr Glu Pro Pro Ala Ala Asp Gly Gly Ser
                245                 250                 255

Pro Ala Pro Pro Gly Asp Asp Glu Ala Arg Glu Asp Glu Gly Glu Thr
            260                 265                 270

Glu Asp Gly Ala Ala Gly Arg Glu Gly Asn Gly Gly Pro Pro Gly Pro
        275                 280                 285

Glu Gly Asp Gly Glu Ser Gln Thr Pro Glu Ala Asn Gly Gly Ala Glu
    290                 295                 300

Gly Glu Pro Lys Pro Gly Pro Ser Pro Asp Ala Asp Arg Pro Glu Gly
305                 310                 315                 320

Trp Pro Ser Leu Glu Ala Ile Thr His Pro Pro Ala Pro Ala Thr
                325                 330                 335

Pro Ala Arg Ala
            340
```

-continued

<210> SEQ ID NO 36
<211> LENGTH: 1020
<212> TYPE: DNA
<213> ORGANISM: Artificial Sequence
<220> FEATURE:
<223> OTHER INFORMATION: Description of Artificial Sequence: sequence encoding a truncated mature BHV-1 gD

<400> SEQUENCE: 36

```
ttgcctacac ccgcgccgcg ggtgacggta tacgtcgacc cgccggcgta cccgatgccg     60
cgatacaact acactgaacg ctggcacact accgggccca taccgtcgcc cttcgcagac    120
ggccgcgagc agcccgtcga ggtgcgctac gcgacgagcg cggcggcgtg cgacatgctg    180
gcgctgatcg cagacccgca ggtggggcgc acgctgtggg aagcggtacg ccggcacgcg    240
cgcgcgtaca acgccacggt catatggtac aagatcgaga gcgggtgcgc ccggccgctg    300
tactacatgg agtacaccga gtgcgagccc aggaagcact ttgggtactg ccgctaccgc    360
acacccccgt tttgggacag cttcctggcg ggcttcgcct accccacgga cgacgagctg    420
ggactgatta tggcggcgcc cgcgcggctc gtcgagggcc agtaccgacg cgcgctgtac    480
atcgacggca cggtcgccta tacagatttc atggtttcgc tgccggccgg ggactgctgg    540
ttctcgaaac tcggcgcggc tcgcgggtac acctttggcg cgtgcttccc ggcccgggat    600
tacgagcaaa agaaggttct gcgcctgacg tatctcacgc agtactaccc gcaggaggca    660
cacaaggcca tagtcgacta ctggttcatg cgccacgggg gcgtcgttcc gccgtatttt    720
gaggagtcga agggctacga gccgccgcct gccgccgatg gggttccccc cgcgccaccc    780
ggcgacgacg aggcccgcga ggatgaaggg gagaccgagg acggggcagc cgggcgggag    840
ggcaacggcg gcccccccagg acccgaaggc gacggcgaga gtcagacccc cgaagccaac    900
ggaggcgccg agggcgagcc gaaacccggc cccagccccg acgccgaccg ccccgaaggc    960
tggccgagcc tcgaagccat cacgcacccc ccgcccgccc ccgctacgcc cgctcgagct   1020
```

<210> SEQ ID NO 37
<211> LENGTH: 15
<212> TYPE: PRT
<213> ORGANISM: Artificial Sequence
<220> FEATURE:
<223> OTHER INFORMATION: Description of Artificial Sequence: 6XHIS leader

<400> SEQUENCE: 37

```
Met Arg Gly Ser His His His His His His Thr Asp Pro His Ala
  1               5                  10                  15
```

<210> SEQ ID NO 38
<211> LENGTH: 45
<212> TYPE: DNA
<213> ORGANISM: Artificial Sequence
<220> FEATURE:
<223> OTHER INFORMATION: Description of Artificial Sequence: sequence encoding 6XHIS leader

<400> SEQUENCE: 38

```
atgagaggat ctcaccatca ccatcaccat acggatccgc atgcc                     45
```

<210> SEQ ID NO 39
<211> LENGTH: 1017
<212> TYPE: DNA
<213> ORGANISM: Artificial Sequence
<220> FEATURE:
<223> OTHER INFORMATION: Description of Artificial Sequence: open reading frame for the 6XHIS leader, truncated mature gD, and GnRH tetramer encoded by bac-gD:GnRH

<400> SEQUENCE: 39

| | | |
|---|---|---|
| atgagcttgc ctacacccgc gccgcgggtg acggtatacg tcgacccgcc ggcgtacccg | 60 |
| atgccgcgat acaactacac tgaacgctgg cacactaccg ggcccatacc gtcgcccttc | 120 |
| gcagacggcc gcgagcagcc cgtcgaggtg cgctacgcga cgagcgcggc ggcgtgcgac | 180 |
| atgctggcgc tgatcgcaga cccgcaggtg gggcgcacgc tgtgggaagc ggtacgccgg | 240 |
| cacgcgcgcg cgtacaacgc cacggtcata tggtacaaga tcgagagcgg gtgcgcccgg | 300 |
| ccgctgtact acatggagta caccgagtgc gagcccagga agcactttgg gtactgccgc | 360 |
| taccgcacac ccccgttttg ggacagcttc ctggcgggct cgcctacccc cacggacgac | 420 |
| gagctgggac tgattatggc ggcgcccgcg cggctcgtcg agggccagta ccgacgcgcg | 480 |
| ctgtacatcg acggcacggt cgcctataca gatttcatgg tttcgctgcc ggccggggac | 540 |
| tgctggttct cgaaactcgg cgcggctcgc gggtacacct ttggcgcgtg cttcccggcc | 600 |
| cgggattacg agcaaaagaa ggttctgcgc ctgacgtatc tcacgcagta ctacccgcag | 660 |
| gaggcacaca aggccatagt cgactactgg ttcatgcgcc acggggcgt cgttccgccg | 720 |
| tattttgagg agtcgaaggg ctacgagccg ccgcctgccg ccgatggggg ttccccccgcg | 780 |
| ccacccggcg acgacgaggc ccgcgaggat aaggggaga ccgaggacgg ggcagccggg | 840 |
| cgggagggca acggcggccc cccaggaccc gaaggcgacg gcgagagtca gaccccccgaa | 900 |
| gccaacggag gcgccgaggg cgagccgaaa cccggcccca gccccgacgc cgaccgcccc | 960 |
| gaaggctggc cgagcctcga agccatcacg caccccccgc ccgcccccgc tacgccc | 1017 |

<210> SEQ ID NO 40
<211> LENGTH: 1272
<212> TYPE: DNA
<213> ORGANISM: Artificial Sequence
<220> FEATURE:
<223> OTHER INFORMATION: Description of Artificial Sequence: sequence
      encoding a 4GnRH-tmgD-4GnRH fusion protein

<400> SEQUENCE: 40

| | | |
|---|---|---|
| gagcactggt catatggtct gcgtccgggt gaacattgga gctacggtct acgccccggg | 60 |
| gaacactggt cttatggctt acggccggga gagcattgga gttacggcct ccgtccaggt | 120 |
| tccatgagct tgcctacacc cgcgccgcgg gtgacggtat acgtcgaccc gccggcgtac | 180 |
| ccgatgccgc gatacaacta cactgaacgc tggcacacta ccgggcccat accgtcgccc | 240 |
| ttcgcagacg gccgcgagca gcccgtcgag gtgcgctacg cgacgagcgc ggcggcgtgc | 300 |
| gacatgctgg cgctgatcgc agacccgcag gtggggcgca cgctgtggga agcggtacgc | 360 |
| cggcacgcgc gcgcgtacaa cgccacggtc atatggtaca agatcgagag cgggtgcgcc | 420 |
| cggccgctgt actacatgga gtacaccgag tgcgagccca ggaagcactt tgggtactgc | 480 |
| cgctaccgca caccccccgtt tgggacagc ttcctggcgg gcttcgccta ccccacggac | 540 |
| gacgagctgg gactgattat ggcggcgccc gcgcggctcg tcgagggcca gtaccgacgc | 600 |
| gcgctgtaca tcgacggcac ggtcgcctat acagatttca tggtttcgct gccggccggg | 660 |
| gactgctggt tctcgaaact cggcgcggct cgcgggtaca cctttggcgc gtgcttcccg | 720 |
| gcccgggatt acgagcaaaa gaaggttctg cgcctgacgt atctcacgca gtactacccg | 780 |
| caggaggcac acaaggccat agtcgactac tggttcatgc gccacggggg cgtcgttccg | 840 |
| ccgtattttg aggagtcgaa gggctacgag ccgccgcctg ccgccgatgg gggttccccc | 900 |

```
gcgccacccg gcgacgacga ggcccgcgag gatgaagggg agaccgagga cggggcagcc        960
gggcgggagg gcaacggcgg ccccccagga cccgaaggcg acggcgagag tcagaccccc       1020
gaagccaacg gaggcgccga gggcgagccg aaacccggcc ccagcccga cgccgaccgc        1080 cccgaaggct ggccgagcct cgaagccatc acgcacccc cgcccgcccc cgctacgccc       1140
gctcgagctc cagagcactg gtcatatggt ctgcgtccgg gtgaacattg gagctacggt      1200
ctacgccccg gggaacactg gtcttatggc ttacggccgg gagagcattg gagttacggc     1260
ctccgtccag gt                                                          1272
```

<210> SEQ ID NO 41
<211> LENGTH: 1144
<212> TYPE: DNA
<213> ORGANISM: Artificial Sequence
<220> FEATURE:
<223> OTHER INFORMATION: Description of Artificial Sequence: sequence
   encoding a tmgD-4GnRH fusion protein

<400> SEQUENCE: 41

```
cttgcctaca cccgcgccgc gggtgacggt atacgtcgac ccgccggcgt acccgatgcc        60
gcgatacaac tacactgaac gctggcacac taccgggccc ataccgtcgc ccttcgcaga       120
cggccgcgag cagcccgtcg aggtgcgcta cgcgacgagc gcggcggcgt gcgacatgct       180
ggcgctgatc gcagacccgc aggtggggcg cacgctgtgg gaagcggtac gccggcacgc       240
gcgcgcgtac aacgccacgg tcatatggta caagatcgag agcgggtgcg cccggccgct       300
gtactacatg gagtacaccg agtgcgagcc caggaagcac tttgggtact gccgctaccg       360 cacaccccg ttttgggaca gcttcctggc gggcttcgcc taccccacgg acgacgagct       420
gggactgatt atggcggcgc ccgcgcggct cgtcgagggc cagtaccgac gcgcgctgta       480
catcgacggc acgtcgcct atacagattt catggtttcg ctgccggccg gggactgctg      540
gttctcgaaa ctcggcgcgg ctcgcgggta cacctttggc gcgtgcttcc cggcccggga      600
ttacgagcaa aagaaggttc tgcgcctgac gtatctcacg cagtactacc gcaggaggc      660 acacaaggcc atagtcgact actggttcat gcgccacggg ggcgtcgttc cgccgtattt      720
tgaggagtcg aagggctacg agccgccgcc tgccgccgat gggggttccc ccgcgccacc      780
cggcgacgac gaggcccgcg aggatgaagg ggagaccgag gacggggcag ccgggcggga     840
gggcaacggc ggccccccag gacccgaagg cgacggcgag agtcagaccc ccgaagccaa     900
cggaggcgcc gagggcgagc cgaaacccgg ccccagcccc gacgccgacc gccccgaagg     960
ctggccgagc ctcgaagcca tcacgcaccc cccgcccgcc ccgctacgc ccgctcgagc     1020 tccagagcac tggtcatatg gtctgcgtcc gggtgaacat tggagctacg gtctacgccc    1080
cggggaacac tggtcttatg gcttacggcc gggagagcat tggagttacg gcctccgtcc    1140
aggt                                                                 1144
```

<210> SEQ ID NO 42
<211> LENGTH: 23
<212> TYPE: DNA
<213> ORGANISM: Artificial Sequence
<220> FEATURE:
<223> OTHER INFORMATION: Description of Artificial Sequence: primer
   P14-S1

<400> SEQUENCE: 42

```
ggagctccag agcactggtc ata                                               23
```

-continued

<210> SEQ ID NO 43
<211> LENGTH: 24
<212> TYPE: DNA
<213> ORGANISM: Artificial Sequence
<220> FEATURE:
<223> OTHER INFORMATION: Description of Artificial Sequence: primer
      P14-A138

<400> SEQUENCE: 43
aaagcttcaa cctggacgga ggcc                                           24

<210> SEQ ID NO 44
<211> LENGTH: 215
<212> TYPE: PRT
<213> ORGANISM: Actinobacillus pleuropneumoniae

<400> SEQUENCE: 44

Met Lys Lys Ala Val Leu Ala Ala Val Leu Gly Gly Ala Leu Leu Ala
 1               5                  10                  15

Gly Ser Ala Met Ala His Gln Ala Gly Asp Val Ile Phe Arg Ala Gly
                20                  25                  30

Ala Ile Gly Val Ile Ala Asn Ser Ser Asp Tyr Gln Thr Gly Ala
            35                  40                  45

Asp Val Asn Leu Asp Val Asn Asn Ile Gln Leu Gly Leu Thr Gly
        50                  55                  60

Thr Tyr Met Leu Ser Asp Asn Leu Gly Leu Glu Leu Ala Ala Thr
 65                  70                  75                  80

Pro Phe Ser His Lys Ile Thr Gly Lys Leu Gly Ala Thr Asp Leu Gly
                85                  90                  95

Glu Val Ala Lys Val Lys His Leu Pro Pro Ser Leu Tyr Leu Gln Tyr
               100                 105                 110

Tyr Phe Phe Asp Ser Asn Ala Thr Val Arg Pro Tyr Val Gly Ala Gly
               115                 120                 125

Leu Asn Tyr Thr Arg Phe Phe Ser Ala Glu Ser Leu Lys Pro Gln Leu
           130                 135                 140

Val Gln Asn Leu Arg Val Lys Lys His Ser Val Ala Pro Ile Ala Asn
145                 150                 155                 160

Leu Gly Val Asp Val Lys Leu Thr Asp Asn Leu Ser Phe Asn Ala Ala
                165                 170                 175

Ala Trp Tyr Thr Arg Ile Lys Thr Thr Ala Asp Tyr Asp Val Pro Gly
            180                 185                 190

Leu Gly His Val Ser Thr Pro Ile Thr Leu Asp Pro Val Val Leu Phe
        195                 200                 205

Ser Gly Ile Ser Tyr Lys Phe
    210                 215

<210> SEQ ID NO 45
<211> LENGTH: 364
<212> TYPE: PRT
<213> ORGANISM: Actinobacillus pleuropneumoniae

<400> SEQUENCE: 45

Met Lys Lys Ser Leu Val Ala Leu Thr Val Leu Ser Ala Ala Val
 1               5                  10                  15

Ala Gln Ala Ala Pro Gln Gln Asn Thr Phe Tyr Ala Gly Ala Lys Ala
                20                  25                  30

Gly Trp Ala Ser Phe His Asp Gly Ile Glu Gln Leu Asp Ser Ala Lys
            35                  40                  45

-continued

```
Asn Thr Asp Arg Gly Thr Lys Tyr Gly Ile Asn Arg Asn Ser Val Thr
 50                  55                  60
Tyr Gly Val Phe Gly Gly Tyr Gln Ile Leu Asn Gln Asp Lys Leu Gly
 65                  70                  75                  80
Leu Ala Ala Glu Leu Gly Tyr Asp Tyr Phe Gly Arg Val Arg Gly Ser
                 85                  90                  95
Glu Lys Pro Asn Gly Lys Ala Asp Lys Thr Phe Arg His Ala Ala
                100                 105                 110
His Gly Ala Thr Ile Ala Leu Lys Pro Ser Tyr Glu Val Leu Pro Asp
                115                 120                 125
Leu Asp Val Tyr Gly Lys Val Gly Ile Ala Leu Val Asn Asn Thr Tyr
130                 135                 140
Lys Thr Phe Asn Ala Ala Gln Glu Lys Val Lys Thr Arg Arg Phe Gln
145                 150                 155                 160
Ser Ser Leu Ile Leu Gly Ala Gly Val Glu Tyr Ala Ile Leu Pro Glu
                165                 170                 175
Leu Ala Ala Arg Val Glu Tyr Gln Trp Leu Asn Asn Ala Gly Lys Ala
                180                 185                 190
Ser Tyr Ser Thr Leu Asn Arg Met Gly Ala Thr Asp Tyr Arg Ser Asp
                195                 200                 205
Ile Ser Ser Val Ser Ala Gly Leu Ser Tyr Arg Phe Gly Gln Gly Ala
210                 215                 220
Val Pro Val Ala Ala Pro Ala Val Glu Thr Lys Asn Phe Ala Phe Ser
225                 230                 235                 240
Ser Asp Val Leu Phe Ala Phe Gly Lys Ser Asn Leu Lys Pro Ala Ala
                245                 250                 255
Ala Thr Ala Leu Asp Ala Met Gln Thr Glu Ile Asn Asn Ala Gly Leu
                260                 265                 270
Ser Asn Ala Ala Ile Gln Val Asn Gly Tyr Thr Asp Arg Ile Gly Lys
                275                 280                 285
Glu Ala Ser Asn Leu Lys Leu Ser Gln Arg Arg Ala Glu Thr Val Ala
                290                 295                 300
Asn Tyr Ile Val Ser Lys Gly Ala Pro Ala Ala Asn Val Thr Ala Val
305                 310                 315                 320
Gly Tyr Gly Glu Ala Asn Pro Val Thr Gly Ala Thr Cys Asp Lys Val
                325                 330                 335
Lys Gly Arg Lys Ala Leu Ile Ala Cys Leu Ala Pro Asp Arg Arg Val
                340                 345                 350
Glu Val Gln Val Gln Gly Thr Lys Glu Val Thr Met
                355                 360
```

<210> SEQ ID NO 46
<211> LENGTH: 369
<212> TYPE: PRT
<213> ORGANISM: Actinobacillus pleuropneumoniae

<400> SEQUENCE: 46

```
Met Lys Lys Ser Leu Val Ala Leu Ala Val Leu Ser Ala Ala Ala Val
  1               5                  10                  15
Ala Gln Ala Ala Pro Gln Gln Asn Thr Phe Tyr Ala Gly Ala Lys Val
                 20                  25                  30
Gly Gln Ser Ser Phe His His Gly Val Asn Gln Leu Lys Ser Gly His
                 35                  40                  45
Asp Asp Arg Tyr Asn Asp Lys Thr Arg Lys Tyr Gly Ile Asn Arg Asn
 50                  55                  60
```

-continued

```
Ser Val Thr Tyr Gly Val Phe Gly Gly Tyr Gln Ile Leu Asn Gln Asn
 65              70                  75                  80

Asn Phe Gly Leu Ala Thr Glu Leu Gly Tyr Asp Tyr Tyr Gly Arg Val
             85                  90                  95

Arg Gly Asn Asp Gly Glu Phe Arg Ala Met Lys His Ser Ala His Gly
            100             105             110

Leu Asn Phe Ala Leu Lys Pro Ser Tyr Glu Val Leu Pro Asp Leu Asp
            115             120             125

Val Tyr Gly Lys Val Gly Val Ala Val Val Arg Asn Asp Tyr Lys Ser
        130             135             140

Tyr Gly Ala Glu Asn Thr Asn Glu Pro Thr Glu Lys Phe His Lys Leu
145             150             155             160

Lys Ala Ser Thr Ile Leu Gly Ala Gly Val Glu Tyr Ala Ile Leu Pro
                165             170             175

Glu Leu Ala Ala Arg Val Glu Tyr Gln Tyr Leu Asn Lys Ala Gly Asn
            180             185             190

Leu Asn Lys Ala Leu Val Arg Ser Gly Thr Gln Asp Val Asp Phe Gln
        195             200             205

Tyr Ala Pro Asp Ile His Ser Val Thr Ala Gly Leu Ser Tyr Arg Phe
    210             215             220

Gly Gln Gly Ala Val Ala Pro Val Val Glu Pro Glu Val Val Thr Lys
225             230             235             240

Asn Phe Ala Phe Ser Ser Asp Val Leu Phe Asp Phe Gly Lys Ser Ser
                245             250             255

Leu Lys Pro Ala Ala Ala Thr Ala Leu Asp Ala Ala Asn Thr Glu Ile
            260             265             270

Ala Asn Leu Gly Leu Ala Thr Pro Ala Ile Gln Val Asn Gly Tyr Thr
        275             280             285

Asp Arg Ile Gly Lys Glu Ala Ser Asn Leu Lys Leu Ser Gln Arg Arg
    290             295             300

Ala Glu Thr Val Ala Asn Tyr Leu Val Ser Lys Gly Gln Asn Pro Ala
305             310             315             320

Asn Val Thr Ala Val Gly Tyr Gly Glu Ala Asn Pro Val Thr Gly Ala
                325             330             335

Thr Cys Asp Lys Val Lys Gly Arg Lys Ala Leu Ile Ala Cys Leu Ala
            340             345             350

Pro Asp Arg Arg Val Glu Val Gln Val Gln Gly Ala Lys Asn Val Ala
            355             360             365

Met
```

FUSION PROTEINS COMPRISING CARRIERS THAT CAN INDUCE A DUAL IMMUNE RESPONSE

This application claims the benefit under 35 U.S.C. 119 of U.S. Provisional Patent Application No. 60/120,454, filed Feb. 17, 1999.

FIELD OF THE INVENTION

The present invention is in the field of animal and human health, and is directed to fusion proteins useful in vaccine compositions.

BACKGROUND OF THE INVENTION

The vertebrate immune system comprises an intricate system of cells, secreted factors, and responses for protecting an organism from pathogenic infection by microbes, viruses, toxins, and other pathogens and irritants. Certain molecules, however, comprise epitopes which do not induce an effective immune response in a vertebrate because of their small size and/or because they are endogenously synthesized within the vertebrate and are therefore not perceived as "foreign" by the vertebrate's immune system. Methods for producing antibodies against certain peptides which are normally non-immunogenic, such as hormones, are desirable because immunoregulation of the activity of such peptides within the organism can thereby be achieved.

Hormone peptides have been combined with various carrier peptides in fusion proteins to elicit an effective immune response against the hormone when an organism is vaccinated with the fusion protein. The carrier portion causes the organism's immune system to recognize and generate antibodies against the hormone peptide which it would not otherwise generate.

U.S. Pat. No. 5,403,586 to Russell-Jones et al., for example, relates to fusion proteins which comprise an analog of gonadotropin releasing hormone (GnRH), also known as luteinizing hormone releasing hormone (LHRH), and a TraTp analog, wherein the presence of the TraTp analog in the fusion protein helps trigger the production of anti-GnRH antibodies. TraTp is an outer membrane lipoprotein produced by certain strains of E.coli, as described in U.S. Pat. No. 5,403,586, above.

U.S. Pat. No. 5,422,110 to Potter et al. relates to carrier systems that include chimeric proteins which comprise a leukotoxin polypeptide fused to a selected antigen. The leukotoxin functions to increase the immunogenicity of the antigen. Selected antigens that are disclosed therein include GnRH, somatostatin (SRIF), and rotavirus viral protein 4 (VP4).

WO 90/02187 relates to fusion proteins which comprise an antigenic, hydrophilic portion, such as Hepatitis B surface antigen (HBsAg), and a peptide, such as GnRH, which alone is not substantially antigenic GnRh is a decapeptide endogenously produced, mainly in the hypothalamus. It is highly conserved among vertebrate species. In mammals, the GnRH gene encodes the decapeptide glu-his-trp-ser-tyr-gly-leu-arg-pro-gly (SEQ ID NO: 13) with subsequent post-translational modification of the N and C termini to pyroglutamic acid and glycinamide, respectively. GnRH has been shown to play a critical role in the regulation of reproductive functions in all major vertebrates by regulating the production and release of follicle-stimulating hormone (FSH) and luteinizing hormone (LH) from the pituitary gland. Because FSH and LH play a role in spermatogenesis and ovulation, as well as steroidogenesis, vaccines that result in the production of antibodies against GnRH lead to the suppression of reproductive function (fertility) in both males and females, and should also control secondary sexual characteristics such as gender-related behavior. In males, LH regulates steroidogenesis in Leydig cells. Thus, active immunization of males against GnRH leads to testicular atrophy and a decrease in testosterone production and testicular function, (Ladd, A. et al., 1994, Biol. Reprod. 51:1076–1083; Ladd A., 1993, Am. J. Reprod. Immunol. 29:189–194). A GnRH vaccine has been approved by the United States Food and Drug Administration as an investigational new drug for the treatment of prostate cancer (Ladd A., 1993, above). The development of a GnRH immuno-contraceptive is a useful alternative to surgical sterilization in animals, and has the added advantage of being reversible, since spermatogeneis and fertility can return to normal by simply allowing anti-GnRH titers to decline (Ladd, A. et al., 1989, J. Reprod. Immunol. 15:85–101). However, since GnRH is a small self peptide and has a short half-life (WO 90/02187, Mar. 8, 1990), it is only weakly immunogenic, even when injected with a powerful adjuvant. For example, a significant proportion of animals are not able to mount an effective antibody response against GnRH when administered in Freund's complete adjuvant. In order to generate a significant antibody response, GnRH must therefore be conjugated, chemically or recombinantly, to a carrier protein.

None of the aforementioned references, however, teach or suggest using a carrier which triggers an immunoinhibiting response against itself.

SUMMARY OF THE INVENTION

The subject invention provides a fusion protein for producing a dual immune response in a vertebrate, which fusion protein comprises: (a) a first proteinaceous portion analogous to all or part of a peptide endogenously synthesized within the vertebrate, the activity of which peptide is to be inhibited within the vertebrate, and which proteinaceous portion by itself is incapable of eliciting an effective immunoinhibitory response in said vertebrate; connected to (b) a second proteinaceous portion analogous to all or part of an immunogen from a pathogen, which pathogen is capable of pathogenically infecting the vertebrate; the portion (b) causing the vertebrate's immune system to recognize the portion (a) and produce a response that: (i) inhibits the activity of the peptide endogenously synthesized within the vertebrate; and (ii) protects the vertebrate from infection by the pathogen, when the vertebrate is vaccinated with an effective amount of the fusion protein.

The subject invention further provides, in a second aspect, a fusion protein for producing an immune response in a vertebrate, which fusion protein comprises: (a) a first proteinaceous portion analogous to all or part of a peptide, the activity of which peptide is to be inhibited within the vertebrate, and which proteinaceous portion by itself is incapable of eliciting an effective immunoinhibitory response in said vertebrate; connected to (b) a second proteinaceous portion analogous to all or part of a Bovine Herpes Virus Type-1 (BHV-1) antigen; the second proteinaceous portion (b) causing the vertebrate's immune system to recognize the first proteinaceous portion (a) and produce an immune response capable of inhibiting the activity of the peptide within the vertebrate when the vertebrate is vaccinated with an effective amount of the fusion protein.

The subject invention further provides fusion proteins as recited in the preceding two paragraphs which are recombinant fusion proteins.

The subject invention further provides a polynucleotide molecule comprising a nucleotide sequence encoding a fusion protein of the present invention.

The subject invention further provides a vector which comprises a polynucleotide molecule comprising a nucleotide sequence which encodes a fusion protein of the present invention.

The subject invention further provides a transformed cell comprising a polynucleotide molecule comprising a nucleotide sequence encoding a fusion protein of the present invention.

The subject invention further provides a dual-function vaccine which comprises an amount of a fusion protein as set forth above comprising: (a) a first proteinaceous portion analogous to all or part of a peptide endogenously synthesized within a vertebrate, the activity of which peptide is to be inhibited within the vertebrate, and which proteinaceous portion by itself is incapable of eliciting an effective immunoinhibitory response in said vertebrate; connected to (b) a second proteinaceous portion analogous to all or part of an immunogen from a pathogen, which pathogen is capable of pathogenically infecting the vertebrate; the portion (b) capable of causing the vertebrate's immune system to recognize the portion (a) and produce a response that: (i) inhibits the activity of the peptide endogenously synthesized within the vertebrate; and (ii) protects the vertebrate from infection by the pathogen, said fusion protein being present in the dual-function vaccine in an amount effective to inhibit the activity of the peptide from which portion (a) is derived and to protect the vertebrate from infection by the pathogen from which portion (b) is derived, said dual-function vaccine further comprising a carrier acceptable for pharmaceutical or veterinary use.

The subject invention further provides a method for inhibiting the activity of an endogenously-synthesized peptide in a vertebrate and for protecting the vertebrate from a pathogenic infection, which method comprises immunizing the vertebrate with a vaccine as recited in the preceding paragraph in an amount effective to inhibit the activity of the peptide and to protect against infection by the pathogen.

The subject invention further provides a vaccine for inhibiting the activity of a peptide in a vertebrate which comprises a fusion protein as set forth above which comprises: (a) a first proteinaceous portion analogous to all or part of a peptide, the activity of which peptide is to be inhibited within the vertebrate, and which proteinaceous portion by itself is incapable of eliciting an effective immunoinhibitory response in said vertebrate; connected to (b) a second proteinaceous portion analogous to all or part of a BHV-1 antigen; the second proteinaceous portion (b) being capable of causing the vertebrate's immune system to recognize the first proteinaceous portion (a) and to produce a response that inhibits the activity of the peptide within the vertebrate, the fusion protein being present in the vaccine in an amount effective to inhibit the activity of the peptide in the vertebrate, and the vaccine further comprising a carrier acceptable for pharmaceutical or veterinary use.

The subject invention further provides a method for inhibiting the activity of a peptide in a vertebrate which comprises immunizing the vertebrate with a vaccine as recited in the preceding paragraph in an amount effective to inhibit the peptide.

The subject invention further provides a method of making polyclonal antibodies directed against a peptide that is endogenously synthesized in a vertebrate which comprises vaccinating such a vertebrate with an antibody-inducing amount of a fusion protein of the present invention, or a vector or transformed cell comprising a polynucleotide molecule comprising a nucleotide sequence encoding such a fusion protein, which fusion protein comprises a portion (a) analogous to all or part of a peptide endogenously synthesized within the vertebrate; obtaining serum containing polyclonal antibodies from the vaccinated vertebrate; and isolating from the serum polyclonal antibodies which bind to the endogenously-synthesized peptide; thereby making polyclonal antibodies directed against the peptide.

The subject invention further provides polyclonal antibodies directed against an endogenously-synthesized peptide made according to the method recited in the preceding paragraph.

The subject invention further provides a method of making a monoclonal antibody directed against a peptide that is endogenously synthesized in a vertebrate which comprises vaccinating such a vertebrate with an antibody-inducing amount of a fusion protein of the present invention, or vector or transformed cell comprising a polynucleotide molecule comprising a nucleotide sequence encoding such a fusion protein, which fusion protein comprises a portion (a) analogous to all or part of a peptide endogenously synthesized within the vertebrate; and isolating a spleen cell from the vaccinated vertebrate which spleen cell excretes a monoclonal antibody that specifically binds to the endogenously-synthesized peptide; thereby making a monoclonal antibody directed against the peptide.

The subject invention further provides monoclonal antibodies directed against an endogenously-synthesized peptide made according to the method recited in the preceding paragraph.

BRIEF DESCRIPTION OF THE FIGURES

FIG. 4 (FIGS. 4A-4C): Alignment report (DNA alignment) comparing BHV-1 gD from clone FlgD/Pots207nco(#79) (gD/Pots, top sequence) and BHV-1 gD having GenBank Accession No. M59846 (bottom sequence) (Tikoo et al., 1990, above) (GenBank DNA sequence database of the U.S. National Center for Biotechnology Information (NCBI, Bethesda, Md.)). Clustal method with weighted residue weight table was used for this report.

"TM" stands for transmembrane domain. Boxed residues in the FlgD/Pots207nco(#79) clone are those that differ from residues in M59846. M59846 DNA is SEQ ID NO: 18.

FIG. 5: Amino acid alignment between gD/Pots (bottom sequence) and M59846 (top sequence). Clustal method with PAM250 residue weight table was used. Residues in gD/Pots which differ from residues in M59846 are boxed. M59846 is SEQ ID NO: 19.

FIG. 6: (FIGS. 6A-6D): pQE-tmgD. Nucleotide coding sequence for the tmgD, flanked by plasmid pQE-31 sequences, including a sequence encoding a 6×HIS tag, which is expressed connected to the tmgD (SEQ ID NO: 20). The amino acid sequence of the tmgD with the connected 6×HIS tag is also shown (SEQ ID NO: 21).

Figure 7A:
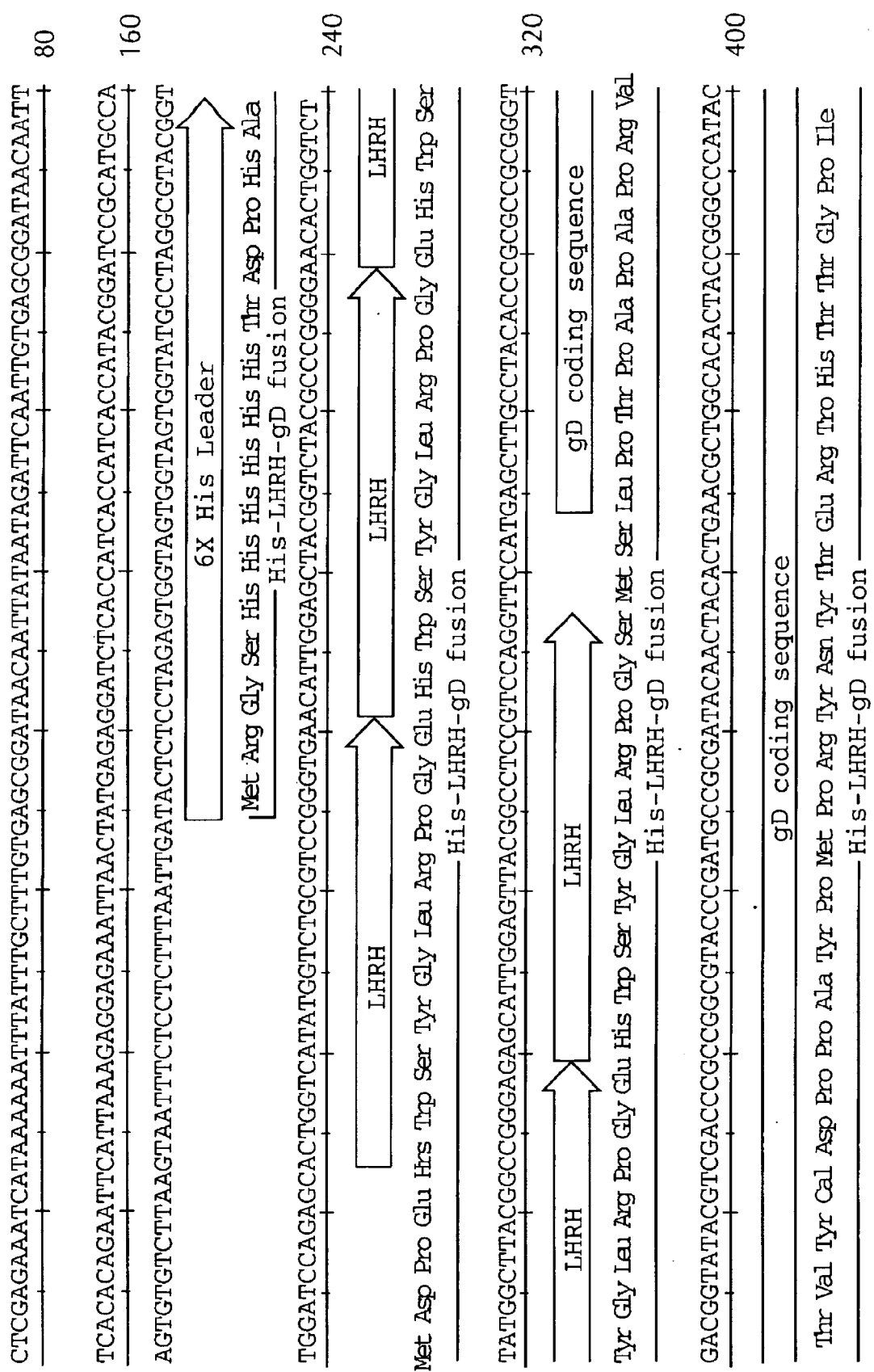
Figure 7D:
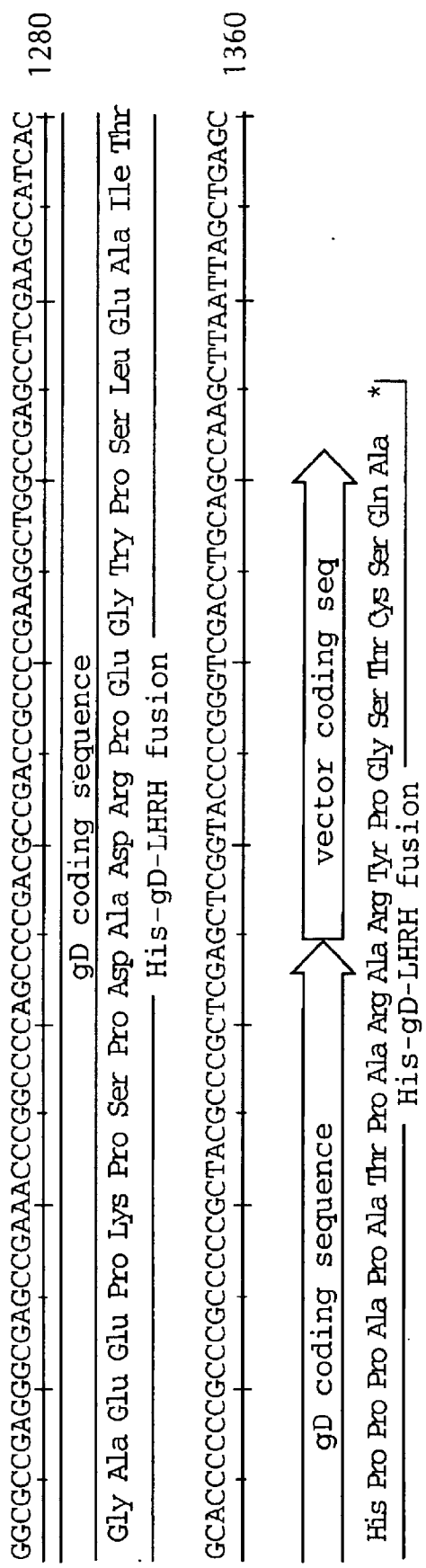

FIG. 7 (FIGS. 7A-7D): Nucleotide coding sequence and flanking sequences for plasmid pQE-GnRH:gD (SEQ ID NO: 22). Amino acid sequence of the 4GnRH-tmgD fusion protein, including a 6×HIS tag, is also shown (SEQ ID NO: 23).

Figure 8D:
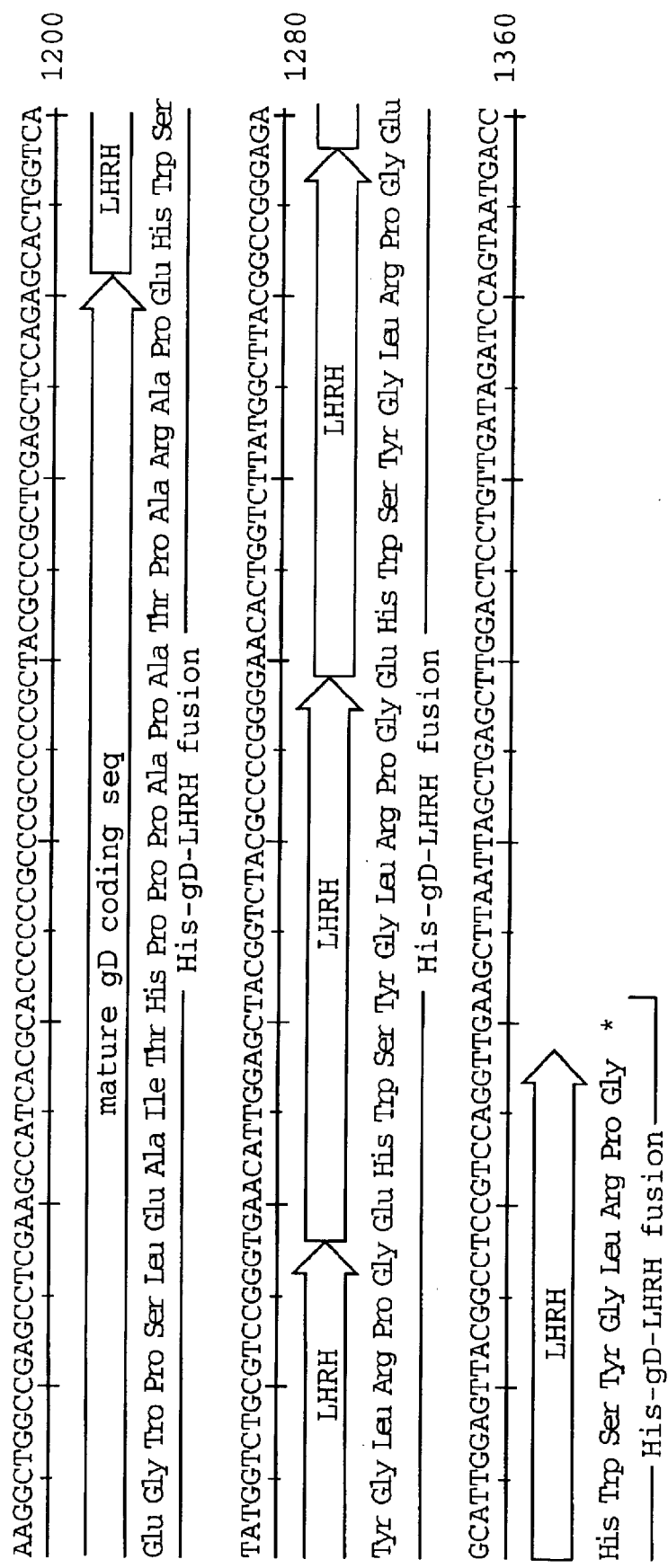

FIG. 8 (FIGS. 8A-8D): pQE-gD:GnRH. Nucleotide coding sequence and plasmid flanking sequences are shown (SEQ ID NO: 24). The amino acid sequence of the tmgD-4GnRH, with a 6×HIS tag, is also shown (SEQ ID NO: 25).

Figure 9A:
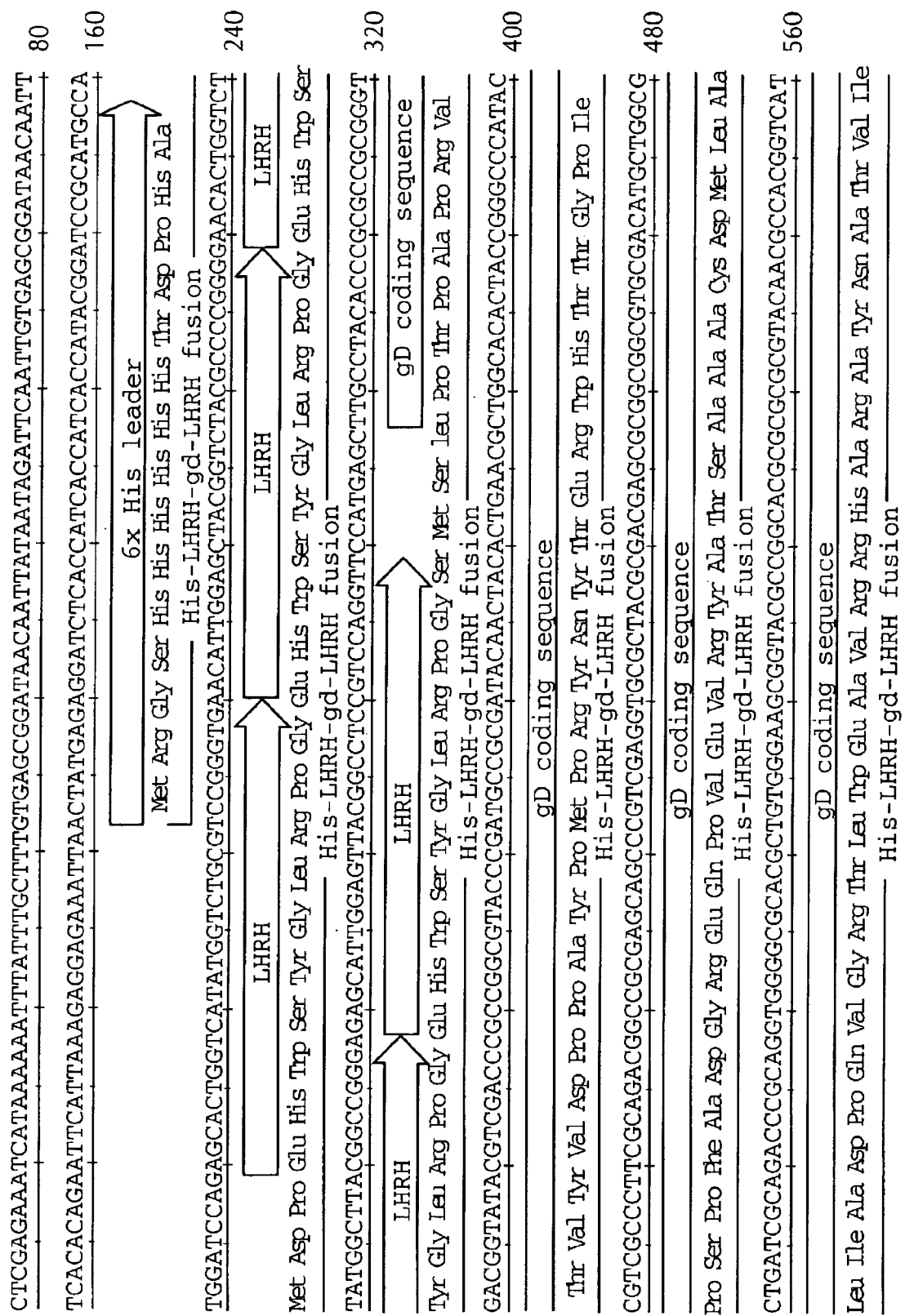
Figure 9D:
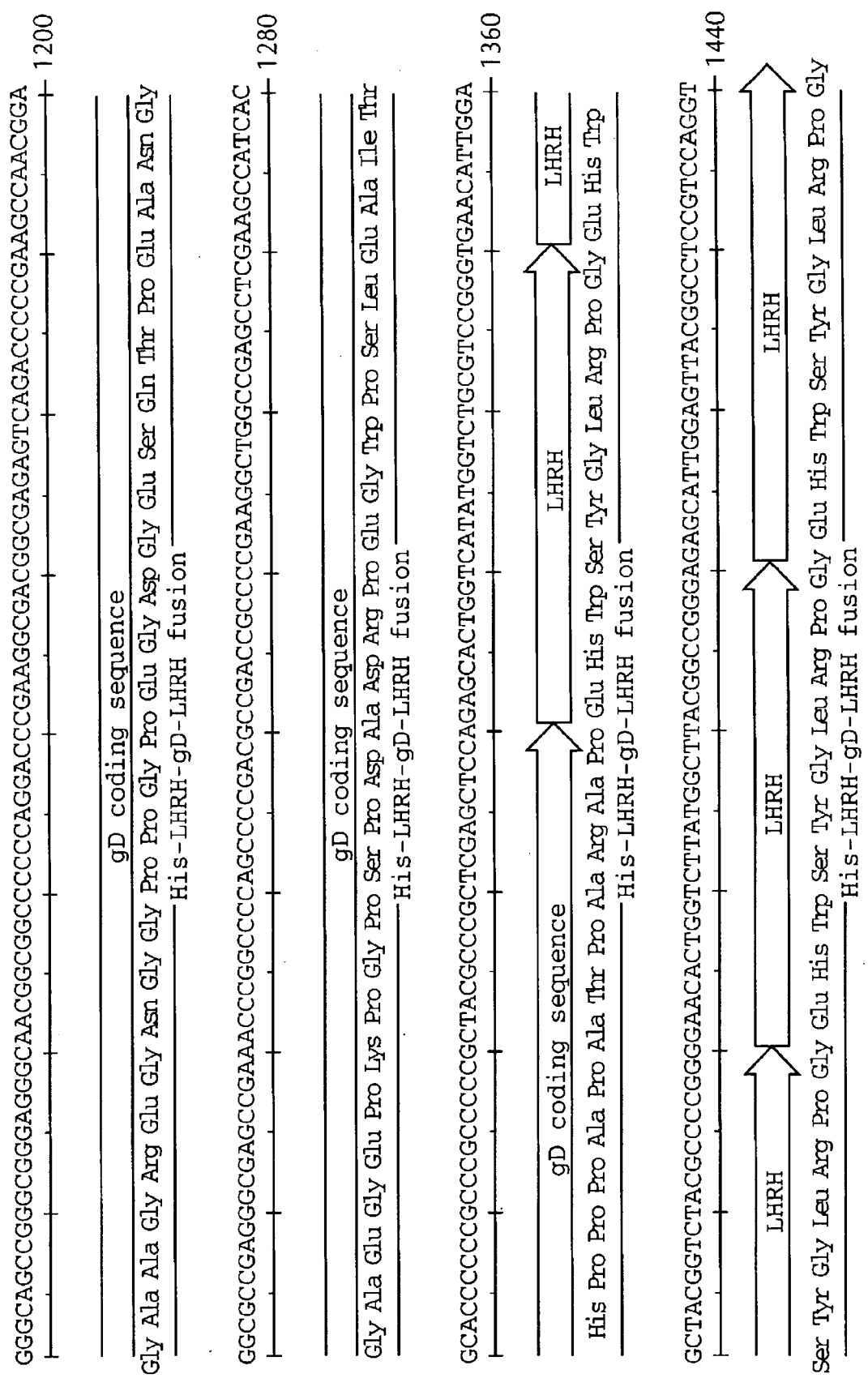

FIG. 9 (FIGS. 9A-9D): pQE-GnRH:gD:GnRH. Nucleotide coding sequence and plasmid flanking sequences are shown (SEQ ID NO: 26). The amino acid sequence of the 4GnRH-tmgD-4GnRH, with a 6×HIS tag, is also shown (SEQ ID NO: 27).

Figure 10:
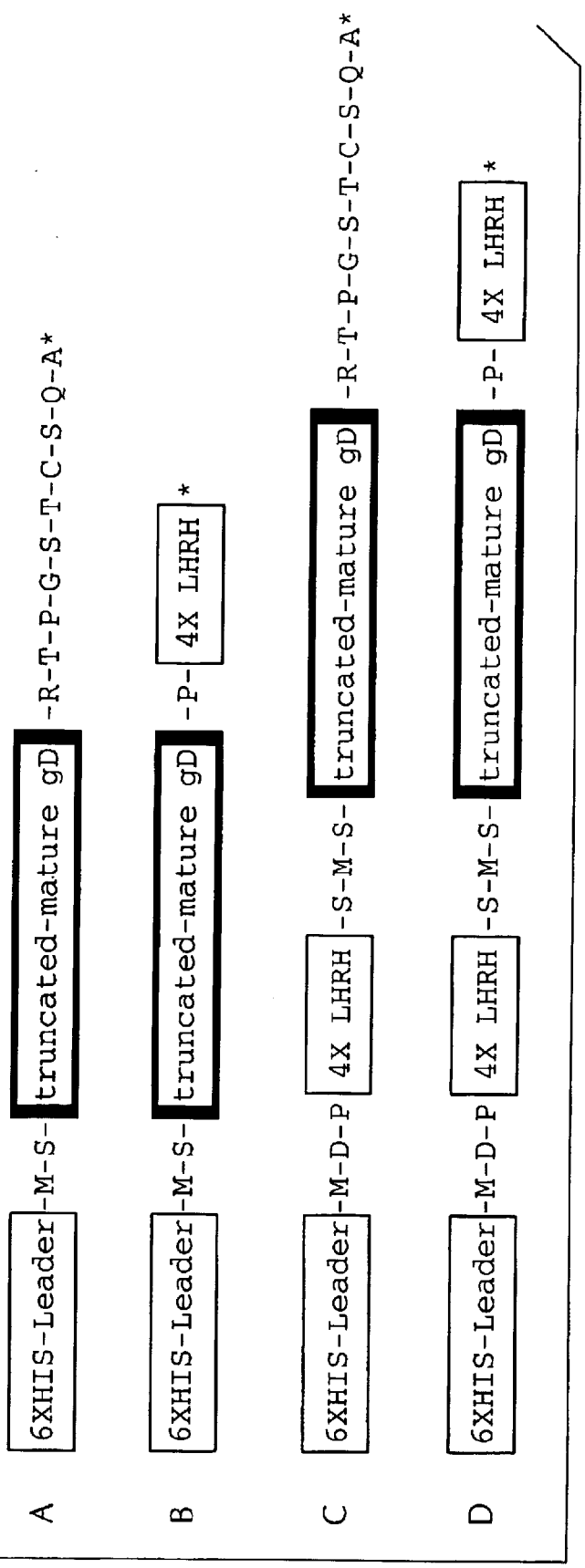
Figure 11A:
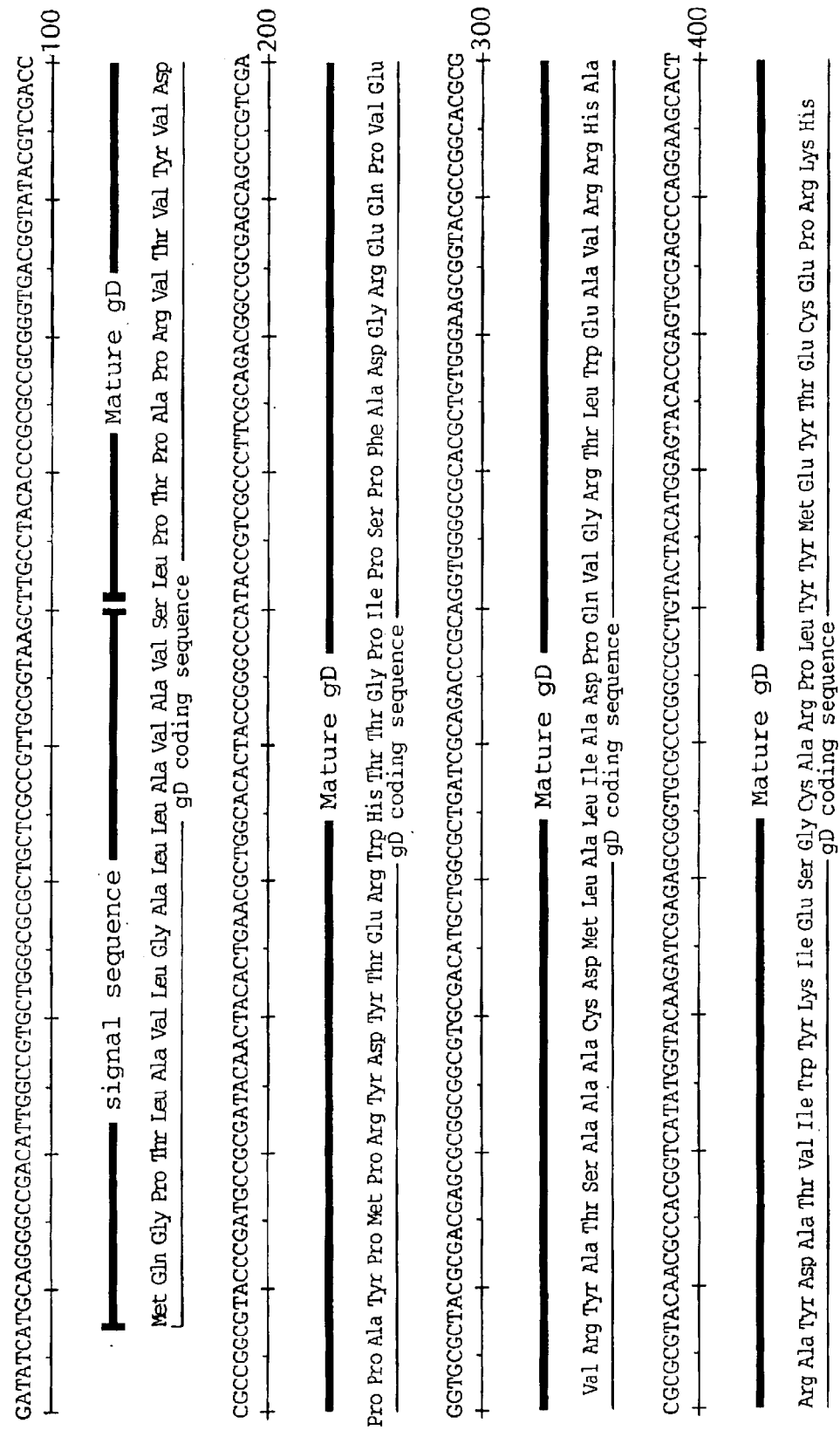
Figure 11C:
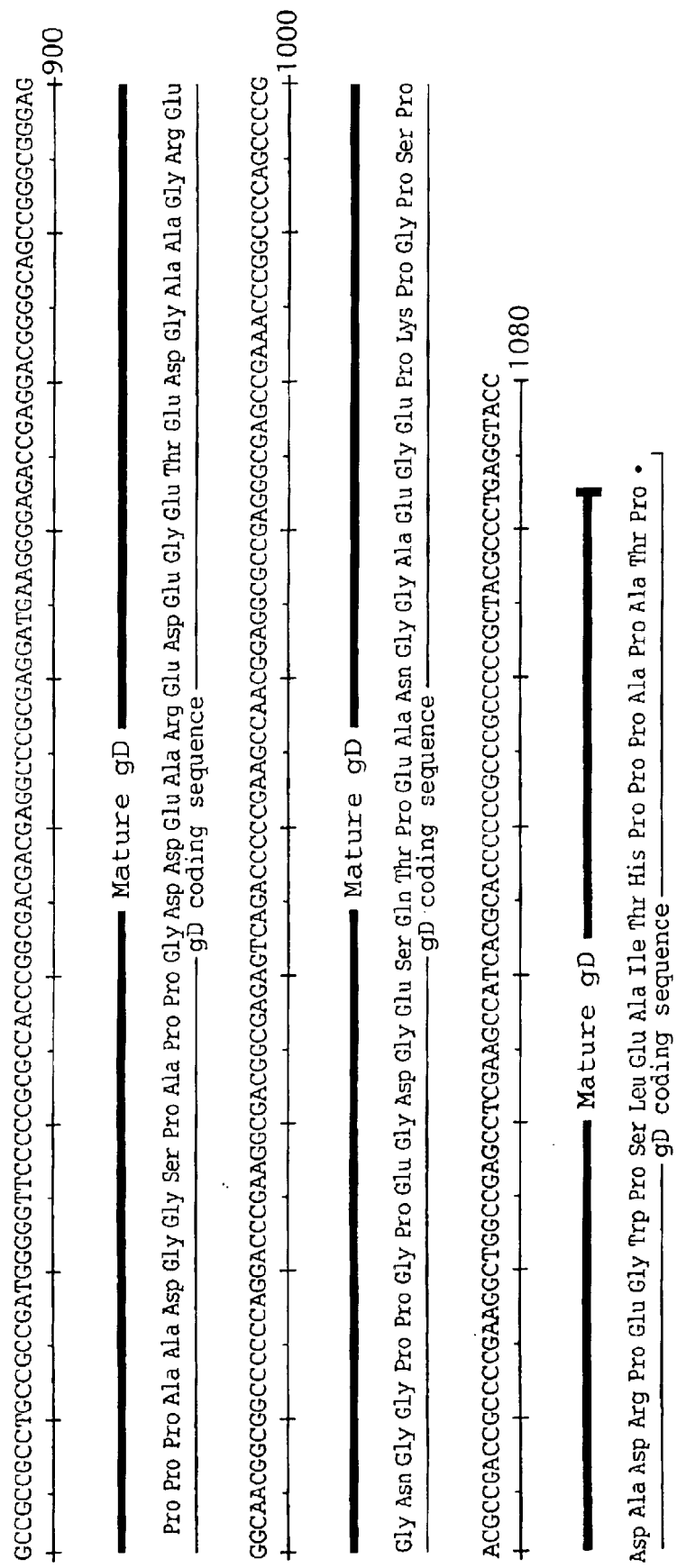
Figure 12A:
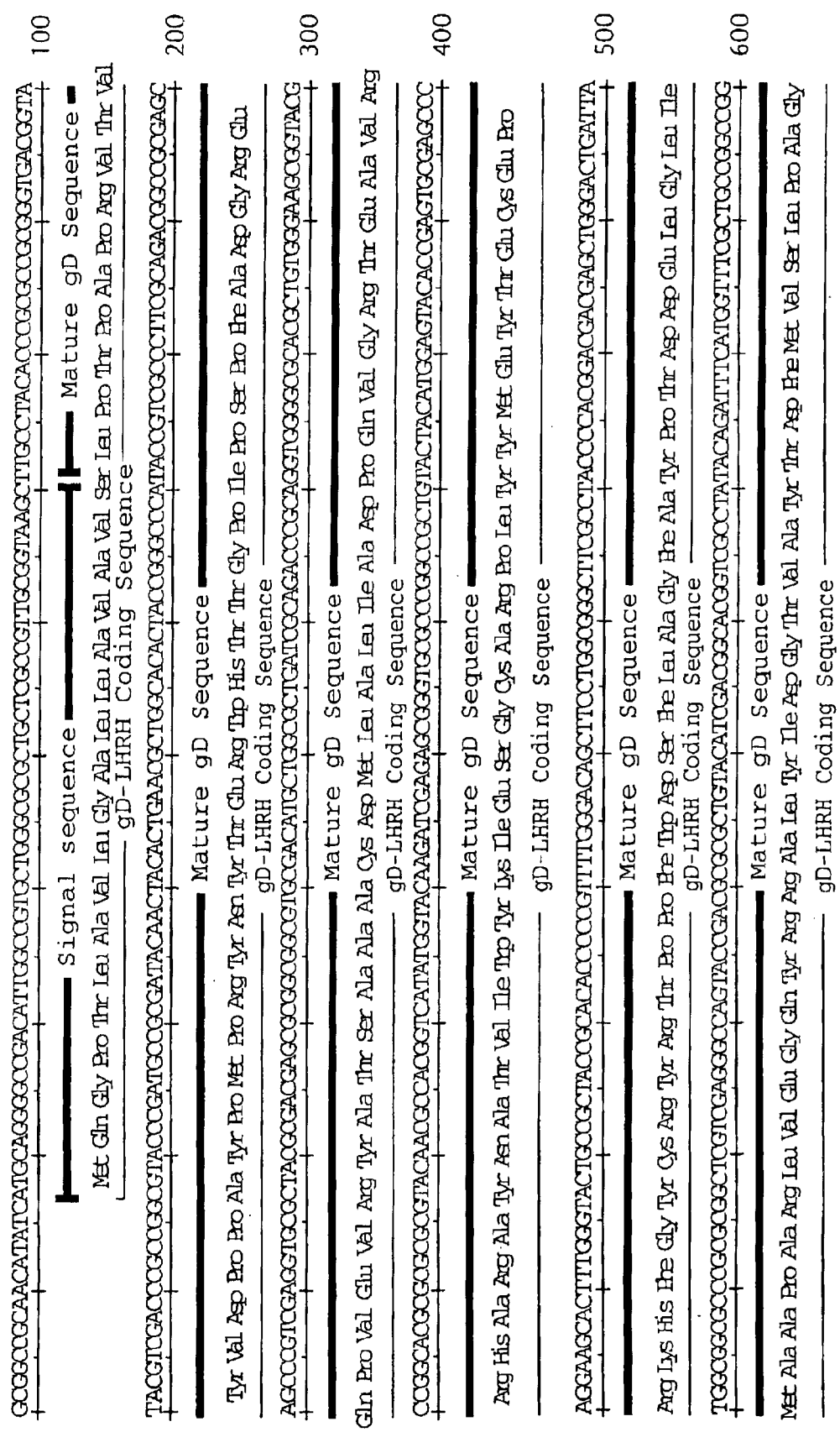
Figure 12C:
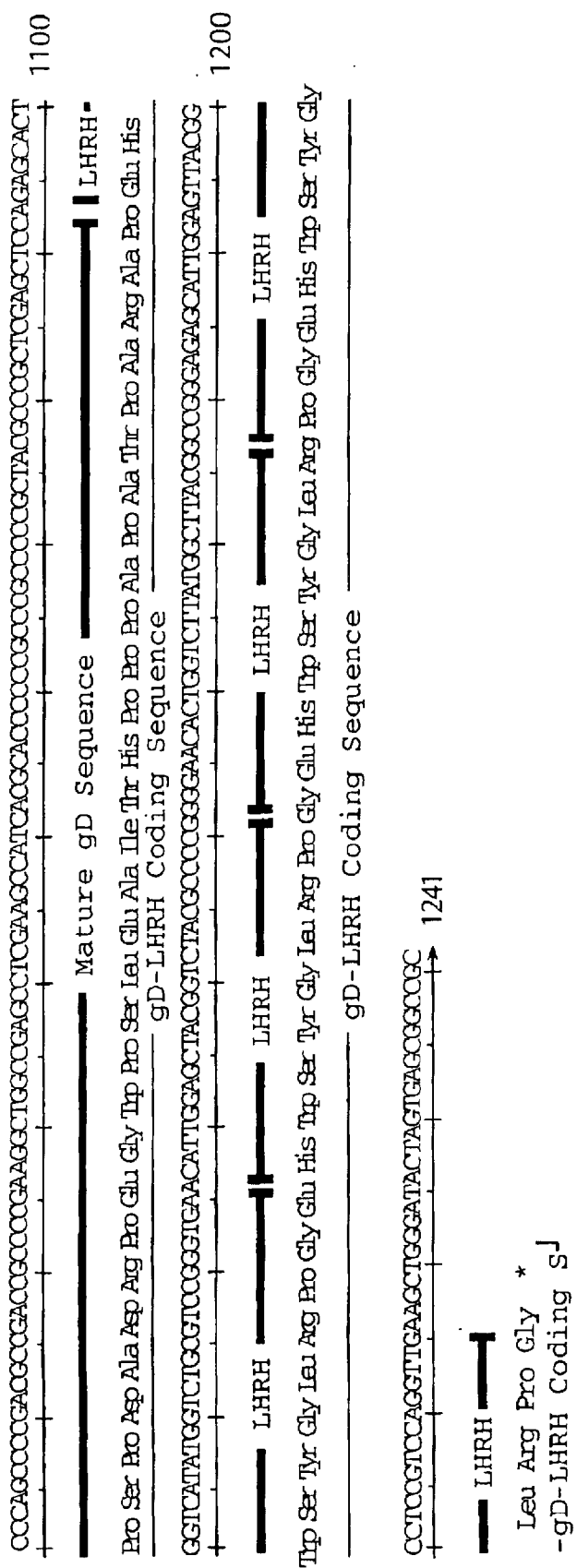

FIG. 10: Comparison of expression products from bacterial vector pQE constructs. "A" is pQE-tmgD, "B" is pQE-gD:GnRH, "C" is pQE-GnRH:gD, and "D" is pQE-GnRH:gD:GnRH. The amino acids which link the gD portions, the GnRH tetramers, and the 6×HIS tags are depicted in this figure.

FIG. 11 (FIGS. 11A-11B): Nucleotide sequence (SEQ ID NO: 28) from plasmid pCMV-tgD encoding a truncated gD, and deduced amino acid sequence (SEQ ID NO: 29) of the truncated gD expression product including the signal sequence.

FIG. 12 (FIGS. 12A-12C): Nucleotide sequence (SEQ ID NO: 30) from plasmid pCMV-gD:GnRH (ATCC Accession No. 203370) encoding a tgD-4GnRH fusion protein, with deduced amino acid sequence (SEQ ID NO: 31) of the fusion protein product including signal sequence.

DETAILED DESCRIPTION OF THE INVENTION

Fusion Proteins

In a first aspect, the subject invention provides fusion proteins that induce in a vertebrate a dual immune response that both inhibits the activity of a peptide endogenously synthesized by the vertebrate and also inhibits a pathogenic infection in the vertebrate. The inhibition of the endogenously-synthesized peptide is obtained by connecting a first proteinaceous portion which is analogous to all or part of the endogenously-synthesized peptide to a carrier, the carrier being a proteinaceous portion analogous to all or part of an immunogen from a pathogen capable of pathogenically infecting the vertebrate. In addition to functioning as a carrier (i.e. enhancing an immune response against the analog of the endogenously-synthesized peptide or part thereof), the portion analogous to the immunogen or immunogen part from the pathogen also induces a response against itself in the vertebrate and thus protects the vertebrate from infection by the pathogen.

Since two major causes of economic loss in feedlot cattle in the United States and in range-fed cattle globally are bovine respiratory disease (BRD) caused by BHV-1 infection and sexual and aggressive behavior, a product that will simultaneously treat BRD and also inhibit secondary sexual characteristics, e.g., aggression, would improve carcass quality and productivity by eliminating or reducing these infectious and endocrine causes of production losses in cattle. Thus, as one embodiment of the present invention, glycoprotein D (gD), which is an immunogen from BHV-1, was selected as a carrier to combine with a GnRH peptide in a fusion protein in order to regulate GnRH activity in cattle while simultaneously providing protection against BRD.

Certain proteinaceous portions that are analogs to an immunogen from a pathogen or part of an immunogen from a pathogen, such as the BHV-1 glycoprotein analogs described herein, have not previously been disclosed or suggested as carriers. Thus, a second aspect of the subject invention provides a fusion protein for producing an immune response in a vertebrate, which fusion protein comprises as a carrier a proteinaceous portion analogous to all or part of a BHV-1 antigen. In this second aspect, the vertebrate need not be a vertebrate which is capable of being pathogenically infected by BHV-1; the BHV-1 antigen analog simply acts as a carrier that induces an immune response inhibiting the activity of proteinaceous portion (a).

Thus, if a fusion protein of this invention comprises, for example, a portion (a) analogous to all or part of a GnRH peptide, and a portion (b) analogous to all or part of a BHV-1 antigen, such a fusion protein will produce a dual immune response in cattle, but will also be useful in other vertebrate species for inhibiting GnRH activity without protecting against BHV-1 infection, as such other species are not pathogenically infected by BHV-1.

For purposes of this invention, "fusion protein" means a molecule comprising a plurality of proteinaceous portions connected together. Thus, fusion proteins of this invention include chemical conjugates (chemically connected portion (a) and (b)) and recombinant fusion proteins. A fusion protein according to this invention comprises a proteinaceous portion (a) and a proteinaceous portion (b), by which is meant that the molecule may comprise at least one portion (a) and at least one portion (b), but can comprise more than one portion (a) and/or more than one portion (b). The portions (a) and (b) can be connected linearly. If multiple portions of (a) and/or (b) are present, then the portions can be connected linearly, or they can be connected in a branched manner, for example with one of the portions (a) or (b) centrally located in the molecule and with other portions (a) or (b) multiply connected to the central portion. Other patterns of connection which can be ascertained by those of ordinary skill in the art are included within the subject invention, as long as at least one portion (a) and one portion (b) are present in the fusion proteins.

The portions (a) and (b) can be positioned with respect to one another so as to optimize an effective immune response against the portion (a), as well as the portion (b) if desired. Such positioning can be ascertained by methods known to those of ordinary skill in the art. For example a fusion protein as described herein can be tested by Western blot with antibodies against (a) andor (b) to determine if portions (a) and/or (b) are positioned so as to optimize binding of antibodies specific thereto.

The portions of the subject fusion proteins can be connected by means including chemical connections and recombinant connections. A "chemical connection" involves creating a chemical intermediate from one proteinaceous portion, and reacting the intermediate with another proteinaceous portion. For example, a "chemical connection" can involve forming a direct covalent bond between an organic group of one proteinaceous portion, such as portion (a), and an organic group of the other proteinaceous portion, e.g. portion (b), provided the portions have organic groups which are able to react under appropriate reaction conditions to form such a covalent bond. As another example, one of the proteinaceous portions, such as portion (a), can be derivatized to form an intermediate that contains substituents that will react with (b) portions. A "recombinant connection" involves ligating a nucleic add encoding one proteinaceous portion to a nucleic acid encoding another proteinaceous portion, and expressing a protein therefrom in an appropriate expression system. Chemical connections and recombinant connection are known in the art and are described in further detail herein.

The term "carrier" as used herein (except when in the phrase "pharmaceutically acceptable carrier", "carrier acceptable for pharmaceutical of veterinary use", and like phrases, or as otherwise indicated) means a molecule which elicits or enhances an immune response against a second molecule when connected thereto.

The term "analogous to" as used herein to describe portions of a fusion protein, unless otherwise indicated, means "having the same or substantially the same structure as", for example, having the same or substantially the same amino acid sequence. For example, a proteinaceous portion which is analogous to a peptide endogenously synthesized by a vertebrate has the same or substantially the same amino acid sequence as the endogenously-synthesized peptide. "Substantially the same amino acid sequence" means a polyaminoacid sequence otherwise having the amino acid sequence of the endogenously synthesized peptide, but in which one or more amino acid residues have been deleted, added, or substituted with a different amino acid residue, where the resulting polyaminoacid molecule is useful in practicing the present invention. A polyaminoacid molecule is useful in practicing the present invention if it can result in a specific immune response when in the fusion protein product. Amino acid substitution will preferably be conservative substitutions which are well-known in the art. Rules for making such substitutions include those described by Dayhof, M. D., 1978, Nat. Biomed. Res. Found., Washington, D.C., Vol. 5, Sup. 3, among others.

When a portion (a) or portion (b) of a fusion protein of the present invention is referred to herein as being "derived from" a peptide or pathogen, this means that the portion is analogous to all or part of the peptide or all or part of an immunogen (or antigen) from the pathogen, respectively.

"Part of" a peptide, antigen, or immunogen for purposes of this invention, unless otherwise indicated, is any part such that the resulting polyaminoacid molecule is useful in practicing the present invention. This means that the part must be sufficient to elicit an immune response against the pathogen from which (b) is derived and/or the peptide from which (a) is derived. Ascertaining such parts is within the ordinary skill in the art. In a preferred embodiment, the part of the peptide, antigen or immunogen comprises at least 60%, more preferably 70%, and even more preferably at least 90% of the amino acid sequence of the particular peptide, antigen or immunogen. The actual percentage of the peptide, antigen, or immunogen is less important than is including in the part those amino acid residues which will elicit an immune response against (b) and/or (a).

The terms "immunogen" and "antigen" as used herein mean a molecule which is able to trigger an effective immune response in a particular vertebrate or vertebrate species. immunogens useful for the subject invention are proteinaceous molecules, i.e., molecules comprised of a sequence of amino acids, but which can also include non-protein groups, e.g., carbohydrate moieties.

The term "immune response" for purposes of this invention means the production of antibodies and/or cells (such as T lymphocytes) that are directed specifically or indirectly against, or assist in the decomposition or inhibition of, a particular epitope or particular epitopes. An "effective immune response" is an immune response that, regarding portion (a), is directed against one or more epitopes so as to inhibit the activity of a peptide endogenously synthesized in the vaccinated vertebrate; and, regarding portion (b), is directed against one or more epitopes of a pathogen so as to protect against the pathogen in the vaccinated vertebrate. "Triggering an immune response" and like phrases as used herein mean inducing and/or enhancing an immune response in a vertebrate in response to vaccination. Phrases such as "inhibition of infection" and "protection from infection" refer not only to the absolute prevention of infection, but also to any detectable reduction in the degree or rate of infection by such a pathogen, or any detectable reduction in the severity of the disease or any symptom or condition resulting from infection by the pathogen in the vaccinated animal as compared to an unvaccinated animal. A response which inhibits infection may be induced in animals which have not previously been infected with the pathogen and/or are not infected with the pathogen at the time of vaccination. Such phrases are intended also to include inhibiting the rate or degree of infection in an animal already infected with the pathogen at the time of vaccination.

The term "dual immune response" as used herein means ah effective immune response as defined above which inhibits the activity of more than one peptide, and preferably different peptides, for example an endogenously-synthesized hormone peptide and a viral peptide.

A "dual-function vaccine", as used herein, means a vaccine which can produce an immune response in a vertebrate vaccinated therewith that is directed against more than one peptide, and preferably two different peptides, within the vertebrate, for example a hormone endogenously synthesized by the vertebrate and a viral peptide of a virus which pathogenically infects the vertebrate.

The phrase "endogenously-synthesized peptide", as used herein and unless Aotherwise indicated, means a peptide which is synthesized by a vertebrate as part of the vertebrate's metabolic functioning. Examples of endogenously-synthesized peptides include, but are not limited to, hormones and enzymes.

"Inhibiting the activity of a peptide" and like phrases used herein mean interfering with the peptide's ability to perform its normal function, for example its ability to catalyze a biochemical reaction (if the peptide is an enzyme), to trigger a biophysical response (if the peptide is a hormone), or to participate in viral infectivity or replication (if the peptide is a viral peptide). The phrases "amount effective to inhibit the activity of the peptide from which portion (a) is derived", "amount effective to inhibit GnRH activity", and the like, refer to that amount of fusion protein capable of inducing an immune response which is sufficient to interfere with the peptide's ability to perform its function, such as preventing GnRH from stimulating or reducing the ability of GnRH to stimulate the release of LH or FSH, or interfering with a surface protein of a virus so that it is unable to infect cells, thereby inhibiting replication and infection by the virus. An effective amount may be administered as either a single dose of a vaccine or multiple doses of a vaccine.

As used herein, the phrases "amount effective to inhibit infection by the pathogen from which (b) is derived", "amount effective to inhibit BHV-1 infection", "amount effective to protect against infection", and the like, refer to that amount of fusion protein or vaccine capable of protecting a vertebrate from infection as defined above. An effective amount may be administered as either a single dose of a vaccine or multiple doses of a vaccine.

A "vertebrate", as used herein, refers to any species having a backbone or spinal column, namely fish, amphibians, reptiles, birds, and mammals. Examples of vertebrates which can benefit from the vaccine of the subject invention include, but are not limited to, humans, chickens, pigs, dogs, cats cows, goats, sheep and horses, among others. Preferably, the vertebrate is a mammal.

The term "pathogenically infecting" as used herein refers to the ability of a pathogen to infect a vertebrate in a manner or to a degree that results in a detectable diseased condition in the vertebrate. BHV-1, for example, pathogenically infects cattle but not humans.

Peptides that can be used as a source for preparing a portion (a) of a fusion protein of the present invention include, but are not limited to the following: 1) cholecystokinen (Eng, J. et al., 1990, Regul. Pept. 30(1):15–9); a fusion protein of the present invention comprising a portion (a) analogous to all or part of cholecystokinen can be used to promote appetite in a vertebrate; 2) vasoactive intestinal peptide (Nilsson, A., 1975, FEBS Lett. 60(2):322–6), inhibition of which causes a decrease in prolactin secretion which in turn discourages brooding behavior in chickens, thus resulting in increased egg production; 3) growth hormone and growth hormone fragments (Seeburg, P. H. et al., 1983, DNA 2(1):37–45); a fusion protein enhancing the activity of growth hormone can promote growth in an animal; 4) growth hormone releasing hormone and fragments thereof (Gubler, U. et al., 1983, Proc. Natl. Acad. Sci. U.S.A. 80(14), 4311–4314); antibodies may also enhance the growth promoting activity of growth hormone releasing hormone; 5) gastrin (Dimaline, R. et al., 1986, FEBS Lett. 205(?):318–22; Kim, S. J. et al., 1991, DNA Seq. 1(3):181–7; Kariya, Y. et al., 1986, Gene 40(1–3):345–52) and gastrin releasing peptide (Spindel, E. R. et al., 1986, Proc. Natl. Acad. Sci. USA 83(1):19–23); a fusion protein inhibiting gastrin and/or gastrin releasing peptide activity is useful, inter alia, in inhibiting gastric secretions, and therefore in treating ulcers; treating stomach, small intestine and/or colon cancer; and in promoting appetite; 6) IgE peptides (Batista, F. D. et al., 1995, Nucleic Acids Res. 23(23):4805–11); fusion proteins inhibiting IgE are useful for alleviating and/or preventing allergies, especially allergic skin reactions; 7) an angiotensin peptide, including angiotensin peptides I, II, III, and IV (U.S. Pat. No. 5,612,360 to Boyd et al.; U.S. Pat. No. 5,599,663 to Vaughan; U.S. Pat. No. 5,629,292 to Rodgers and DiZerega; U.S. Pat. No. 5,635,359 to Brunner and Nussberger); a fusion protein inhibiting the activity of an angiotensin peptide is useful for treating, e.g., hypertension in a mammal; 8) myostatin (Kambadur, R. et al., 1997, Genome Res. 7(9):910–6); inhibiting myostatin activity enhances skeletal muscle growth in an animal, without harming meat quality, and therefore can be desirable for increasing meat production in an animal; 9) inhibin or fragments thereof (U.S. Pat. No. 5,786,179 to Kousoulas et al.; U.S. Pat. No. 5,665,568 to Mason and Seeburg); a fusion protein that inhibits the activity of inhibin can be used to treat infertility due to irregular production of follicle stimulating hormone in a female animal; 10) somatostatin (U.S. Pat. No. 5,422,110, above; Shen, L. P. et al., 1982, Proc. Natl. Acad. Sci. USA 79(15):4575–9; Su, C. J. et al., 1988, Mol. Endocrinol. 2(3):209–16); a fusion protein inhibiting somatostatin is useful, e.g., for stimulating growth; and 11) cytokine peptides such as tumor necrosis factor (U.S. Pat. No. 5,795,967 to Aggarwal et al.) and interlukin-1 (Masaaki, Y. et al., JP 1994073095-A 1 (Mar. 15, 1994)); inhibiting cytokine activity in an animal can alleviate immune-potentiated inflammation, for example inflammation associated with allergies. The preceding peptides, their amino acid sequences and physiological actions, are well known in the art. The aforementioned publications describing these peptides are hereby incorporated by reference in their entireties.

Examples of immunogens from which proteinaceous portions useful for portion (b) can be derived include, but are not limited to, the following immunogens: 1) OmpW (U.S. Provisional Patent Application No. 60/105,285, filed Oct. 22, 1998; encoded by plasmid pER418 present in host cells of strain Pz418 deposited with the American Type Culture Collection (otherwise known as the ATCC (Manassas, Va., USA) under ATCC Accession No. 98928; SEQ ID NO:44 (deduced amino acid sequence of OmpW)); OmpA1 (U.S. Provisional Patent Application No. 60/105,285, encoded by plasmid pER419 present in host cells of strain Pz419 deposited with the ATCC under ATCC Accession No. 98929; SEQ ID NO:45 (deduced amino acid sequence of OmopA1)); OmpA2 (U.S. Provisional Patent Application No. 60/105,285; encoded by plasmid pER420 present in host cells Pz420 deposited with the ATCC under the designation ATCC Accession No. 98930; SEQ ID NO:46 (deduced amino acid sequence of OmpA2)); OmlA serotype 1 and serotype 5 (U.S. Pat. No. 5,441,736 to Gerlach et al.); all from *Actinobacillus pleuropneumonia*; a proteinaceous portion analogous to all or part of OmpW, OmlA5 or OmpA can be used as a carrier in a fusion protein according to the present invention while simultaneously providing swine with protection against porcine pleuropneumonia (caused by *A. pleuropneumonia* infection); 2) hepatitis B surface antigen (Hsiung et at, 1984, J. Mol. Appl. Gen. 2:497); a proteinaceous portion analogous to all or part of a hepatitis B surface antigen can be used as a carrier in a fusion protein of the present while at the same time providing protection in humans against hepatitis B infection; 3) an RTX ("repeat in toxin") toxin from *Actinobacillus pleuropneumonia* (Frey, J. et al., 1991, Infect. Immun. 59(9), 3026–32); a proteinaceous portion analogous to all or part of an RTX toxin as a carrier in a fusion protein of the present invention can simultaneously provide immunoprotection against *Actinobacillus pleuropneumonia* in swine and cattle, 4) β subunit of *E. coli* heat labile enterotoxin (Leong, J. et al., 1985, Infect. Immun. 48(1):73–7; Inoue, T. et al., 1993, FEMS Microbiol. Lett 108(2):157–61); a portion analogous all or part of β subunit of *E. coli* heat labile enterotoxin can serve as a carrier that also provides immunoprotection against *E. coli* in swine and cattle; 5) *E. coli* antigens K88 pilus or K99 pilus (Bakker, D. et al., 1992, J. Bacteriol 174(20):6350–8; Simons, B. L. et al., 1990, FEMS Microbiol. Lett 55(102):107–12); a proteinaceous portion analogous to all or part of K88 pilus antigen or K99 pilus antigen as a carrier in a fusion proteins of this invention can provide protection against enteric *E. coli* disease in swine and cattle; 6) p68 antigen of *B. bronchiseptica* (WO 9115571-A 5 (Oct. 17, 1991)); a proteinaceous portion analogous to all or part of p68 antigen can be used as a carrier in a fusion protein of the present invention and can provide protection against bordetella infection ("kennel cough" disease) in canines; 7) glycoprotein 53 from bovine viral diarrhea (BVD) virus (Fritzemeier, J. et al., 1997, Arch. Virol. 142(7):1335–50); a portion analogous to all or part of glycoprotein 53 can serve as a carrier in a fusion protein and also provide protection from fatal mucosal disease in cattle; 8) viral proteins 1 and 2 of parvovirus(Xie, A. and Chapman, M. S., 1996, J. Mol. Biol. 264:497); a proteinaceous portion analogous to all or part of viral protein 1 or viral protein 2 from parvovirus can serve as a carrier in a fusion protein of the present invention and simultaneously protect swine, dogs and cats from parvovirus infection; 9) a coronavirus spike protein (Kokubu, T. et al., 1998, Journal of the Japan Veterinary Medical Association 51:252–55; Lewis, E. L., 1996, Bristol University Thesis (Bristol University (Clifton, Bristol, UK)); Britton, P. et al., 1991, Virus Res. 21(3):181–98); a portion analogous to all or part of a coronavirus spike protein can be used as a carrier in a fusion protein and also provides protection against Coronavirus infection in cattle, swine, dogs, and cats; 10) a bacterial iron-regulated outer membrane protein (Gerlach, G. F. et al., 1992, Infect. Immunol. 60(8):3253–61; Thompson, S. A. et al., 1993, Mol. Microbiol. 9(1):85–96); a portion analogous to all or part of such a membrane protein can be used as a carrier that also provides immunoprotection against *Actinobacillus pleuropneumonia* and/or meningitis in swine, cattle and poultry; 11) rabies G protein (Shinichi, S. et al., JP 1989171489-A 1 (Jul. 6, 1989)); a proteinaceous portion analogous to all or part of rabies G protein can be used as a carrier in a fusion protein and will also simultaneously provide protection in cats, dogs, and wildlife against rabies; 12) *Streptococcus uberis* plasminogen activating protein (Leigh, J. A. 1993, WO 9314209); a proteinaceous portion analogous to all or part of *Streptococcus uberis* plasminogen activating protein is useful as a carrier and also will provide treatment and/or protection against mastitis in dairy cows; 13) influenza virus hemagglutinin protein (Hovanec, D. L. and Air, G. M., 1984, Virology 139(2) :384–92) and influenza virus nucleocapsid protein (Lindstrom, S. E. et al., 1998, J. Virol. 72(10):8021–31); a portion analogous to all or part of either of these proteins can be used as a carrier in a fusion protein of this invention and will simultaneously provide immunoprotection against influenza in humans, swine, and poultry; 14) tetanus toxoid (Fairweather, N. F. et al, 1986, J. Bacteriol. 165(1):21–7; Niemann, H., 1986, EMBO J. 5(10):2495–502); a proteinaceous portion analogous to all or part of tetanus toxoid can be used as a carrier in a fusion protein that will also provide protection in humans, horses, and cattle against tetanus; 15) pertussis toxoid (Nicosia, A. et al., 1986, Proc. Natl. Acad. Sci. USA 83(13):4631–5); a proteinaceous portion analogous to all or part of pertussis toxoid can serve as a carrier in a fusion protein and will provide immunoprotection against pertussis in humans; 16) a herpes virus glycoprotein (Gompels, U. A. et al., 1992, DNA Seq. 3(1):25–39; Misra, V. et al., 1988, Virology 166:542–9; Whitbeck, J. C., et al., 1988, J. Virol. 62:3319–27; Fitzpatrick, D. R. et al., 1989, Virology 173:46–57); a proteinaceous portion analogous to all or part of a herpes virus glycoprotein can serve as a carrier in a fusion protein of this invention and can function also in the fusion protein to provide immunoprotection from herpes in humans and cattle; 17) enterohemorrhagic *E. coli* intimin protein (Jerse, A. E. et al., 1990, Proc. Natl. Acad. Sci. USA 87(20):783–943); a portion analogous to all or part of enterohemorrhagic *E. coli* intimin protein can function as a carrier and also provide protection against hemorrhagic disease in species including humans and cattle; 18) VP2 (Cao, Y. C. et al., 1995, Ping Tu Hsueh Pao 11(3):234–41); a portion analogous to all or part of VP2 can function as a carrier and can also provide immunoprotection against infectious bursa disease in poultry; and 19) F and G proteins of respiratory syncitial virus (Schrijver, R. S. et al., 1997, Archives of Virology 142(11):2195–2210; Furze, J. M. et al., 1997, Virology 231(1):48–58); a proteinaceous portion analogous to all or part of F protein or G protein can act as a carrier and will also provide immunoprotection against Bovine Respiratory Syncytial Virus in cattle. The preceding immunogens and their amino acid sequences are known in the art. The aforementioned publications describing the preceding immunogens are hereby incorporated by reference in their entireties.

Different proteinaceous portions (a) and (b), each portion analogous to all or part of a peptide or immunogen described in one of the preceding paragraphs or another known peptide or immunogen, can be combined according to the present invention to form a fusion protein specifically designed for a particular vertebrate, e.g,. a cow, pig, chicken, or human, or a particular category of vertebrates, e.g., mammals or primates, to inhibit the activity of a particular peptide in the vertebrate while simultaneously protecting the vertebrate from infection by a certain pathogen.

As an example, GnRH is a reproductive system hormone synthesized by cattle. Inhibiting GnRH activity in cattle will provide a beneficial reduction in expression of sexual characteristics such as aggressive behavior. Since BHV-1 pathogenically infects cattle, an immunogen from BHV-1 can be used as a carrier with GnRH Thus, in one embodiment, a portion (a) analogous to all or part of a GnRH peptide and a portion (b) analogous to all or part of an immunogen from BHV-1 are connected to provide a fusion protein that induces a dual immune response in cattle that both inhibits GnRH activity and protects against BHV-1 infection.

In another non-limiting example, the subject invention provides a fusion protein wherein portion (a) is analogous to all or part of a growth hormone, and wherein portion (b) is analogous to all or part of a BHV-1 antigen. Such a fusion protein is useful to regulate growth in cattle while providing a protective immune response against BHV-1.

In another example, portion (a) is analogous to all or part of an IgE peptide and portion (b) is analogous to all or part of p68 antigen of *B. bronchiseptica*. The resulting fusion protein is useful for treating or preventing allergies, especially allergic skin reactions, in dogs while providing a protective immune response against bordetella.

In still another example, portion (a) is analogous to all or part of cholecystokinen and portion (b) is analogous to all or part of OmpW, OmlA serotype 1, OmlA serotype 5, Omp A1, or OmpA2 from *Actinobacillus pleuropneumonia*. Such a fusion protein is useful for encouraging appetite in swine while simultaneously providing a protective immune response against porcine *pleuropneumonia*.

The proteinaceous portions (a) and (b) for the fusion proteins of the invention can be obtained according to methods known in the art. For example, either or both of portion (a) or portion (b) can be obtained by purification from natural sources. Alternatively, either or both of portion (a) or portion (b) can be obtained by synthetically linking amino acids together. Alternatively, either or both of portion (a) or portion (b) can be recombinantly synthesized using well-known recombinant techniques from a polynucleotide molecule comprising a nucleotide sequence encoding the portion (a) or the portion (b). Preferably, a polynucleotide molecule comprising a nucleotide sequence encoding portion (a) is ligated to a polynucleotide molecule comprising a nucleotide sequence encoding portion (b), so that the entire fusion protein is synthesized recombinantly.

Recombinant techniques within the ordinary skill in the art can be utilized to prepare polynucleotide molecules that encode portions (a) and (b) of the subject fusion proteins.

Such techniques are described, among other places, in Maniatis, et al., 1989, *Molecular Cloning, A Laboratory Manual*, Cold Spring Harbor Laboratory Press, Cold Spring Harbor, N.Y.; Ausubel, et al., 1989, *Current Protocols in Molecular Biology*, Greene Publishing Associates & Wiley Interscience, NY; Sambrook, et al., 1989. *Molecular Cloning: A Laboratory Manual*, 2d ed., Cold Spring Harbor Laboratory Press, Cold Spring Harbor, N.Y.; Innis et al., (eds), 1995, *PCR Strategies*, Academic Press, Inc., San Diego; and Erlich (ed), 1992, PCR Technology, Oxford University Press, New York, all of which are incorporated herein by reference.

The amino acid sequences of many hormone peptides are well known in the art. Some known hormone peptides are described above. As another example, the amino acid sequence of GnRH is known in the art (see, e.g., Ladd, A., 1993, above). The amino acid sequence of GnRH is also provided herein (SEQ ID NO: 13). Alternatively, if the amino acid sequence of a hormone is not known, it may be determined using standard techniques, such as by performing repeated Edman degradation cycles on a purified protein fraction followed by amino acid analysis using HPLC (high pressure liquid chromatography) (see, e.g., U.S. Pat. No. 5,422,110, above). Likewise, a proteinaceous portion which is the same or substantially the same as an immunogen from a pathogen can be obtained according to standard techniques, from a known amino acid sequence or by ascertaining the amino acid sequence as described above. A proteinaceous portion that is substantially the same as an immunogen from a pathogen can be determined, for example, by comparing the amino acid content of the proteinaceous portion to the known amino acid content of the immunogen, or by performing a sequence alignment comparing the proteinaceous portion to the immunogen amino acid sequence, using known techniques.

Examples of BHV-1 antigens from which proteinaceous portion (b) can be derived include, but are not limited to, BHV-1 gB, BHV-1 gC, and BHV-1 gD (also known in the art as BHV-1gI, gIII and gIV, respectively). Methods for obtaining proteinaceous portions which are analogous to all or part of such antigens are described above. For example, U.S. Pat. No. 5,151,267 to Babiuk et al. discloses the nucleotide sequences and deduced amino acid sequences of BHV-1 g9, gIII, and gIV. See, also, U.S. Pat. No. 5,585,264 to Babiuk et al. In addition, U.S. Pat. No. 5,545,523 to Batt et al. discloses BHV-1-specific oligonucleotides useful in the amplification of BHV-1 gI and gIV gene sequences. Furthermore, methods of purifying BHV-1 glycoproteins from virus-infected cell cultures have been described (Babiuk, L. A. et al., 1987 Virology 159:57–66). The amino acid sequence of full length BHV-1 gD as published in Tikoo et al., 1990, above, is provided herein (see FIG. 5 and SEQ ID NO: 19). Expression of full length mature BHV-1 gD has been performed in baculovirus, adenovirus, vaccinia virus and *E. coli* systems (van Drunen Littel-van den Hurk, S. et al., 1993, Vaccine 11:25–35). The disclosures and teachings of the aforementioned patents and publications are incorporated herein by reference. Another example of a BHV-1 gD antigen which is useful, in whole or in part, for a fusion protein of the subject invention is the BHV-1 gD polyaminoacid encoded by clone, FlgD/Pots207nco(#79) (see FIG. 3 and SEQ ID NO: 17).

Although any part of a BHV-1 antigen which is able to stimulate an immune response that inhibits the peptide from which portion (a) is derived and, as in the first aspect of the invention, an immune response that protects a cow from BHV-1 infection can be used in the fusion proteins of this invention, examples of preferred parts of BHV-1 gD which can be used in this invention are truncated gD (tgD), mature gD (mgD), and truncated mature gD (tmgD). Truncated gD (tgD) refers to a gD protein wherein the transmembrane domain, optionally with downstream and/or upstream nucleotides, has been completely or partially removed. The transmembrane domain for gD is known in the art as a particular polyaminoacid region of gD of generally highly hydrophobic amino acids. The transmembrane domain of gD/Pots, BHV-1 gD encoded by clone FlgD/Pots207nco (#79), is depicted in FIG. 3. The transmembrane domain for gD/Pots starts at amino acid 364 (valine) and ends at amino acid 389 (tyrosine). Mature gD refers to a gD protein which has no signal sequence at the amino-terminal end. The signal sequence of full length gD/Pots is depicted in FIG. 3. In another embodiment, the proteinaceous portion (b) of the fusion protein of the subject invention can comprise a heterologous signal sequence attached to the amino terminal end of the protein. Alternatively, portion (b) can comprise no signal sequence. In one embodiment of the invention, portion (b) is analogous to a BHV-1 gD which is both truncated and mature (tmgD). An example of a truncated mature gD antigen is provided in SEQ ID NO: 35. An example of truncated gD antigen that is not mature is provided in SEQ ID NO: 29.

As used herein, "tgD" refers to a BHV-1 gD protein which is truncated as described above, "mgD" refers to a BHV-1 gD protein which is mature as described above, and "tmgD" refers to a BHV-1 gD protein which is both truncated and mature.

The term "GnRH peptide" means, unless otherwise indicated, a molecule having the amino acid sequence of SEQ ID NO: 13. In one embodiment, the subject fusion proteins comprise multiple portions (a) analogous to a GnRH peptide. In preferred embodiments, the fusion proteins of this invention comprise one or more portions analogous to four GnRH peptides consecutively linked, i.e., one or more portions analogous to a GnRH tetramer. In a preferred embodiment, a fusion protein of the present invention comprises a 4GnRH portion. As used herein, "4GnRH" refers to a GnRH tetramer having four GnRH peptides consecutively linked in the same amino-terminal/carboxy-terminal orientation. Preferably, the fusion proteins of the subject invention comprise one or more GnRH tetramers, each tetramer having the amino acid sequence shown in SEQ ID NO: 15.

Hyphenated expressions provided herein and containing the terms "4GnRH", "tmgD", "tgD", and "mgD" (as defined above) indicate fusion proteins which comprise polyaminoacid portions corresponding to the terms linked from left to right in the order indicated, the left end corresponding to the amino terminal end of the fusion protein and the right end corresponding to the carboxy terminal end of the fusion protein. The polyaminoacid portions can be directly linked to one another or they can be linked indirectly, i.e. the portions can be separated by one or more (for example from 1 to 10, preferably from 1 to 3) amino acids. Thus, "tmgd-4GnRH" refers to a fusion protein having a truncated mature go portion connected, directly or indirectly, to a 4GnRH portion, the carboxy terminal end of the truncated mature gD portion being linked (directly or indirectly) to the amino terminal end of the 4GnRH. As another example, "tgD4GnRH" refers to a fusion protein having the amino terminal end of 4GnRH portion connected to the carboxy terminal end of a truncated gD antigen which is not mature. As another example, "4GnRH-tmgD-4GnRH" refers to a 4GnRH portion having a carboxyl end linked to the amino end of a tmgD portion, which tmgD portion in turn is linked by its carboxyl end to the amino end of a second 4GnRH portion. Fusion proteins of the subject invention include, but are not limited to, the examples of fusion proteins described in this paragraph. Another example of a fusion protein of this invention is tmgD-4GnRH. In any of the aforementioned examples, the portions can be linked directly or indirectly.

As discussed above, proteinaceous portions (a) and (b) can be connected chemically by means of chemical linkers and techniques which are well known in the art. As an example, certain amino acids on a portion (a) or (b), for example on a gD analog (b) portion, may be chemically activated with a reagent, such as iodoacetamide. Remaining portions (a) or (b), for example GnRH monomers and/or multimers, may be added. In this example, terminally incorporated cysteine residues on GnRH react with activated lysine residues on the gD analog. This reaction results in fusion proteins according to the subject invention which comprise a central gD analog portion having multiple GnRH analogs connected thereabout at several lysine residues. In another example, portions (b) analogous to a BHV-1 antigen may be combined together with portions (a) analogous to GnRH monomers or multimers in the presence of ethyl-dimethylaminopropylcarbodiimide (EDAC) and N-hydroxy succinimide (NHS) (see Bernatowics, M. and Matsueda, G., 1986, Analytical Biochemistry 155:95–102). This reaction also results in a central portion (b) analogous to all or part of a BHV-1 antigen with multiple portions (a) analogous to GnRH monomers or multimers chemically connected thereabout. The chemically synthesized fusion proteins of the present invention can also optionally be chemically modified to comprise substituents other than amino acids, for example carbohydrate substituents, using known techniques. Other chemical techniques for combining proteinaceous portions, either with multiple attachments to a proteinaceous center or linear linkages of proteinaceous portions, can be used to chemically synthesize fusion proteins of the present invention using known techniques. Techniques for preparing chemically-synthesized fusion proteins of the present invention are described, among other places, in Dunn and Pennington, 1994, *Methods in Molecular Biology*, Vol. 26, Chap. 10 (Humana Press Inc.), which is incorporated herein by reference.

The subject invention also provides recombinant fusion proteins as described above. Examples of recombinant fusion proteins according to the present invention include the recombinant fusion protein encoded by the plasmid pCMV-gD:GnRH the plasmid pQE-gD:GnRH, the recombinant fusion protein encoded by the plasmid pQE-GnRH:gD:GnRH, and the recombinant fusion protein encoded by the plasmid pQE-GnRH:gD. Cells containing these plasmids have been deposited with the American Type Culture Collection (ATCC Manassas, Va., USA); they have been assigned accession numbers 203370, 98953, 98955, and 98954, respectively. Another example of a recombinant fusion protein of the subject invention, is the recombinant fusion protein expressed by the baculovirus construct Bac-gD:GnRH. Bac-gD:GnRH has also been deposited with the ATCC and has been assigned ATCC accession number VR-2633. The aforementioned pQE plasmids and baculovirus construct are particularly useful for in vitro expression of fusion proteins. The plasmid pCMV-gD:GnRH is particularly useful for in vivo expression.

Recombinant fusion proteins according to this invention may optionally comprise portions which assist in purifying the fusion proteins from the reaction medium pursuant to in vitro transcription and translation. An example of a polyaminoacid sequence which can assist in purification of a recombinant protein from the medium is a 6×HIS tag. The phrase "6×HIS tag" is used interchangeably in this application with "6×HIS leader". The sequence of the 6×HIS tag encoded by the vector pQE-31 is provided in SEQ. ID NO: 37. Proteins comprising a 6×HIS tag can be purified from the media by passing the media through a nickel column such as Ni-NTA column from Qiagen (Chatsworth, Calif.). Another example of a portion that can assist in purifying recombinant fusion proteins of this invention pursuant to in vitro expression is the FLAGTM epitope tag (International Biotechnologies Inc., New Haven, Conn.) which is a hydrophilic marker peptide. The gene encoding the FLAG™ epitope tag can be inserted by standard techniques into a polynucleotide molecule comprising a nucleotide sequence encoding a fusion protein of this invention at a point corresponding, e.g., to the amino or carboxyl terminus of the fusion protein. A fusion protein expressed therefrom can then be detected and affinity-purified using commercially available anti-FLAG™ antibodies.

Other means of purifying recombinant proteins expressed in vitro are well-known in the art and can be used to purify the recombinant fusion proteins of the subject invention. Such methods are described, among other places, in Marshak, D. R., et al., 1996, *Strategies for Protein Purification and Characterization: a Laboratory Course Manual*, Cold Spring Harbor Laboratory Press, Cold Spring Harbor, N.Y.

Once a fusion protein of the present invention has been obtained, it can be characterized if desired by standard methods, including by SDS-PAGE, size exclusion chromatography, amino acid sequence analysis, etc. The fusion protein can be further characterized using hydrophilicity analysis (see, e.g., Hopp and Woods, 1981, Proc. Natl. Acad. Sci. USA 78:3824), or analogous software algorithms, to identify hydrophobic and hydrophilic regions. Structural analysis can be carried out to identify regions of the fusion protein that assume specific secondary structures. Biophysical methods such as X-ray crystallography (Engstrom, 1974, Biochem. Exp. Biol. 11: 7–13), computer modeling (Fletterick and Zoller (eds), 1986, in: *Current Communications in Molecular Biology*, Cold Spring Harbor Laboratory, Cold Spring Harbor, N.Y.), and nuclear magnetic resonance (NMR) can be used to map and study potential sites of interaction between the polypeptide and other putative interacting proteins receptorslmolecules such as antibodies.

Polynucleotide Molecules and Vectors Encoding Fusion Proteins

The subject invention further provides a polynucleotide molecule comprising a nucleotide sequence encoding a fusion protein of the present invention. Examples of such polynucleouide molecules include, but are not limited to, a polynucleotide molecule comprising the nudeotide sequence set forth in SEQ ID NO: 34, which encodes a 4GnRH-tmgD fusion protein; a polynucleotide molecule comprising the nucleotide sequence set forth in SEQ ID NO: 40, which encodes a 4GnRH-tmgD-4GnRH fusion protein; and a polynucleotide molecule comprising the nucleotide sequence set forth in SEQ ID NO:41, which encodes a tmgD-4GnRH fusion protein.

The subject invention also provides cloning and expression vectors comprising a polynucleotide molecule comprising a nucleotide sequence encoding a fusion protein of the invention. The term "vector", as used herein, means a unit comprising genetic information (in the form of polynucleotide sequences), which information is able to express polyaminoacids and/or program the replication of the unit when appropriate conditions and resources (e.g. amino acids, nucleotides, and transcription factors) are present. Examples of such units include viruses, plasmids, and cosmids.

As used herein, the terms "nucleotide sequence", "coding sequence", "polynucleotide", "polynucleotide sequence", and the like, refer to both DNA and RNA sequences, which can either be single-stranded or double-stranded, and can include one or more prokaryotic sequences, eukaryotic sequences, cDNA sequences, genomic DNA sequences, including exons and introns, and chemically synthesized DNA and RNA sequences.

Production and manipulation of polynucleotide molecules of the subject invention comprising nucleotide sequences encoding portions (a) and (b) of the subject fusion proteins are within the ordinary skill in the art and can be carried out according to recombinant techniques described, among other places, in Maniatis, et al., above; Ausubel, et al., above; Sambrook, et al., above; Innis et al., above; and Erlich, above. Nucleotide sequences encoding many hormone peptides and viral antigen peptides are known in the art, and such information can be used to prepare coding regions for the proteinaceous portions (a) and (b). Such sequences are provided, among other places, in the references cited above describing immunogens and peptides useful in the present invention. Alternatively, the nucleotide sequences of peptides and viral antigens can be deduced using known methods in molecular biology.

Nucleotide sequences encoding portion (a) and/or portion (b) can be synthetically prepared. The desired sequence can be prepared from overlapping oligonucleotides. See, e.g., Edge, 1981, Nature 292:756; Nambair et al., 1984 Science 223:1299; Jay et al., 1984, J. Biol. Chem. 259:6311; and U.S. Pat. No. 5,422,110, above.

As another example, the amino acid sequence of a peptide or antigen can be used to design probes for identifying the gene encoding the peptide or antigen in a genomic library. In this method, oligonucleotide probes are prepared encoding a portion of the amino acid sequence of the peptide or antigen. The oligonucleotide probes are used to screen a suitable DNA library for genes encoding the peptide or the antigen. Generally, the DNA library which is screened is a library prepared from genomic DNA or genomic RNA (cDNA) from an appropriate source, such as from a cell or tissue expressing the peptide or from a virus encoding the antigen. Techniques for isolating genes in this manner are well-known in the art.

Nucleotide sequences homologous to sequences obtained as described herein to encode immunogens or peptides can also be utilized in the present invention. For purposes of the subject invention, a second nucleotide sequence is "homologous" to a first nucleotide sequence when it encodes the same protein, peptide, or other polyaminoacid as the first nucleotide sequence, or when it encodes a polyaminoacid that is sufficiently similar to the polyaminoacid encoded by the first nucleotide sequence so as to be useful in practicing the present invention. Since the genetic code is degenerate, a homologous nucleotide sequence can include any number of "silent" base changes, i.e. nucleotide substitutions that nonetheless encode the same polyaminoacid. A homologous nucleotide sequence can further contain non-silent mutations, i.e. base substitutions, deletions, or additions resulting in amino acid differences in the encoded polyaminoacid, so long as the sequence of the polyaminoacid remains useful for practicing the present invention. A second nucleotide sequence that is homologous to a first nucleotide sequence is preferably one that hybridizes to the complement of the first nucleotide sequence under moderately stringent conditions, i.e., hybridization to filter-bound DNA in 0.5 M $NaHPO_4$, 7% sodium dodecyl sulfate (SDS), 1 mM EDTA at 650° C., and washing in 0.2×SSCl0.1% SDS at 42° C. (see Ausubel et al., above). More preferably, homologous nucleotide sequences hybridized to one another under highly stringent conditions, i.e., hybridization to filter-bound DNA in 0.5 M $NaHPO_4$, 7% SDS, 1 mM EDTA at 65° C., and washing in 0.1×SSC/0.1% SDS at 68° C. (Ausubel et al., above).

After having obtained polynucleotide molecules comprising nucleotide sequences encoding portions (a) and (b), these polynucleotide molecules can be ligated together using suitable enzymes and known techniques to form a polynucleotide molecule comprising a nucleotide sequence encoding a fusion protein of this invention.

Examples of coding sequences useful in constructing polynucleotide molecules comprising sequences encoding fusion proteins of the present invention, and vectors comprising such polynucleotide molecules, include, but are not limited to, the sequence presented in SEQ ID NO: 16, which encodes the BHV-1 gD antigen FlgD/Pots expressed by clone FlgD/Pots207nco(#79), set forth in SEQ ID NO: 17; the sequence presented in SEQ ID NO: 18, which encodes M59846 BHV-1 gD, set forth in SEQ ID NO: 19; the sequence presented in SEQ ID NO: 28, which encodes a truncated gD antigen that is not mature, set forth in SEQ ID NO: 29; and the sequence presented in SEQ ID NO: 36, which encodes a truncated mature gD, set forth in SEQ ID NO: 35. An example of a nucleotide sequence that encodes a GnRH monomer is set forth in SEQ ID NO: 33. An example of a sequence which encodes a GnRH tetramer, namely the GnRH tetramer having the amino acid sequence set forth in SEQ ID NO: 15, is set forth in SEQ ID NO: 32.

In one embodiment, a vector of the subject invention is suitable for in vitro expression of a fusion protein, such as a plasmid which is capable of transfecting a host cell such as a bacterial cell and expressing the fusion protein in the bacterial cell. Examples of plasmid vectors include plasmids, such as recombinant pQE plasmids, capable of transfecting bacteria and expressing the fusion proteins of this invention. Examples of some prokaryotic expression vector plasmids into which a polynucleotide molecule comprising a nucleotide sequence encoding a fusion protein of the invention can be inserted include pQE-50 and pQE-31 (Qiagen, Chatsworth, Calif.), pUC8, pUC9, pBR322 and pBR 239 (Biorad Laboratories, Richmond, Calif.), pPL and pKK223 (Pharmacia, Piscataway, N.J.). Other plasmids known in the art can also be used to prepare vectors comprising a polynucleotide molecule comprising a nucleotide sequence encoding a fusion protein of this invention, and such plasmids can be ascertained by those of ordinary skill. Preferred plasmids which are capable of expressing fusion proteins of the invention in vitro include pQE-gD:GnRH (ATCC Accession No. 98953), pQE-GnRH:gD:GnRH (ATCC Accession No. 98955), and pQE-GnRH:gD (ATCC Accession No. 98954). These plasmids are able to express fusion proteins of this invention in E. coli bacteria.

In another embodiment, a vector of the subject invention is a plasmid suitable for in vivo expression of a fusion protein. Plasmids which are able to transfect eukaryotic cells, and which can be used to construct vectors of the subject invention, can be ascertained by those of ordinary skill in the art. Such plasmids can comprise sequences and encode elements which assist in the in vivo expression and processing of the fusion proteins in a vaccinated vertebrate.

For example, a plasmid of the present invention can comprise a eukaryotic promoter sequence. As another example, a plasmid of the present invention can comprise a sequence encoding a signal attached to the expressed fusion protein, which signal results in the transportation of the expressed fusion protein to the cell membrane and excretion of the fusion protein from the cell into the vaccinated vertebrate's circulatory system. An example of a plasmid which can be used to construct vectors of the subject invention capable of expressing fusion proteins in vivo is pCMV (Clontech, Inc., Palo Alto, Calif.). Other typical eukaryotic expression plasmids that can be engineered to comprise a polynucleotide molecule comprising a nucleotide sequence encoding a fusion protein of the present invention include an inducible mammalian expression system and the cytomegalovirus promoter-enhancer-based systems (Promega, Madison, Wis.; Stratagene, La Jolla, Calif.; Invitrogen). Other plasmids useful for preparing vectors expressing fusion proteins of the subject invention in vivo can be ascertained by those of ordinary skill in the art. A preferred example of a plasmid of the subject invention capable of in vivo expression of a fusion protein is pCMV-gD:GnRH which has been deposited with the ATCC (ATCC Accession No. 203370).

Vectors of the subject invention also include recombinant viruses which comprise a polynudeotide molecule comprising a nucleotide sequence encoding a fusion protein of the present invention. Such viruses can be prepared according to techniques known in the art. They may, for example, be prepared from bacteriophage, the resulting recombinant bacteriophage being useful for expressing and producing the subject fusion proteins in vitro in bacteria. Examples of bacteriophage which can be used to prepare vectors of this invention include T4, T7, φX174, G4, M13, and fd. Other bacteriophage useful for the subject invention may be ascertained by those of ordinary skill in the art.

Recombinant viruses capable of transfecting insect cells or yeast cells can also be constructed for in vitro expression and production of fusion proteins of this invention in insect cells and yeast cells, respectively. In this regard, another example of a vector which can be used for in vitro production of the fusion proteins of this invention is a recombinant virus based on a baculovirus. In preferred embodiments, the subject invention provides baculovirus vectors, which express tmgD-4GnRH, 4GnRH-tmgD-4GnRH, or 4GnRH-tmgD. In a preferred embodiment of this invention, the vector is the baculovirus vector Bac-gD:GnRH, which expresses a tmgD-4GnRH fusion protein. Bac-gD:GnRH has been deposited with the ATCC (ATCC Accession No. VR-2633).

Recombinant viruses capable of infecting and expressing the subject fusion proteins in eukaryotic cells, such as avian or mammalian cells, including viruses for both in vitro and in vivo expression of the fusion proteins in eukaryotic cells, can also be constructed according to techniques well known in the art. Examples of viruses from which such recombinant viruses can be prepared include poxviruses, such as vaccinia virus, and adenovirus. Both recombinant vaccinia virus and recombinant adenovirus can be used for either in vitro or in vivo expression. Other viruses suitable for expression in eukaryotic cells can be ascertained by those of ordinary skill in the art.

In another embodiment, a vector of the subject invention is a "transfer vector" comprising a potynucleotide molecule comprising a nucleotide sequence encoding a fusion protein of the subject invention. A transfer vector is a plasmid comprising a sequence encoding a peptide, which plasmid can infect a suitable host cell, such as a suitable insect or mammalian cell, in an in vitro co-infection process with a virus, causing the host cell to produce a recombinant virus, which recombinant virus is itself a vector that is capable of expressing the peptide encoded by the plasmid in a suitable expression system. Preparation of transfer vectors for in vitro production of recombinant virus is well known in the art, and plasmids which are useful for preparing transfer vectors according to this subject invention can be ascertained by those of ordinary skill in the art. Examples of plasmids suitable for preparing transfer vectors include, but are not limited to, pBacPAK8 and pBacPAK 9 (Clontech, Inc.). A preferred transfer vector for preparing a viral vector encoding a fusion protein of the subject invention is the transfer vector pBacHISgD:GnRH.

The nucleotide sequence which encodes a fusion protein of the present invention can be ligated to and placed under the control of various nucleotide elements, such as signal sequences, inducible and non-inducible promoters, ribosome binding sites for bacterial expression, and operators. Such elements permit the nucleotide sequence to be transcribed, either in vivo or in vitro, in a host cell transfected with a vector comprising the polynucleotide molecule, and accordingly to be cloned or expressed in the host cell. Regulatory sequences and enhancer sequences can also be included in the polynucleotide molecules of the invention. The coding sequences are placed in "operative association" with the elements that are included in the polynucleotide molecules, which means that their placement and orientation is such that transcription of the coding sequences can occur. Such placement is within the ordinary skill in the art.

Regulatory elements of polynucleotide molecules of the present invention can vary in their strength and specificities. Depending on the host/vector system to be utilized, any of a number of suitable transcription and translation elements can be used. For instance, when cloning in mammalian cell systems, promoters isolated from the genome of mammalian cells, e.g., mouse metallothionein promoter, or from viruses that grow in these cells, vaccinia virus 7.5K promoter or Moloney murine sarcoma virus long terminal repeat, can be used. Promoters obtained by recombinant DNA or synthetic techniques can also be used to provide for transcription of the inserted sequence. In addition, expression from certain promoters can be elevated in the presence of particular inducers, e.g., zinc and cadmium ions for matallothionein promoters. Non-limiting examples of transcriptional regulatory regions or promoters include, for bacteria, the β-gal promoter, the T7 promoter, the T5 promoter, the TAC promoter, λ left and right promoters, trp and lac promoters, trp-lac fusion promoters, etc.; for yeast, glycotytic enzyme promoters, such as ADH-I and -II promoters, GPK promoter, PGI promoter, TRP promoter, etc.; and for mammalian cells, SV40 early and late promoters, adenovirus major late promoters, among others.

Specific initiation signals can also be used for translation of inserted coding sequences. These signals typically include an ATG initiation codon and adjacent sequences. In cases where the polynucleotide molecule of the present invention includes its own initiation codon and adjacent sequences are inserted into the appropriate expression vector, no additional translation control signals may be needed. However, in cases where only a portion of a coding sequence is inserted, exogenous translational control signals, including the ATG initiation codon, may be required. These exogenous translational control signals and initiation codons can be obtained from a variety of sources, both natural and synthetic. Furthermore, the initiation codon must be in phase with the reading frame of the coding regions to ensure in-frame translation of the entire insert.

Vectors of this invention can also include repressor genes and operators, which regulate the transcription of mRNA. Examples of operators which can be included in the subject vectors include the lac operator sequence. Other operators are known in the art, and can be included in the vectors of this invention.

Expression vectors can also contain a polynucleotide molecule of this invention which is further engineered to contain polylinker sequences that encode specific protease cleavage sites so that the expressed fusion protein can be released from expressed vector sequences by treatment with a specific protease. For example, the fusion protein vector can include a nucleotide sequence encoding a thrombin or factor Xa cleavage site, among others.

Expression vectors of the subject invention can also comprise nucleotide sequences that encode a polyaminoacid that can assist in purification of a fusion protein from media following expression. An example of such a nucleotide sequence is a nucleotide sequence encoding a 6×HIS tag, such as the nucleotide sequence set forth in SEQ ID NO: 38.

Transformed Cells for Expressing Fusion Proteins

The subject invention also provides transformed cells which comprise a polynucleotide molecule comprising a nucleotide sequence encoding a fusion protein as described herein. Cells useful for transformation for this invention include bacterial cells, yeast cells, mammalian cells, insect cells, and plant cells. Transformed cells of this invention can be prepared by transfecting a cell with a vector comprising a polynucleotide molecule comprising a nucleotide sequence encoding the fusion protein as described above.

Host cells useful in practicing the subject invention can be eukaryotic or prokaryotic. Such transformed host cells include, but are not necessarily limited to, microorganisms, such as bacteria, transformed with a recombinant bacteriophage or plasmid; yeast transformed with a recombinant vector; animal cells, such as mammalian cells, infected with a recombinant virus vector, e.g., adenovirus or vaccinia virus, among others; and insect cells transformed with a recombinant virus vector, e.g. a baculovirus vector.

For expression and harvesting of fusion proteins in vitro, bacterial cells can be used as host cells. For example, a strain of $E.$ $coli$ can be used, such as, e.g., the DH5α strain available from the ATCC, Rockville, Md., USA (ATCC Accession No. 31343) or from Stratagene (La Jolla, Calif.) or the BL21 strain available from microorganism depositories such as the ATCC. Eukaryotic host cells, including yeast cells and vertebrate cells, e.g., from a mouse, hamster, cow, monkey, or human cell line, among others, can also be utilized effectively. Examples of eukaryotic host cells that can be used to express a fusion protein of the invention include Chinese hamster ovary (CHO) cells (e.g., ATCC Accession No. CCL-61), NIH Swiss mouse embryo cells NIH/3T3 (e.g., ATCC Accession No. CRL-1658), and Madin-Darby bovine kidney (MDBK) cells (ATCC Accession No. CCL-22).

Other cells that are particularly useful for in vitro expression and harvesting of fusion proteins of this invention are cells which possess a system for glycosylation of amino acids of proteins. Some examples of cells that have a glycosylation system are insect cells, mammalian cells and yeast cells. Systems from different cell types can provide different patterns of glycosylation for a fusion protein of the invention.

The recombinant vector of the invention is preferably transformed or transfected into one or more host cells of a substantially homogeneous culture of cells. The vector can be introduced into host cells in accordance with known techniques, such as, e.g., by protoplast transformation, calcium phosphate precipitation, calcium chloride treatment, microinjection, electroporation, transfection by contact with a recombined virus, liposome-mediated transfection, DEAE-dextran transfection, transduction, conjugation, or microprojectile bombardment, among others. Selection of transformants can be conducted by standard procedures, such as by selecting for cells expressing a selectable marker, e.g., antibiotic resistance, associated with the recombinant expression vector.

Once an expression vector is introduced into the host cell, the integration and maintenance of the polynucleotide sequence encoding a fusion protein of the present invention, either in the host cell genome or episomally, can be confirmed by standard techniques, e.g., by Southern hybridization analysis, restriction enzyme analysis, PCR analysis including reverse transcriptase PCR (rt-PCR), or by immunological assay to detect the expected fusion protein product. Host cells containing a polynucleotide coding sequence and/or expressing a fusion protein of the present invention can be identified by any of at least four general approaches that are well-known in the art, including: (i) DNA-DNA, DNA-RNA, or RNA-antisense RNA hybridization; (ii) detecting the presence of "marker" gene functions; (iii) assessing the level of transcription as measured by the expression of specific mRNA transcripts in the host cell; or (iv) detecting the presence of mature polypeptide product, e.g., by immunoassay, as known in the art.

Once a polynucleotide sequence encoding a fusion protein of the present invention has been stably introduced into an appropriate cell, the transformed cell can be clonally propagated, and the resulting cells can be grown under conditions conducive to the maximum production of the encoded fusion protein. Such conditions typically include growing transformed cells to high density. Where the expression vector comprises an inducible promoter, appropriate induction conditions such as, e.g., temperature shift, exhaustion of nutrients, addition of gratuitous inducers (e.g., analogs of carbohydrates, such as isopropyl-5-D-thiogalactopyranoside (IPTG)), accumulation of excess metabolic by-products, or the like, are employed as needed to induce expression.

Where the recombinantly-expressed fusion protein is retained inside the host cells, the cells are harvested and lysed, and the product is purified from the lysate under extraction conditions known in the art to minimize protein degradation such as, e.g., at 4° C., or in the presence of protease inhibitors, or both. Where the recombinantly-expressed fusion protein is secreted from the host cells, the exhausted nutrient medium can simply be collected and the fusion protein isolated therefrom.

The recombinantly-expressed fusion protein can be purified from cell lysates or culture medium, as necessary, using standard methods, including but not limited to one or more of the following methods: ammonium sulfate precipitation, size fractionation, ion exchange chromatography, HPLC, density centrifugation, and affinity chromatography. The recombinantly-expressed fusion protein can be detected based, e.g., on size, or reactivity with a fusion-protein-specific antibody, or by the presence of a fusion tag, e.g. a 6×HIS tag. The present invention encompasses recombinantly-expressed fusion protein in an unpurified state, as secreted into the culture fluid or as present in a cell lysate, as well as partially or substantially purified recombinant fusion protein, all being useful for practicing the present invention.

Vaccines, including Dual-Function Vaccines, and Methods Using Same

Fusion protein, vectors, and transformed cells of the present invention can be used to prepare dual-function vaccines to induce an immunoinhibitory response in a vertebrate against the peptide to which portion (a) of the subject fusion proteins is analogous, while simultaneously protecting against infection by the pathogen from which portion (b) is derived. Such vaccines are also useful in a vertebrate solely for inhibiting a peptide to which portion (a) is analogous.

Thus, in one aspect, this invention provides a dual-function vaccine which comprises a fusion protein as described above, or a vector or a transformed cell comprising a polynucleotide molecule comprising a nucleotide sequence encoding such a fusion protein, in an amount effective to inhibit the activity of the peptide from which portion (a) is derived and to protect against infection by the pathogen from which portion (b) is derived in a vertebrate which endogenously synthesizes the peptide and which can be pathogenically infected by the pathogen, along with a carrier acceptable for pharmaceutical or veterinary use.

In a preferred embodiment, the subject invention provides a dual-function vaccine for inhibiting GnRH activity in cattle while simultaneously protecting cattle from BHV-1 infection, which comprises a fusion protein according to the subject invention, or a vector or transformed cell comprising a polynucleotide molecule comprising a nucleotide sequence encoding such a fusion protein, wherein portion (a) of the fusion protein is analogous to all or part of a GnRH peptide and wherein portion (b) is analogous to all or part of a BHV-1 antigen, the fusion protein being present in an amount effective to inhibit GnRH activity in cattle and to also protect cattle from BHV-1 infection, along with a carrier acceptable for veterinary use.

The subject invention also provides a method for inhibiting the activity of an endogenously-synthesized peptide in a vertebrate and for protecting the vertebrate from a pathogenic infection which comprises immunizing the vertebrate with an amount of a dual-function vaccine as described above, which amount is effective to inhibit the activity of the peptide and to protect against infection by the pathogen. In a preferred embodiment, the subject invention provides a method for inhibiting sexual characteristics and for protecting against BHV-1 infection in a cow, which comprises vaccinating the cow with a dual-function vaccine as described above comprising a fusion protein comprising a portion (a) analogous to all or part of a GnRH peptide and a portion (b) analogous to all or part of a BHV-1 antigen, or vector or transformed cell comprising a polynucleotide molecule comprising a nucleotide sequence encoding such a fusion protein, in an amount effective to inhibit sexual characteristics and protect against BHV-1 infection.

In vaccines which comprise a fusion protein of the invention wherein portion (b) is analogous to all or part of a BHV-1 antigen, the vertebrate which is vaccinated need not be a vertebrate which BHV-1 is capable of pathogenically infecting. In such vertebrates, portion (b) simply acts as a carrier to induce an immune response inhibiting the peptide to which it is connected.

Thus, the subject invention also provides a vaccine for inhibiting the activity of a peptide in a vertebrate which comprises a fusion protein of the invention wherein portion (a) is analogous to all or part of a peptide and portion (b) is analogous to all or part of a BHV-1 antigen, or a vector or transformed cell comprising a polynucleotide molecule comprising a nucleotide sequence encoding such a fusion protein, in an amount effective to inhibit the activity of the peptide, along with a carrier acceptable for pharmaceutical or veterinary use.

In a preferred embodiment, the invention provides a vaccine for inhibiting the activity of GnRH in a vertebrate which comprises a fusion protein wherein portion (a) is analogous to all or part of a GnRH peptide and portion (b) is analogous to all or part of a BHV-1 antigen, or vector or transformed cell comprising a polynucleotide molecule comprising a nucleotide sequence encoding such a fusion protein, in an amount effective to inhibit GnRH activity, along with a carrier acceptable for pharmaceutical or veterinary use.

The subject invention also provides a method for inhibiting the activity of a peptide, including, but not limited to, the hormone GnRH, in a vertebrate, which comprises immunizing the vertebrate with an amount of the above described vaccine comprising a fusion protein, or a vector or transformed cell comprising a polynucleotide molecule comprising a nucleotide sequence encoding such a fusion protein, which fusion protein comprises a proteinaceous portion analogous to all or part of a BHV-1 antigen as a carrier, which amount is effective to inhibit the activity of the peptide.

The subject invention also provides a method for inhibiting sexual characteristics in a vertebrate, preferably a mammal, which comprises immunizing the vertebrate with an amount of a vaccine comprising a fusion protein comprising a portion (a) analogous to all or part of a GnRH peptide and a portion (b) analogous to all or part of a BHV-1 antigen, or a vector or transformed cell comprising a polynudeotide molecule comprising a nucleotide sequence encoding such a fusion protein, which amount is effective to inhibit sexual characteristics. The vertebrate need not be a member of the bovine species, but can be any vertebrate in which GnRH is endogenously synthesized, such as a sheep, pig, horse, goat, dog, cat, or human.

"Sexual characteristics" refers to those characteristics in a vertebrate associated with the vertebrate's gender and/or the vertebrate's ability to reproduce, which characteristics are induced, either in whole or in part, either directly or indirectly, by GnRH. Such characteristics are ascertainable by those of ordinary skill in the art. In male cattle, examples of inhibition of such sexual characteristics include repression of aggressive behavior. suppression of testosterone production, reduced libido, regression of the accessory sex glands (including prostates and seminal vesicles), diminution in the testicular volume, and reduction or cessation of spermatogenesis. In female cattle, inhibition of such sexual characteristics include failure to ovulate and infertility, regression of the reproductive tract, and abortion. In one embodiment, GnRH is inhibited in either a male or a female vertebrate such that the sexual characteristics which are inhibited include a functional reproductive system, the present invention thus providing a form of contraception.

The subject invention also provides a method for inhibiting abnormal cell growth in prostate tissue in a male vertebrate, preferably in a mammal, which comprises immunizing the vertebrate with an amount of a vaccine comprising a fusion protein, or a vector or transformed cell comprising a polynucleotide molecule comprising a nucleotide sequence encoding such a fusion protein, which fusion protein comprises a portion (a) analogous to all or part of a GnRH peptide and a portion (b) analogous to all or part of a BHV-1 antigen, which amount is effective to inhibit abnormal prostate cell growth.

Vaccines of the present invention can be formulated following accepted convention to include acceptable carriers for animals, including humans, such as standard buffers, stabilizers, diluents, preservatives, and/or solubilizers, and can also be formulated to facilitate sustained release. Diluents include water, saline, dextrose, ethanol, glycerol, and the like. Additives for isotonicity include sodium chloride, dextrose, mannitol, sorbitol, and lactose, among others. Stabilizers include albumin, among others. Other suitable vaccine vehicles and additives, including those that are particularly useful in formulating modified live vaccines, are known or will be apparent to those skilled in the art. See, e.g., Remington's *Pharmaceutical Science,* 18th ed., 1990, Mack Publishing, which is incorporated herein by reference.

Vaccines of the present invention can further comprise one or more additional immunomodulatory components such as, e.g., an adjuvant or cytokine, cholera toxin (CT) or heat labile toxin (LT) among others. Non-limiting examples of adjuvants that can be used in the vaccine of the present invention include the RIBI adjuvant system (Ribi Inc., Hamilton, Mont.), alum, mineral gels such as aluminum hydroxide gel, oil-in-water emulsions, water-in-oil emulsions such as, e.g., Freund's complete and incomplete adjuvants, Block copolymer (CytRx, Atlanta Ga.), QS-21 (Cambridge Biotech Inc., Cambridge Mass.), SAF-M (Chiron, Emeryville Calif.), AMPHIGEN® adjuvant, saponin, Quil A or other saponin fraction, monophosphoryl lipid A, and Avridine lipid-amine adjuvant. Non-limiting examples of oil-in-water emulsions useful in the vaccine of the invention include modified SEAM62 and SEAM 1/2 formulations. Modified SEAM62 is an oil-in-water emulsion containing 5% (v/v) squalene (Sigma), 1% (v/v) SPANS® 85 detergent (ICI Surfactants), 0.7% (v/v) TWEEN® 80 detergent (ICI Surfactants), 2.5% (v/v) ethanol, 200 µg/ml Quil A, 100 µg/ml cholesterol, and 0.5% (v/v) lecithin. Modified SEAM 1/2 is an oil-in-water emulsion comprising 5% (v/v) squalene, 1% (v/v) SPAN® 85 detergent, 0.7% (v/v) Tween 80 detergent, 2.5% (v/v) ethanol, 100 µg/ml Quil A, and 50 µg/ml cholesterol. Other immunomodulatory agents that can be included in the vaccine include, e.g., one or more interleukins, interferons, or other known cytokines. Where the vaccine comprises live transformed cells, the adjuvant is preferably selected based on the ability of the resulting vaccine formulation to maintain at least some degree of viability of the live transformed cells.

A vaccine comprising transformed cells of the present invention can be prepared by standard techniques, for example using an aliquot of culture fluid containing said transformed cells, either free in the medium or residing in mammalian host cells, or both, that can be administered directly, or in concentrated form, to the subject. Attentively, modified live transformed cells can be combined with a carrier acceptable for pharmaceutical or veterinary use, with or without an immunomodulatory agent, selected from those known in the art and appropriate to the chosen route of administration, where at least some degree of viability of the live cells in the vaccine composition is maintained. Such methods are known in the art.

Where a vaccine of this invention comprises live transformed cells, the vaccine can be stored cold or frozen. Where the vaccine composition comprises a fusion protein, vector, or inactivated transformed cells of the present invention, the vaccine may be stored frozen, or in lyophilized form to be rehydrated prior to administration using an appropriate diluent.

Vaccines of the present invention can optionally be formulated for sustained release of the fusion protein. Examples of such sustained release formulations include fusion protein in combination with composites of biocompatible polymers, such as, e.g., poly(lactic acid), poly(lactic-co-glycolic acid), methylcellulose, hyaluronic acid, collagen and the like. The structure, selection and use of degradable polymers in drug delivery vehicles have been reviewed in several publications, including A. Domb et al., 1992, Polymers for Advanced Technologies 3: 279–292, which is incorporated herein by reference. Additional guidance in selecting and using polymers in pharmaceutical formulations can be found in the text by M. Chasin and R. Langer (eds), 1990, "Biodegradable Polymers as Drug Delivery Systems" in: *Drugs and the Pharmaceutical Sciences,* Vol. 45, M. Dekker, N.Y., which is also incorporated herein by reference. Alternatively, or additionally, the fusion protein, vector, or transformed cells can be microencapsulated to improve administration and efficacy. Methods for microencapsulating antigens are well-known in the art, and include techniques described, e.g., in U.S. Pat. Nos. 3,137,631; 3,959,457; 4,205,060; 4,606,940; 4,744,933; 5,132,117; and International Patent Publication WO 95/28227, all of which are incorporated herein by reference.

Liposomes can also be used to provide for the sustained release of fusion protein, vector, or transformed cell. Details concerning how to make and use liposomal formulations can be found in, among other places, U.S. Pat. Nos. 4,016,100; 4,452,747; 4,921,706; 4,927,637; 4,944,948; 5,008,050; and 5,009,956, all of which are incorporated herein by reference.

An effective amount of any of the above-described vaccines can be determined by conventional means, starting with a low dose of fusion protein, vector, or transformed cell and then increasing the dosage while monitoring the effects. An effective amount may be obtained after a single administration of a vaccine or after multiple administrations of a vaccine. Known factors may be taken into consideration when determining an optimal dose per animal. These include the species, size, age and general condition of the animal, the presence of other drugs in the animal, and the like. The actual dosage is preferably chosen after consideration of the results from other animal studies.

One method of detecting whether adequate immune response has been achieved is to determine seroconversion and antibody titer in the animal after vaccination. The timing of vaccination and the number of boosters, if any, will preferably be determined by a qualified scientist or veterinarian based on analysis of all relevant factors, some of which are described above.

The effective dose amount of fusion protein, vector, and transformed cell of the present invention can be determined using known techniques, taking into account factors that can be determined by one of ordinary skill in the art such as the weight of the animal to be vaccinated. The dose amount of fusion protein of the present invention in a vaccine of the present invention preferably ranges from about 1 µg to about 10 mg, more preferably from about 50 µg to about 1 mg, and most preferably from about 100 µg to about 0.5 mg. The dose amount of a vector of the present invention in a vaccine of the present invention preferably ranges from about 50 µg to about 1 mg. The dose amount of transformed cells of the present invention in a vaccine of the present invention preferably ranges from about $1 \times 10^3$ to about $1 \times 10^8$ cells/ml, and more preferably from about $1 \times 10^5$ to about $1 \times 10^7$ cells/ml. A suitable dosage size ranges from about 0.5 ml to about 10 ml, and more preferably from about 1 ml to about 5 ml.

Where inhibiting abnormal cell growth in prostate is concerned, an effective amount of any of the above-described vaccines can be determined by conventional means, starting with a low dose of fusion protein, vector, or transformed cell and then increasing the dosage while monitoring the effects. Known factors can be taken into consideration when determining an optimal dose per animal. Some factors are described above.

"Abnormal cell growth" means cell growth which is independent of normal regulatory mechanisms (e.g., loss of contact inhibition). This includes the abnormal growth of: (1) malignant prostate tumor cells, such as prostate carcinoma cells, (2) benign cells of other proliferative disorders in prostate tissue, and (3) any other unregulated cell growth in prostate tissue associated with GnRH activity. "Inhibiting prostate carcinoma growth" and like phrases as used herein mean slowing, halting, and/or reversing abnormal cell growth in prostate tissue.

The present invention further provides a method of preparing a vaccine comprising a fusion protein as described above, which method comprises combining an effective amount of a fusion protein of the present invention, with a carrier acceptable for pharmaceutical or veterinary use.

Antibodies

The subject invention further provides a method of making polyclonal antibodies directed against a peptide that is endogenously synthesized in a vertebrate which comprises vaccinating such a vertebrate with an antibody-inducing amount of a fusion protein of the present invention, or a vector or transformed cell comprising a polynucleotide molecule comprising a nucleotide sequence encoding such a fusion protein, which fusion protein comprises a portion (a) analogous to all or part of a peptide endogenously synthesized within the vertebrate; obtaining serum containing polyclonal antibodies from the vaccinated vertebrate; and isolating from the serum polyclonal antibodies which bind to the endogenously-synthesized peptide; thereby making polyclonal antibodies directed against the peptide. Methods for obtaining serum from a vaccinated vertebrate and for isolating specific polyclonal antibodies therefrom are known in the art. In a preferred embodiment, the fusion protein comprises a portion (a) analogous to all or part of a GnRH peptide, and the peptide against which polyclonal antibodies are made is GnRH. The subject invention further provides polyclonal antibodies directed against an endogenously-synthesized peptide made according to this method. In a preferred embodiment, the polyclonal antibodies are directed against GnRH.

The subject invention further provides a method of making a monoclonal antibody directed against a peptide that is endogenously synthesized in a vertebrate which comprises vaccinating such a vertebrate with an antibody-inducing amount of a fusion protein of the present invention, or vector or transformed cell comprising a polynucleotide molecule comprising a nucleotide sequence encoding such a fusion protein, which fusion protein comprises a portion (a) analogous to all or part of a peptide endogenously synthesized within the vertebrate; and isolating a spleen cell from the vaccinated vertebrate which spleen cell excretes a monoclonal antibody that specifically binds to the endogenously-synthesized peptide; thereby making a monoclonal antibody directed against the peptide. In a preferred embodiment, the fusion protein comprises a portion (a) analogous to all or part of a GnRH peptide, and the peptide against which the monoclonal antibody is made is GnRH. The subject invention further provides monoclonal antibodies directed against an endogenously-synthesized peptide made according to this method. In a preferred embodiment, the monoclonal antibodies are directed against GnRH.

Methods for isolating spleen cells from a vaccinated animal which excrete a specific monoclonal antibody for purposes of making a monoclonal antibody are known in the art. Such methods include, but are not limited to, the hybridoma technique originally described by Kohler and Milstein (Nature, 1975, 256: 495–497); the human B-cell hybridoma technique (Kosbor et al., 1983, Immunology Today 4:72; Cote et al., 1983, Proc. Natl. Acad. Sci. USA 80: 2026–2030); and the EBV-hybridoma technique (Cole, et al., 1985, *Monoclonal Antibodies and Cancer Therapy*, Alan R. Liss, Inc., pp. 77–96). These publications are incorporated herein by reference.

Techniques for the production of monoclonal antibodies and antibody fragments are additionally described, among other places, in Harlow and Lane, 1988, *Antibodies: A Laboratory Manual*, Cold Spring Harbor Laboratory, and in J. W. Goding, 1986, *Monoclonal Antibodies: Principles and Practice*, Academic Press, London, which are incorporated herein by reference.

The following examples are provided to merely illustrate aspects of the subject invention. They are not intended, and should not be construed, to limit the invention set forth in the claims and more fully described herein.

EXAMPLES

Example 1

Plasmids Expressing gD/GnRH Fusion Proteins

Construction of pQE-tmgD

Figure 3A:
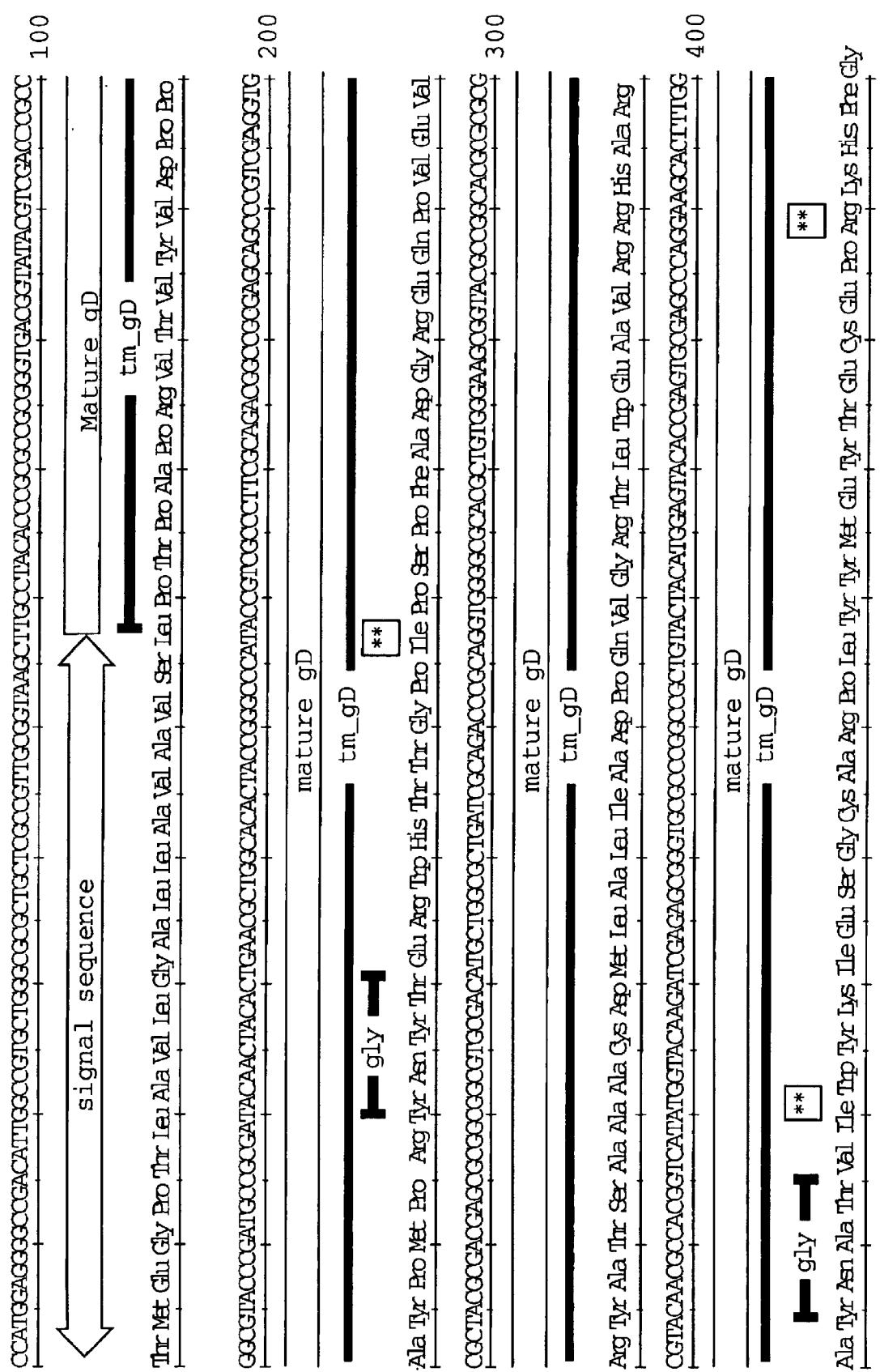
FIG. 3 (FIGS. 3A-3C): Nudeotide sequence (SEQ ID NO: 16) encoding BHV-1 gD within clone FlgD/Pots207nco (#79), as well as the encoded polyaminoacid gD sequence (SEQ ID NO: 17). Nucleotides 3–56 encode the signal sequence; nucleotides 1092–1169 encode the transmembrane domain. Nucleotides 57–1259 encode mature gD, and nucleotides 57–1076 encode truncated mature gD. "Gly" represents regions of glycosylation. Vector sequences flanking the gD coding sequence are shown.
Figure 3B:
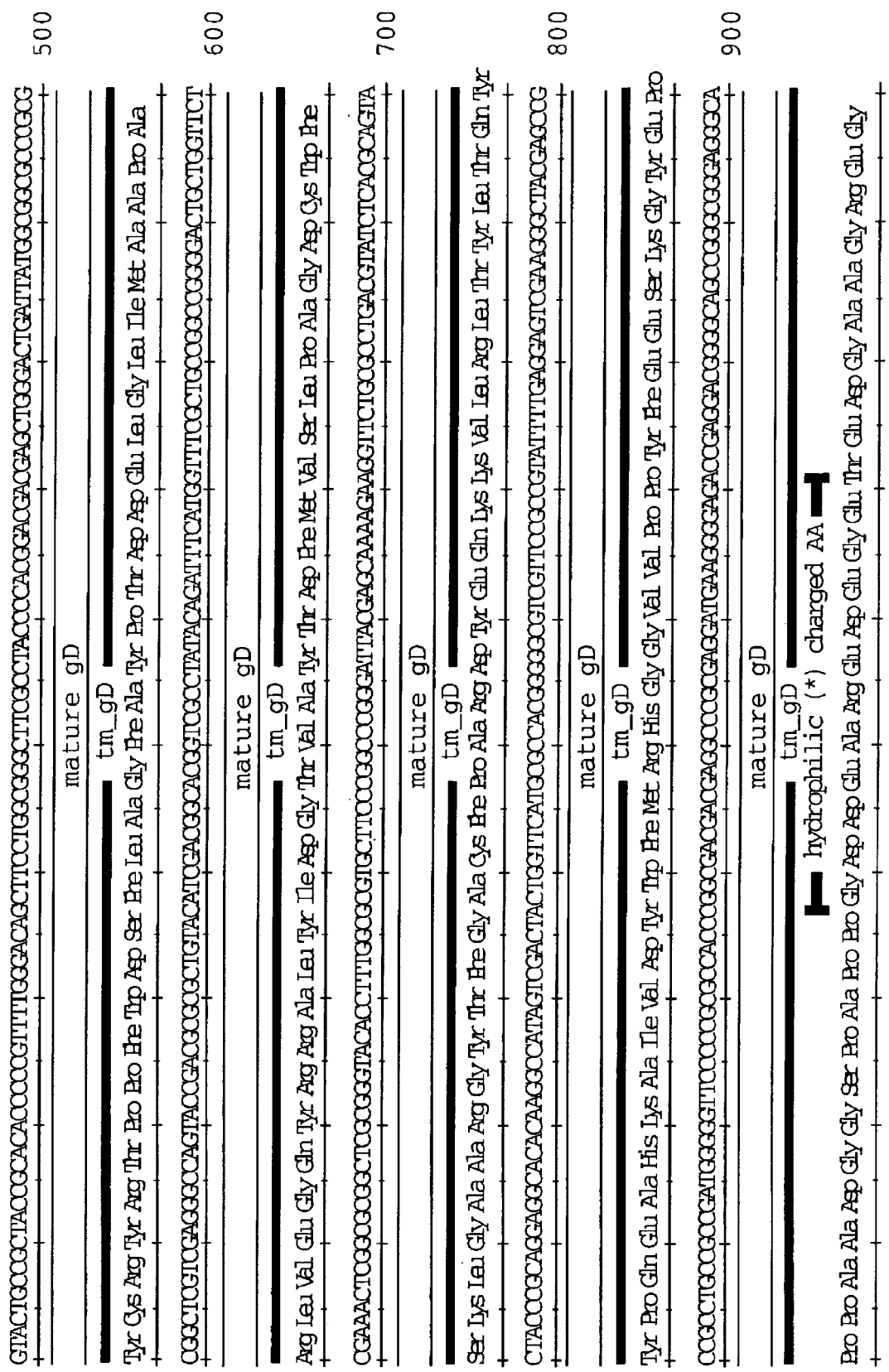
Figure 3C:
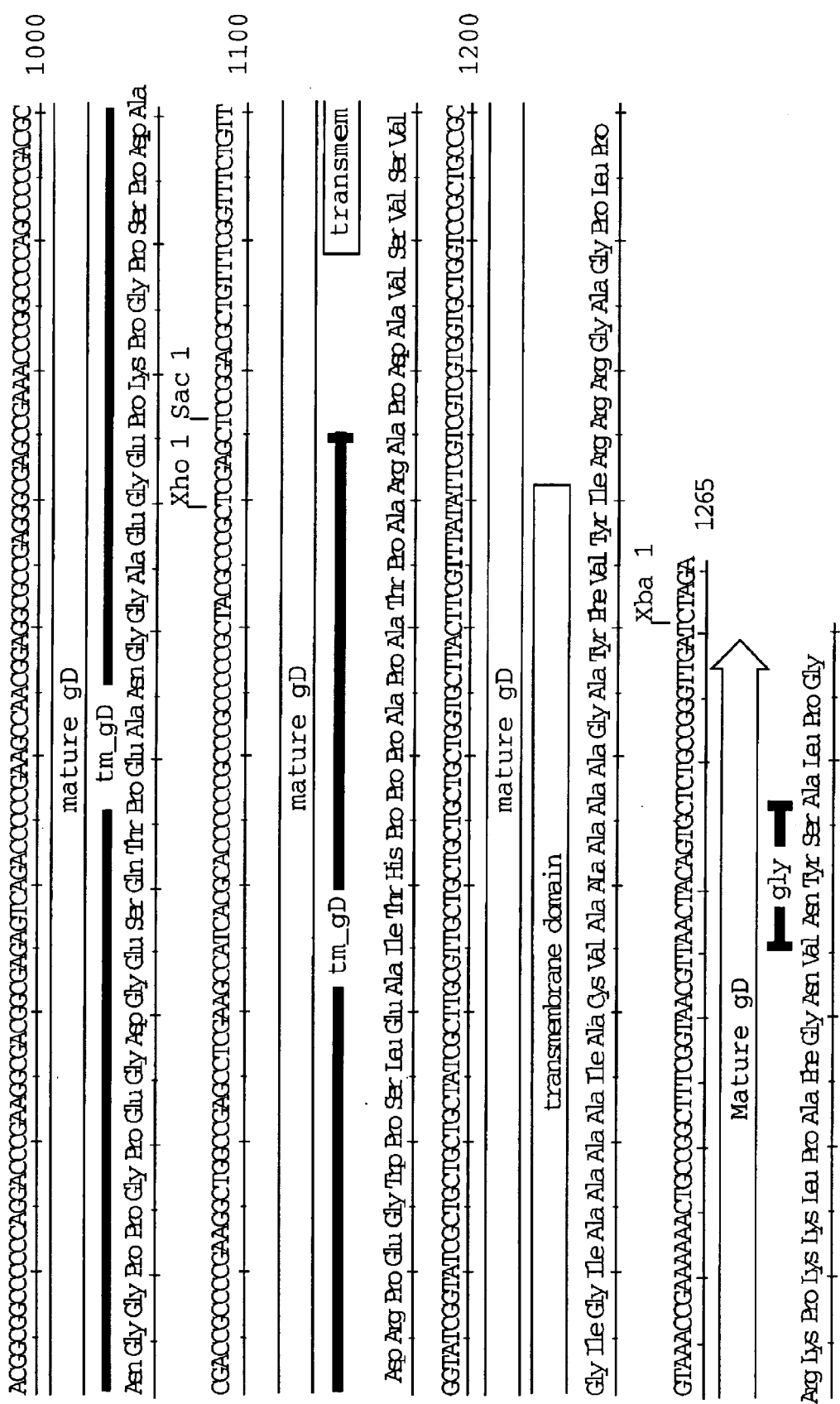

The plasmid FlgD/Pots207nco(#79) (encoding a full-length gD, hereinafter "gD/Pots") was digested with NcoI/XbaI and the resulung 1.26 kb fragment was cloned into the corresponding sites of pUC21, generating the plasmid pUC-FLgD. The complete sequence of the NcoI/XbaI fragment in the plasmid pUC-FLgD was determined on both DNA strands using Sanger fluorescent dideoxy chain termination sequencing technology. FIG. 3 shows the sequence results and characteristics. The nucleotide sequence encoding gD/Pots is included in SEQ ID NO: 16.

DNA alignment between gD/Pots and published BHV-1gD (GenBank Accession No. M59846) shows 94.7% homology with the majority of the mismatches occurring 3' of the transmembrane domain (FIG. 4).

Amino acid alignment between gD/Pots and M59846 shows four amino acid differences, one of which is located in the signal sequence and the other three in or around the transmembrane domain (FIG. 5).

The signal sequence for the gD protein was removed in order to facilitate expression of the protein in *E. coli*. The signal sequence removal was carried out by digesting pUC-FLgD plasmid DNA with Nco I/Hind III and filling in the ends with the Klenow fragment of DNA Polymerase I. The resulting DNA fragment was gel-purified and ligated. Colonies were screened for a shift in mobility of a Sph I/Sac I fragment that would indicate deletion of the 50 bp fragment. Two positive clones were selected and sequenced across the Nco I/Hind III deletion region. All clones were shown to have the correct sequence. Clone #1 was designated pUC-MgD was chosen for further manipulation.

The mature gD sequence was subcloned into an *E. coli* expression vector, for production of the protein on a large scale basis. To this end, a 1.07 kb Sph I/Sac I fragment from pUC-MgD containing the mature gD sequence (truncated at the 3' end to exclude the transmembrane domain) was subcloned into the corresponding sites of pQE-31 (Qiagen). (pQE-31 uses the phage T5 promoter and two lac operator sequences for greater repression before induction of expression with IPTG. pQE-31 also contains an N-terminal 6×HIS tag fusion for purification purposes.) The resulting clones were screened for the 1.07 kb SphI/SacI fragment. One positive clone, designated pQE-tmgD, was selected for preparation of further plasmids, infra. pQE-tmgD encodes an N-terminal 6×HIS tag fused to a truncated mature gD (tmgd) sequence, terminated by a vector-encoded stop codon following the Sac I site. The junction regions of the gD sequence and the plasmid backbone were sequenced to verify the integrity of the insert, and were found to be correct. The sequence encoding the tmgD (not including the 6×HIS tag) in pQE-tmgD is set forth in SEQ ID NO: 36. The amino acid sequence of the tmgD encoded by pQE-tmgD (without the 6×HIS tag) is set forth in SEQ ID NO: 35.

Construction of GnRH-tetramer Clones

Twelve different oligonucleotides (sense and complementary (reverse) strands) encoding GnRH (monomers and dimers) having different terminal DNA sequences were prepared. These twelve oligonucleotides are provided in SEQ ID NOS: 1–12.

Figure 1:
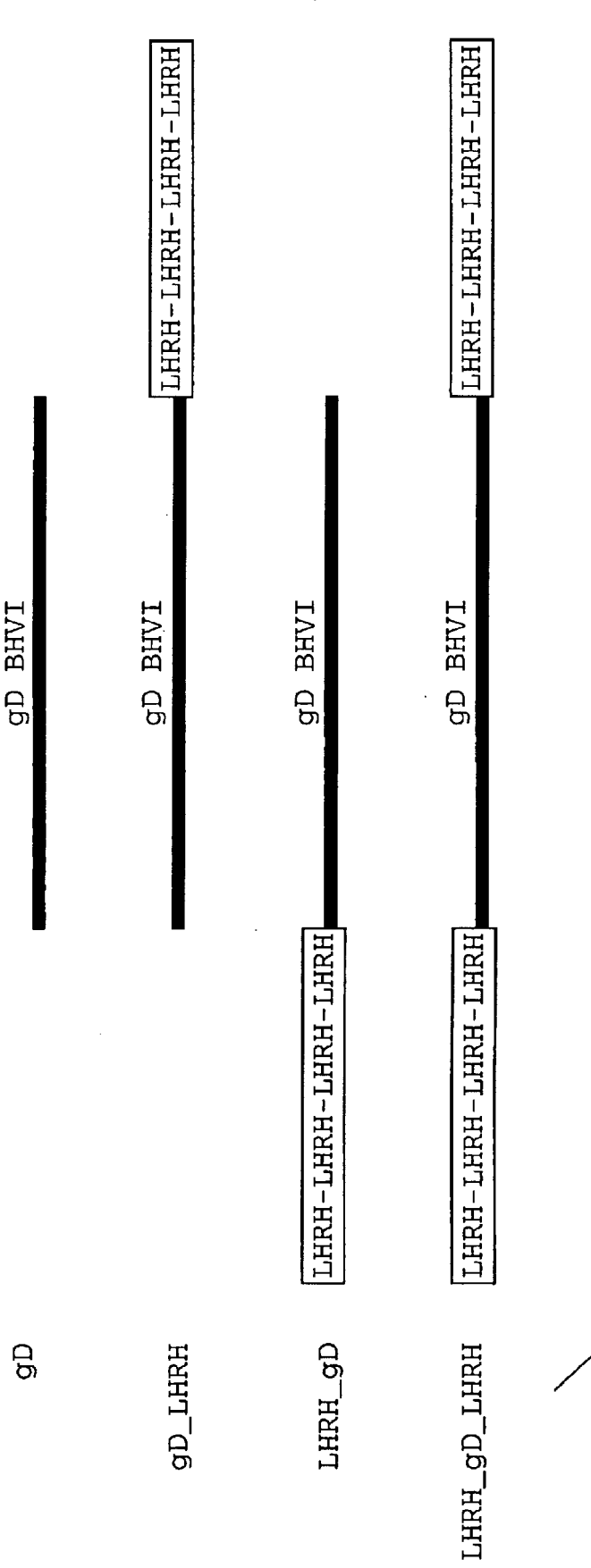
FIG. 1: Constructs of gD/GnRH fusions: fusion proteins constructed according to the subject invention are depicted. gD in these constructs is mature (the signal sequence has been removed) and truncated (the transmembrane domain and remaining 3' sequence has been removed). GnRH is in tetrameric form.
Figure 2:
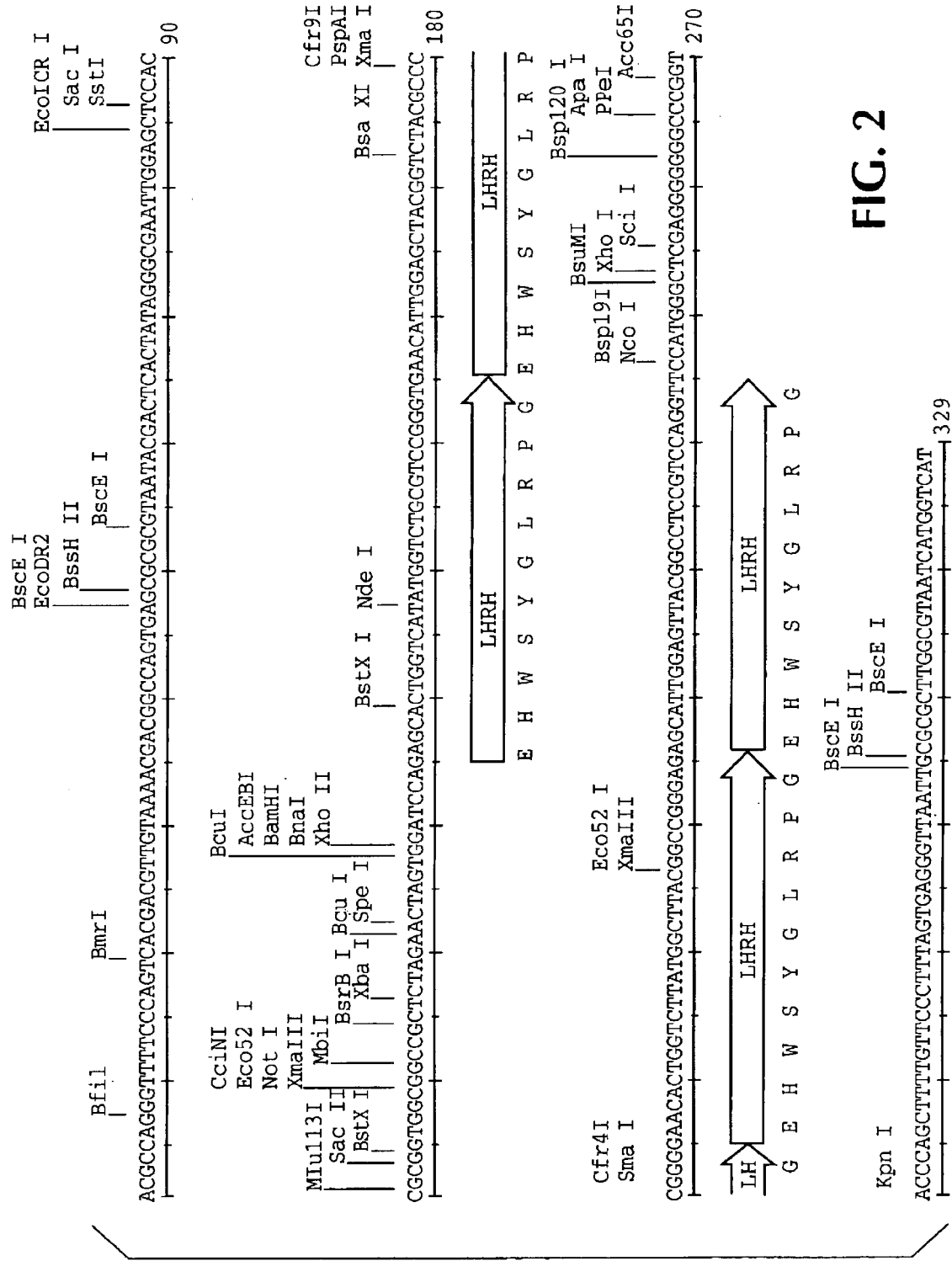
FIG. 2: A GnRH-tetramer clone, constructed by fusing the C termini of annealed GnRH oligonucleotides (set forth in SEQ ID NOS: 7 and 8) to the GnRH sequence (annealed oligonucleotides set forth in SEQ ID NOS: 9 and 10) in dimer clone 98BS/GnR. Flanking sequences from plasmid pBS KS+ (Stratagene) and cloning sites therein, are also depicted. This nucleotide sequence is set forth in SEQ ID NO: 14. The encoded amino acid sequence (SEQ ID NO: 15) is also shown.

Oligonucleotides 9 and 10 were annealed and cloned into the BamHi/XhoI sites of pBS KS+ (Stratagene), generating p98BS/GnRH. A plasmid encoding a GnRH tetramer was constructed from plasmid p98BS/GnRH by adding annealed oligonuceotides 7 and 8 at the Sma I/Xho I sites. A reconstruction of the full length tetramer was necessary because sequence analysis of 5 separate clones showed that all had base changes in the synthetic primer region. A clone containing the full length tetramer with the correct sequence was constructed by replacing a 106 bp Eag I fragment from one mutant clone with the corresponding fragment from a clone lacking base changes in this region. One of the resulting reconstructed clones was sequenced and found to have the correct DNA sequence encoding the GnRH tetramer. This clone contained one sequence difference from the predicted nucleotide sequence for the GnRH tetramer construct. The change is an additional G, 3' and outside the GnRH coding region, and, therefore, does not affect the coding region for GnRH. (The additional G was present in the clone used for the reconstruction, and is likely to be due to an error in the synthetic primer sequence.) This clone was designated p9897-R. A portion of p9897-R, including the sequence encoding the GnRH tetramer, is shown in FIG. 2. The sequence encoding the GnRH tetramer is set forth in SEQ ID NO: 32. The amino acid sequence of the GnRH tetramer encoded by p9897-R is set forth in SEQ ID NO: 33.

A PCR was employed using primers P14-S1 (SEQ ID NO:42) and P14-A138 (SEQ ID NO: 43) with template DNA from plasmid p9897-R to generate a 138bp fragment containing the GnRH tetramer PCR fragment having a 3' stop codon and synthetic 5' SacI and 3' HindIII ends. The PCR fragment was cloned into the pGEM-T EASY vector (Promega, Madison, Wis.), generating p9897 S/d3. The clone was sequenced and found to have the correct sequence. The clone, p9897 S/d3, provides a source for a GnRH tetramer coding sequence with SacI and HindIII ends for future cloning into pQE vectors.

Construction of pQEgD:GnRH

A 126 bp SacI/HindIII fragment from p9897 S/d3 containing the GnRH tetramer was cloned into the corresponding sites of plasmid pQE-tmgD. Colonies were screened for the presence of the 126 bp SacI/HindIII fragment and a 1165 bp BamHI/HindIII fragment indicating proper orientation of insert. The junction regions adjacent to the cloning sites were analyzed by DNA sequencing and found to be correct. The nucleotide sequence encoding tmgD-4GnRH, including the 6×HIS tag, and plasmid flanking sequences are set forth in SEQ ID NO: 24. The amino acid sequence of the tmgD-4GnRH encoded by pQE-gD:GnRH is set forth in SEQ ID NO: 25. As described above, tmgD-4GnRH is a fusion construct wherein a GnRH tetramer is fused to the carboxy terminus of truncated mature gD.

Construction of pQE-GnRH:gD

The GnRH tetramer coding sequence in p9897-R was cleaved with BamHI/NcoI, the ends blunted by filling in with Klenow, and the 132 bp fragment was gel purified. A mature gD vector fragment (i.e. without the signal sequence) was prepared by cleavage from pUC-FLgD with NcoI/HindIII, blunting the ends by filling in with Klenow, and gel purifying the 4.4 kb fragment. After ligation with the 132 bp fragment from p9897-R and transformation, clones were screened for the regeneration of the 5' BamH I and Nco I sites resulting from ligation in the correct orientation. Additional screening for the generation of an ~400 bp Nde I fragment confirmed the correct structure. The construct was sequenced across the GnRH/gD junctions to confirm the correct sequence. This construct, designated pUC-GnRH:gD, contains a GnRH tetramer sequence fused to the amino terminus of a mature full-length gD sequence in a pUC vector.

An 1161 bp GnRH tetramer/truncated mature gD fusion sequence was obtained by digesting pUC-GnRH:gD with Sph I and Sac 1 restriction enzymes. This 1161 bp fragment was cloned into the corresponding sites of pQE-31, generating pQE-GnRH:gD. Clones were screened for the 1161 bp Sph I/Sac I fragment, and for the correct pattern of Nde I fragments (380 bp, 2.0, 2.2 kb).

The nucleotide sequence encoding 4GNRH-tmgD, including the 6×HIS tag, and plasmid flanking sequences are set forth in SEQ ID NO: 22. The amino acid sequence of the 4GnRH-tmgD encoded by pQE-GnRH:gD is set forth in SEQ ID NO: 23.

Construction of pQE-GnRH:gD:GnRH

The 126 bp Sac I/Hind III fragment from p9897 S/d3 was subcloned into the corresponding sites of plasmid pQE-GnRH:gD, generating pQE-GnRH:gD:GnRH. Clones were screened for the 126 bp Sac I/Hind III fragment, as well as for the correct pattern of Nde I fragments.

pQE-GnRH:gD:GnRH encodes a 4GnRH-tmgD-4GnRH fusion protein. As described above, 4GnRH-tmgD-4GnRH comprises a truncated mature gD having a GnRH tetramer fused at both the amino and carboxy termini. The nucleotide coding sequence and flanking sequences from pQE-GnRH:gD:GnRH are provided in SEQ ID NO: 26. The amino acid sequence of the 4GnRH-tmgD-4GnRH encoded by pQE-GnRH:gD:GnRH, including the 6×HIS tag is set forth in SEQ ID NO: 27.

Comparison of Expression Products from Bacterial Expression Vector pQE Constructs All four constructs contained a tmgD derived from clone FlgD/Pots207nco(#79), which included amino acids 19 through 358 of FlgD/Pots207nco(#79).

All four constructs contained an amino terminal pQE-HIS leader sequence (a 6×HIS tag) denoted by amino acid designation: MRGSHHHHHHTDPHA (SEQ ID NO: 37). The coding sequence for the 6×HIS tag is set forth in SEQ ID NO:38.

All four constructs had a 2 or 3 amino acid linker after the 6×HIS leader sequence.

All GnRH products were derived from GnRH tetramer clone p9897-R.

The pQE-GnRH:gD and pQE-GnRH:gD:GnRH clones contained a three amino acid linker (SMS) between the amino terminal GnRH tetramer and the tmgD sequence.

The pQE-gD and pQE-GnRH:gD clones contained an extra ten amino acids at the carboxy terminal end of tmgd from the vector sequence as an artifact from cloning.

The pQE-gD:GnRH and pQE-GnRH:gD:GnRH clones contained a one amino acid (proline) linker between tmgD and GnRH carboxy fusion.

See FIG. 10 for an illustration of each of the pQE constructs.

Example 2

Expression of GnRH/gD Fusion Proteins by Transformed Bacterial Cells

All of the pQE constructs described in Example 1, above, were transformed into *E.coli* DH5α-F'IQ cells for expression. For induction of expression, cells were grown to an OD600 of 0.7–0.9 in a 2 liter baffled culture flask in 2×YT broth containing 100 μg/ml Ampicillin and 25 μg/ml Kanamycin, then induced with 1–2mM IPTG and incubated for 4 hours at 37 degrees Celsius. Average $OD_{600}$ readings at harvest time were 1.3. Expression of all four constructs was confirmed by Western blot analysis.

Example 3

Formulation of Fusion Protein Vaccines and Immunization of Mice

Vaccine Assembly

Fusion proteins from pQE-tmgD (as a control), pQE-GnRH:gD, pQE-GnRH:gD:GnRH, and pOE-gD:GnRH were concentrated from inclusion body preparations by preparative electrophoresis on 9% polyacrylamide gels. Bands cut from SDS PAGE gels were dissolved in 25 mM Tris, pH 8.3, 192 mM glycine and 0.1% SDS (w/v). The equivalent of 10 μgD/mouse dose was adjuvanted with SEAM1 (Squalene Emulsion Adjuvant Metabolizable) emulsion (10 μg QuilA/100 μl dose). Vaccine formulations were stored at 4° C. SEAM1 is 5% squalene, 0.1% Vitamin E acetate, 1% Span 85, 0.70% Tween 80, 2 mg/ml QuilA, and 400 μl/ml cholesterol.

Mice

BALB/c males were used in the study after they were 8 weeks of age (10/group). Mice were initially housed in groups of 10, however, controls were subsequently moved to individual cages to prevent fighting.

Immunization

Mice were immunized subcutaneously with 10 μg fusion protein in 100 μL adjuvant, described above. Three immunizations were given at study days 0, 20, and 41.

Anti-GnRH Antibodies by ELISA

Serum samples were collected at study days 0, 20, 31, 41, 55, 62, 69, and 146 and were evaluated for anti GnRH antibody titers in a peptide ELISA (enzyme linked immunoadsorbant assay). A biotinylated GnRH peptide (Biotin-GnRH) (0.1 μg/mL in 25 mM Tris, 0.15 M NaCl at pH 7.6) consisting of the natural sequence plus a 4 amino acid linker (CAGAEHWSYGLRPG), purified by HPLC on a reverse phase column, was adsorbed to avidin coated plates and incubated at room temperature for 2 hours. Excess peptide was removed by washing plates four times with the wash buffer (25 mM Tris, 0.15M NaCl, 0.05% Tween-20 and 0.05% BSA (bovine serum albumin) fraction V). Then, five-fold serial dilutions of positive control, negative and unknown mouse sera in diluent (25 mM Tris, 0.15 M NaCl, 0.05% BSA) (100 μl/well) were added to the peptide coated wells and incubated for 30 minutes at room temperature. Plates were washed four times in wash buffer and then rabbit anti mouse IgG (IgG specific)horseradish peroxidase (Zymed, Calif.) was added to each well (1:4,000, 100 μl/well). After incubation for 30 minutes at room temperature the bound antibody was detected with 3,3'5,5'-tetramethyl benzidine substrate (Kierkegaard & Perry, cat#50-76-04) (100 μl/well, 15 minutes in the dark) and the reaction was halted with the addition of 50 μl/well of 0.18 M $H_2SO_4$. Absorbance at 450 nm was measured with a Molecular Devices microplate reader. To calculate antibody titers, a positive control curve is generated and titers of unknown samples are extrapolated from the curve using computer software.

BHV-1 gD ELISA

Serum samples were collected at study days 0, 20, 31, 41, 55, 62, 69, and 146 and were evaluated for anti gD BHV-1 antibody titers by ELISA. Purified recombinant gD BHV-1 expressed from MDBK (Madin Darby Bovine Kidney) cells (1 μg/mL in Dulbecco's PBS+0.01% thimerosal, 100 μL/well) was adsorbed onto microtiter plates for 18–24 hours at 4° C. Excess protein was washed from wells then unbound sites in wells were blocked by incubating for 2 hours at 37° C. with 300 μl of 1%PVA (polyvinyl acetate) in DPBS (Dulbecco's phosphate buffered saline) with 0.01% thimerosol. Serum samples (positive and negative control and unknown serum) were diluted 1:50, then serially by 4-fold dilutions in 1%PVA in DPBS with 0.01% thimerosol and 100 μl added to each well. The assay was incubated 45 minutes at 37° C. Plates were washed four times with distilled $H_2O$, then HRP (horse radish peroxidase) goat anti-mouse (1:10000 in 1%PVA in DPBS with 0.01% thimerosol, 100μl/well, KP+L) was added and plates were incubated 30 minutes at 37° C. Wells were washed four times with distilled $H_2O$ then the assay was developed with ABTS (2,2'-azino-di[3-ethyl-benzthiazoline sulfonate (6) substrate (100 μl/well, RT, 15 min). The reaction was read at 405/490 nm on an ELISA reader. Titers were calculated using the Forecast method in EXCEL™ (Microsoft, Redmond, Wash.) using 0.5 OD as a cutoff and using 2 dilutions above 0.5 and 1 dilution below the 0.5 OD to extrapolate titers.

Testosterone Concentrations

Serum samples from study days 0, 41 and 69 were evaluated for testosterone concentrations. The assay was a human testosterone radioimmunoassay using antibody that cross-reacts with murine testosterone. Human testosterone standards are used in the assay. The murine samples tend to run at the lower end of the human testosterone standard curve, leading to a wider variability in normal values. The sensitivity of the assay is 0.02 ng/mL.

Necropsy and Histopathology

Animals were sacrificed at study day 146. Testes, epididymides and prostate with seminal vesicle were removed and weighed prior to fixation of tissues in Bouin's fixative [75 mL picric acid (saturated solution); 25 mL formalin (37%); 5 mL acetic acid (4.76%)]. Tissues were fixed for 48 hours then rinsed in 50% ethanol:$H_2O$. Tissues were stored in fresh 50% ethanol prior to analysis. Tissues were processed and embedded in paraffin and 5 μm sections cut and stained with hematoxylin and eosin. Each organ was evaluated for inflammation, atrophy, and spermatogonial degeneration. Scores were assigned based on the level of aspermatogenesis, atrophy, or other lesions. Weights were scored as a percentage of the mean weight in the normal control group. A cumulative score was assigned to each animal.

Results

Anti-gD Antibody Responses

All mice that were Immunized with gD or a gD-containing fusion protein generated anti-gD ELISA antibodies, regardless of whether gD was expressed in procaryotic (i.e. *E.coli* expressed carboxyl, amino or carboxyl-amino fusion protein) or eucaryotic expression systems (i.e. MDBK expressed protein).

Anti-GnRH Antibody Responses

A hierarchy of anti-GnRH titers were induced by the different fusion proteins: tmgD-4GnRH (i.e. having a GnRH tetramer at the carboxy end of the protein) generated the highest titers followed by 4GnRH-tmgD-4GnRH, while the lowest titers were induced in the 4GnRH-tmgD immunized. In all groups anti-GnRH titers peaked after the second immunization and remained at plateau for greater than 2 months.

All (9 of 9) mice immunized with the tmgD-4GnRH made antibody responses to GnRH when measured by peptide ELISA, although 2/9 mice were low responders. There were 3/10 nonresponders in the 4GnRH-tmgD group and 1/9 nonresponders in the 4GnRH-tmgD-4GnRH. All the GnRH nonresponders were gD responders.

Effect of Anti-GnRH Antibodies on the Male Reproductive System

To determine whether induction of anti-GnRH antibodies would abrogate GnRH function we evaluated testosterone levels before and after GnRH immunization. At necropsy, reproductive tract tissues were weighed then submitted for gross and histological examination. The normal ranges of testosterone concentrations in mice varied widely as measured using the human testosterone radioimmunoassay. However, mice immunized with tmgD-4GnRH had significantly lower mean testosterone concentrations when compared to normal controls or other treatment groups. The prostate, testes and epididymides of tmgDAGnRH immunized mice were significantly atrophied when gross tissue weight and histological examination of sperm development was evaluated. Mice immunized with 4GnRH-tmgD-4GnRH were less affected when compared to normal controls.

Example 4

Baculovirus Constructs Encoding gD/GnRH Fusion Proteins

Construction of pBacHISgD:LH and bac-gD:GnRH pQE-gD:GnRH (see Example 1) was digested with Hind III, the site blunt-ended by Klenow treatment, and subsequently digested with EcoRI. An approximate 1.2 kb fragment which contained the tmgD-4GnRH coding sequence was gel purified and cloned into STUI/EcoRI digested transfer vector pBacPAK9 plasmid (Clontech, Inc.), forming pBacHISgD:LH. (The transfer vector contains sequences compensating for replication deficiency in a replication deficient baculovirus.)

Sf21 insect cells were co-transfected with pBacHIS-gD:LH and replication deficient baculovirus viral DNA. These transfected Sf21 cells generate a recombinant baculovirus (designated bac-gD:GnRH) (ATCC Accession No. VR-2633), which encodes a tmgD-4GnRH fusion protein. Recombination (exchange of DNA) between the transfer vector pBacHISgD:LH and replication deficient baculovirus viral DNA is mediated by homologous flanking viral sequences present in pBacPAK9 which allows for efficient transfer of the entire expression cassette (sequence encoding tmgD-4GnRH) from pBacHISgD:LH into viral DNA along with the gene or genes that complements for replication deficiency.

Recombinant virus can be purified by plaque assay from infected Sf21 cells. Repeated cycles of Sf21 cell infection and plaque assay purification can be performed to obtain greater concentration of recombinant virus expressing fusion protein for large scale production of the fusion protein. Expression of the recombinant constructs was confirmed by Western blot. Infected Sf21 cells can be collected by centrifugation and transferred to −80° Celsius until processed for recombinant baculovirus.

The nucleotide sequence encoding the ORF for the 6×HIS tag, truncated mature gD and GnRH tetramer in bac-gD:GnRH is set forth in SEQ ID NO: 39. Nucleotides #1–45 encode a 6×HIS tag, nucleotides #46–1074 encode a truncated mature BHV-1 gD, nucleotides #1075–1194 encode a GnRH tetramer, and nucleotides #1195–1197 are a stop codon. The amino acid sequence of the fusion protein encoded by bac-gDGnRH is the same as the sequence set forth in SEQ ID NO: 25.

Construction of pBacHISMgD

A recombinant baculovirus construct containing gD was generated as a control. Plasmid pCMV-MgD (see Example 5, infra) was digested with PacI and ApaI allowing for the isolation of a 950 bp fragment containing the majority of the gD gene minus the 5' end. Plasmid pBacHISgD,LH underwent digestion with PacI and ApaI allowing for the isolation of a 5.6 kb fragment containing the plasmid backbone and the 5' portion of gD. Ligation of the 5.6 kb fragment with the 950 bp fragment generated plasmid pBacHISMgD containing truncated mature gD in transfer vector, pBacPAC9.

Sf21 cells were co-transfected with pBacHISMgD and replication deficient virus. These transformed Sf21 cells generate recombinant baculovirus (designated Bac-MgD) which encodes tmgD. Recombinant virus was purified and stored as described above.

Expression

Recombinant baculovirus can be obtained from lysates of infected Sf21 cells. The lysate also contains the fusion protein expressed by the recombinant virus, and the fusion protein may be purified from the lysate. For example, after detergent lysis of the cell pellet, the lysate pellet in the aforementioned example was solubilized in 8 M urea, 50 mM Tris, pH 7.5 and loaded onto a Ni NTA column; the tmgD-4GnRH was eluted in a pH step gradient. The lysate, containing both the recombinant baculovirus and fusion protein, can be stored, for example, at −80° Celsius.

Example 5

Plasmid Suitable for in vivo Expression of gD/GnRH Fusion Proteins

The β-Gal gene from pCMVβ vector (Clontech, Inc) was removed by EcoRV/NotI restriction digest and the resulting NotI vector fragment was isolated by gel electrophoresis. A synthetic linker containing multiple cloning sites (MC) with NotI ends was cloned into this NotI vector fragment creating pCMV-MC.

A truncated gD gene including the signal sequence was PCR amplified from FlgDlPots207nco(#79) using primers that introduced an EcoRV site at 5' end, a second codon repaired to encode Gln rather than Glu, a stop codon added after Pro 337 of the coding sequence, and a KpnI site added at the 3' end. This 1083 bp PCR fragment was cloned into EcoRV/KpnI digested pGEM-T EASY vector (Promega, Madison, Wis.), generating pGEM-T-EASY/gD, and subsequently sequenced by fluorescent di-deoxy termination chemistry in both directions to ensure integrity of PCR product. The truncated gD fragment was isolated from the pGEM-T-EASY/gD clone by EcoRV/KpnI digestion and subcloned into pCMV-MC. The resulting done, designated pCMV-gD, was verified by restriction enzyme analysis.

To construct pCMV-gD:GnRH (ATCC accession No. 203370). pQE-gD:GnRH was cleaved with HindIII, blunt ended with Klenow and then digested with ApaI. The resulting blunt-ended/ApaI 1.05 kb fragment containing tmgD and GnRH tetramer was isolated. Clone, pCMV-gD was cleaved with SmaI, followed by ApaI, removing the truncated gD encoding region. The remaining 3.7 kb pCMV vector fragment containing the signal sequence for gD was isolated and used in a ligation reaction with the 1.05 kb fragment containing tmgD and GnRH tetramer. The resulting clone was designated pCMV-gD:GnRH. The ORF encoding the tgD-4GnRH, including the signal sequence, from pCMV-gD:GnRH is set forth in SEQ ID NO: 28. The amino acid sequence of the tgD-4GnRH, including the signal sequence, encoded by pCMV-gD:GnRH is set forth in SEQ ID NO: 29.

All patents, patent applications, and publications cited above are incorporated herein by reference in their entirety.

The present invention is not to be limited in scope by the specific embodiments described herein, which are intended as single illustrations of individual aspects of the invention, and functionally equivalent methods and components are within the scope of the invention. Indeed, various modifications of the invention, in addition to those shown and described herein will become apparent to those skilled in the art from the foregoing description and accompanying drawings. Such modifications are intended to fall within the scope of the appended claims.

DEPOSIT OF BIOLOGICAL MATERIALS

The following biological material was deposited with the American Type Culture Collection (ATCC) at 10801 University Blvd., Manassas, Va., 20110-2209, USA, on Oct. 22, 1998 and were assigned the following accession numbers:

| Plasmid | Accession No. |
| --- | --- |
| plasmid pQE-gD:GnRH | 98953 |
| plasmid pCMV-gD:GnRH | 203370 |
| plasmid pQE-GnRH:gD | 98954 |
| plasmid pQE-GnRH:gD:GnRH | 98955 |
| Vector | Accession No. |
| baculovirus bac-gD:GnRH | VR-2633 |

All patents, patent applications, and publications cited above are incorporated herein by reference in their entirety.

The present invention is not to be limited in scope by the specific embodiments described herein, which are intended as single illustrations of individual aspects of the invention, and functionally equivalent methods and components are within the scope of the invention. Indeed, various modifications of the invention, in addition to those shown and described herein will become apparent to those skilled in the art from the foregoing description and accompanying drawings. Such modifications are intended to fall within the scope of the appended claims.

What is claimed is:

1. A fusion protein for producing an immune response in a vertebrate, which fusion protein comprises:
   (a) a first proteinaceous portion comprising a peptide sequence of the gonadotropin releasing hormone (GnRH) peptide as set forth in SEQ ID NO: 13 connected to (b) a second proteinaceous portion comprising a polypeptide sequence of the Bovine Herpes Virus Type-1 (BHV-1) gD protein as set forth in SEQ ID NO: 29;
   wherein the activity of said GnRH peptide is to be inhibited within the vertebrate, and which proteinaceous portion by itself is incapable of eliciting an effective immunoinhibitory response in said vertebrate and when the vertebrate is vaccinated with an effective amount of said fusion protein, the vertebrate recognizes said first proteinaceous portion (a) and induces an immune response capable of inhibiting the activity of said GnRH peptide within the vertebrate.

2. A fusion protein for producing an immune response in a vertebrate, which fusion protein comprises:
   (a) a first proteinaceous portion comprising a peptide sequence of the GnRH peptide as set forth in SEQ ID NO: 13 connected to (b) a second proteinaceous portion comprising a polypeptide sequence of the BHV-1 gD protein as set forth in SEQ ID NO: 29;

wherein the activity of said GnRH peptide is to be inhibited within the vertebrate, and which proteinaceous portion by itself is incapable of eliciting an effective immunoinhibitory response in said vertebrate and when the vertebrate is vaccinated with an effective amount of said fusion protein, the vertebrate recognizes said first proteinaceous portion (a) and induces an immune response capable of inhibiting the activity of said GnRH peptide within the vertebrate.

* * * * *